(12) United States Patent
Astermark et al.

(10) Patent No.: US 9,644,239 B2
(45) Date of Patent: May 9, 2017

(54) GENETIC FACTORS ASSOCIATED WITH INHIBITOR DEVELOPMENT IN HEMOPHILIA A

(75) Inventors: Jan Astermark, Malmö (SE); Erik Berntorp, Malmö (SE)

(73) Assignees: Jan Astermark, Malmö (SE); Erik Berntorp, Malmö (SE)

( * ) Notice: Subject to any disclaimer, the term of this patent is extended or adjusted under 35 U.S.C. 154(b) by 809 days.

(21) Appl. No.: 13/207,286

(22) Filed: Aug. 10, 2011

(65) Prior Publication Data
US 2012/0065077 A1  Mar. 15, 2012

Related U.S. Application Data

(63) Continuation of application No. 13/091,968, filed on Apr. 21, 2011.
(60) Provisional application No. 61/326,602, filed on Apr. 21, 2010.

(51) Int. Cl.
C40B 30/04 (2006.01)
C12Q 1/68 (2006.01)

(52) U.S. Cl.
CPC ..... *C12Q 1/6883* (2013.01); *C12Q 2600/106* (2013.01); *C40B 30/04* (2013.01)

(58) Field of Classification Search
None
See application file for complete search history.

(56) References Cited

FOREIGN PATENT DOCUMENTS

WO   WO 2008/059009 A2   5/2008

OTHER PUBLICATIONS

NCBI Reference SNP (refSNP) Cluster Report downloaded on Jun. 16, 2014 from http://www.ncbi.nlm.nih.gov/projects/SNP/snp_ref.cgi?rs=11744216.*
NCBI Reference SNP (refSNP) Cluster Report downloaded on Jun. 16, 2014 from http://www.ncbi.nlm.nih.gov/projects/SNP/snp_ref.cgi?rs=3211834.*
NCBI Reference SNP (refSNP) Cluster Report downloaded on Jun. 16, 2014 from http://www.ncbi.nlm.nih.gov/projects/SNP/snp_ref.cgi?rs=1863993.*
NCBI Reference SNP (refSNP) Cluster Report downloaded on Jun. 16, 2014 from http://www.ncbi.nlm.nih.gov/projects/SNP/snp_ref.cgi?rs=1567748.*
Affymetrix, "Data Sheet: Affymetrix® Genome-Wide Human SNP Array 6.0," 2007, retrieved from <http://www.affymetrix.com/support/technical/datasheets/genomewide_snp6_datasheet.pdf>, retrieved on Apr. 10, 2009, 4 pages.
Annex to Form PCT/ISA/206 Communication Related to the Results of the Partial International Search Report, for International Application No. PCT/EP2011/056471, filed on Apr. 21, 2011, 3 pages.

Astermark, J., "Overview of Inhibitors," *Seminars in Hematology*, 2006, vol. 43 (Suppl. 4), pp. S3-S7.
Astermark, J., "Why do inhibitors develop? Principles of and factors influencing the risk for inhibitor development in haemophilia," *Haemphilia*, 2006, vol. 12 (Suppl. 3), pp. 52-60.
Astermark, J., "Inhibitor development: patient-determined risk factors," *Haemophilia*, 2010, vol. 16, pp. 66-70.
Astermark, J., "Immune tolerance induction in patients with hemophilia A," *Thrombosis Research*, 2011, vol. 127, pp. S6-S9.
Astermark, J. et al., "Malmö International Brother Study (MIBS): An International Survey of Brother Pairs with Haemophilia," *Vox Sanguinis*, 1999, vol. 77 (Suppl. 1), pp. 80-82.
Astermark, J. et al., "The Malmö International Brother Study (MIBS): further support for genetic predisposition to inhibitor development," *Haemophilia*, 2001, vol. 7, pp. 267-272.
Astermark, J. et al., "The Malmö International Brother Study (MIBS). Genetic defects and inhibitor development in siblings with severe hemophilia A," *Haematologica/The Hematology Journal*, 2005, vol. 90, No. 7, pp. 924-930.
Astermark, J. et al., "Polymorphisms in the *IL10* but not in the *IL1beta* and *IL4* genes are associated with inhibitor development in patients with hemophilia A," *Blood*, Apr. 15, 2006, vol. 107, No. 8, pp. 3167-3172.
Astermark, J. et al., "Polymorphisms in the *TNFA* gene and the risk of inhibitor development in patients with hemophilia A," *Blood*, Dec. 1, 2006, vol. 108, No. 12, pp. 3739-3745.
Astermark, J. et al., "Polymorphism in the CTLA-4 gene and inhibitor development in patients with severe hemophilia A," *Journal of Thrombosis and Haemostasis*, 2007, vol. 5, pp. 263-265.
Astermark, J. et al., "Inhibitor Development," *Haemophilia*, 2008, vol. 14 (Suppl. 3), pp. 36-42.
Astermark, J. et al., "Clinical issues in inhibitors," *Haemophilia*, 2010, vol. 16 (Suppl. 5), pp. 54-60.
Berntorp, E. et al., "Haemophilia Inhibitor Genetics Study—evaluation of a model for studies of complex diseases using linkage and association methods," *Haemophilia*, 2005, vol. 11, pp. 427-429.
Coppola, A. et al., "Factor VIII gene (*F8*) mutations as predictors of outcome in immune tolerance induction of hemophilia A patients with high-responding inhibitors," *Journal of Thrombosis and Haemostatis*, 2009, vol. 7, pp. 1809-1815.
Gouw, S.C. et al., "The Multifactorial Etiology of Inhibitor Development in Hemophilia: Genetics and Environment," *Seminars in Thrombosis and Hemostasis*, 2009, vol. 35, No. 8, pp. 723-734.
Hay, C.R.M. et al., "HLA Class II Profile: A Weak Determinant of Factor VIII Inhibitor Development in Severe Haemophilia A," *Thrombosis and Haemostasis*, 1997, vol. 77, No. 2, pp. 234-237.
Lee, C.A. et al., "Inhibitor Development in Hemophiliacs: The Roles of Genetic versus Environmental Factors," *Seminars in Thrombosis and Haemostasis*, 2006, vol. 32 (Suppl. 2), pp. 10-14.
Lippert, L.E. et al., "Relationship of Major Histocompatibility Complex Class II Genes to Inhibitor Antibody Formation in Hemophilia A," *Thrombosis and Haemostasis*, 1990, vol. 64, No. 4, pp. 564-568.

(Continued)

*Primary Examiner* — Christian Boesen
(74) *Attorney, Agent, or Firm* — Morgan, Lewis & Bockius LLP

(57) ABSTRACT

The present invention provides methods for predicting the risk of an individual developing antibodies to factor VIII by identifying a single nucleotide polymorphism of an immune response or immune modifier gene. The invention further provides oligonucleotides, diagnostic kits, microarrays, and isolated nucleic acids comprising single nucleotide polymorphisms of immune response or immune modifier genes.

26 Claims, No Drawings

(56) References Cited

OTHER PUBLICATIONS

Oldenburg, J. et al., "HLA Genotype of Patients with Severe Haemophilia A due to 22 Inversion with and without Inhibitors of Factor VIII," *Thrombosis and Haemostasis*, 1997, vol. 77, No. 2 , pp. 238-242.

Oldenburg, J. et al., "Genetic risk factors for inhibitors to factors VIII and IX," *Haemophilia*, 2006, vol. 12 (Suppl. 6), pp. 15-22.

Pavlova, A. et al., "Impact of polymorphisms of the major histocompatibility complex class II, interleukin-10, tumor necrosis factor-α and cytotoxic T-lymphocyte antigen-4 genes on inhibitor development in sever hemophilia A," *Journal of Thrombosis and Haemostasis*, 2009, vol. 7, pp. 2006-2015.

Pavlova, A. et al., "HLA genotype in patients with acquired haemophilia A," *Haemophilia*, 2010, vol. 16, pp. 107-112.

Rocino, A. et al., "Immune tolerance induction with recombinant factor VIII in hemophilia A patients with high responding inhibitors," *Haematologica/The Hematology Journal*, 2006, vol. 91, No. 4, pp. 558-561.

Salviato, R. et al., "*F8* gene mutation profile and ITT response in a cohort of Italian haemophilia A patients with inhibitors," *Haemophilia*, 2007, vol. 13, pp. 361-372.

Wight, J. et al., "Immune tolerance induction in patients with haemophilia A with inhibitors: a systematic review," *Haemophilia*, 2003, vol. 9, pp. 436-463.

Zhang, A.H. et al., "Factor VIII Inhibitors: Risk Factors and Methods for Prevention and Immune Modulation," *Clinic. Rev. Allerg. Immunol.*, 2009, vol. 37, pp. 114-124.

Ahn. S-M. et al., "The first Korean genome sequence and analysis: Full genome sequencing for a socio-ethnic group," *Genome Research*, 2009, vol. 19, pp. 1622-1629.

Aledort, L.M. et al., "Comparative thrombotic even incidence after infusion of recombinant factor VIIa versus factor VIII inhibitor bypass activity," *Journal of Thrombosis and Haemostasis*, 2004, vol. 2, pp. 1700-1708.

Reference SNP (refSNP) Cluster Report: rs4147385, downloaded from <http://www.ncbi.nlm.nih.gov/projects/SNP/snp_ref.cgi?re=4147385> on Dec. 16, 2013, 3 pages.

Reference SNP (refSNP) Cluster Report: rs13206518, downloaded from <http://www.ncbi.nlm.nih.gov/projects/SNP/snp_ref.cgi?rs=13206518> on Dec. 16, 2013, 2 pages.

Schadt, E.E. et al., "Mapping the Genetic Architecture of Gene Expression in Human Liver," *PLOS Biology*, May 2008, vol. 6, No. 5, e107, pp. 1020-1032.

Affymetrix, "Data Sheet: Affymetrix® Genome-Wide Human SNP Array 6.0," 2009, retrieved from <http://www.affymetrix.com/support/technical/datasheets/genomewide_snp6_datasheet.pdf> 4 pages.

NCBI Assay ID (ss#): ss76680612, entry date: Aug. 28, 2007, retrieved from <www.ncbi.nlm.nih.gov/projects/SNP/snp_retrieve.cgi?subsnp_id=76680612>, 1 page.

Astermark, J. et al., "The polygenic nature of inhibitors in hemophilia A: results from the Hemophilia Inhibitor Genetics Study (HIGS) Combined Cohort," Thrombosis and Hemostatis, Feb. 21, 2013; 121(8):1446-1454.

U.S. Appl. No. 13/091,968, filed Apr. 21, 2011.

Astermark, J. et al., "Genetic Factors Associated with Inhibitor Development in Hemophilia A: Initial Results From the Hemophilia Inhibitor Genetics Study (HIGS) Combined Cohort," Blood, 2009, vol. 114, Abstract 217, 2 pages.

\* cited by examiner

GENETIC FACTORS ASSOCIATED WITH INHIBITOR DEVELOPMENT IN HEMOPHILIA A

CROSS-REFERENCES TO RELATED APPLICATIONS

The present application claims the benefit of U.S. Provisional Application No. 61/326,602, filed Apr. 21, 2010, which is expressly incorporated herein by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Blood coagulation is a complex and dynamic biological process that depends on a series of interdependent biochemical reactions. Coagulation factor VIII (FVIII) is a key component of the blood coagulation cascade. When a bleed occurs, FVIII is directed to the bleeding site and forms a Xase complex with activated factor IX (FIXa) and factor X (FX). The Xase complex activates FX, which in turn activates prothrombin to thrombin, which activates other components in the coagulation cascade to generate a stable clot (reviewed in Saenko et al., Trends Cardiovasc. Med., 9:185-192 (1999); Lenting et al., Blood, 92:3983-3996 (1998)). In hemophilia A, a congenital X-linked bleeding disorder characterized by a deficiency in FVIII, the lack of functional FVIII hampers this positive feedback loop, resulting in incomplete coagulation, which manifests as bleeding episodes of increased duration rather than increased intensity (Zhang et al., Clinic. Rev. Allerg. Immunol., 37:114-124 (2009)).

The severity of hemophilia A varies based on the nature of any mutation to FVIII and the extent of function of any endogenous FVIII that is formed. About two thirds of patients have "severe" hemophilia, characterized as less than 1% functional FVIII. Patients with "moderate" hemophilia have about 1-5% functional FVIII, and patients with "mild" hemophilia have about 5-50% of normal FVIII function (Zhang et al., Clinic. Rev. Allerg. Immunol., 37:114-124 (2009)). Current treatment for hemophilia typically consists of factor VIII replacement therapy, in which the patient receives recombinant or plasma-derived factor VIII to prevent or treat bleeding episodes. However, in approximately 25-30% of patients with severe hemophilia A and in approximately 5% of patients with mild to moderate hemophilia A, inhibitory alloantibodies are produced against FVIII, abrogating the effectiveness of this treatment (Oldenburg and Pavlova, Haemophilia, 12 (suppl. 6):15-22 (2006)).

Inhibitor development is considered to be the most significant complication in the treatment of hemophilia. Patients with inhibitors have a higher mortality rate because their bleeding episodes become more difficult and costly to treat, and preventative treatment is generally not possible in these patients. In patients with high-titer inhibitors, there is an increased risk of developing recurrent bleeding in particular joints, which may ultimately result in decreased quality of life, disability, or death from excessive blood loss (Zhang et al., Clinic. Rev. Allerg. Immunol., 37:114-124 (2009); Gouw and van den Berg, Semin. Thromb. Hemost., 35:723-734 (2009)). Although in some cases immune tolerance induction can eradicate FVIII inhibitors in patients with hemophilia A, relapse is possible and not all patients reach immune tolerance (Wight et al., Haemophilia, 9:436-463 (2003)).

Accordingly, there is a need in the art for the identification of genetic markers that are associated with increased likelihood of developing inhibitory antibodies to FVIII and for corresponding methods of identifying the presence of these genetic markers in hemophiliac patients. Prior or early identification of such genetic markers could lead to dose and/or timing adjustments and to the use of alternative therapies to avoid the development of antibodies to FVIII.

BRIEF SUMMARY OF THE INVENTION

In one aspect, the present invention provides a method for predicting the risk of developing antibodies against Factor VIII (FVIII) in an individual diagnosed with Hemophilia, the method comprising the steps of: (a) detecting the presence of at least one single nucleotide polymorphism (SNP) selected from the group consisting of a SNP listed in Table 1, a SNP listed in Table 2, a SNP listed in Table 3, and a SNP listed in Table 4, in a biological sample from the individual; and (b) predicting the risk of the individual of developing antibodies to FVIII. In a preferred embodiment, the at least one SNP is selected from those listed in Table 3. In another preferred embodiment, the at least one SNP is selected from the group consisting of rs12368829, rs11744216, rs1863993, rs4147385, rs12546235, rs4242389, rs10054825, rs17535213, rs10072056, and rs17725712.

In a second aspect, the present invention provides a method for predicting the risk of developing antibodies against Factor VIII (FVIII) in an individual diagnosed with severe Hemophilia, the method comprising the steps of: (a) detecting the presence of at least one single nucleotide polymorphism (SNP) selected from the group consisting of a SNP listed in Table 2 and a SNP listed in Table 4, in a biological sample from the individual; and (b) predicting the risk of the individual of developing antibodies to FVIII. In a preferred embodiment, the at least one SNP is selected from those listed in Table 4. In another preferred embodiment, the at least one SNP is selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888.

In a third aspect, the present invention provides a method for assigning treatment comprising administration of Factor VIII (FVIII) to an individual diagnosed with Hemophilia, the method comprising the steps of: (a) detecting the presence of at least one single nucleotide polymorphism (SNP) selected from the group consisting of a SNP listed in Table 1, a SNP listed in Table 2, a SNP listed in Table 3, and a SNP listed in Table 4, in a biological sample from the individual; and (b) predicting the risk of the individual of developing antibodies to FVIII, and (c) assigning therapy comprising administration of Factor VIII to the individual. In a preferred embodiment, the at least one SNP is selected from those listed in Table 3. In another preferred embodiment, the at least one SNP is selected from the group consisting of rs12368829, rs11744216, rs1863993, rs4147385, rs12546235, rs4242389, rs10054825, rs17535213, rs10072056, and rs17725712.

In a fourth aspect, the present invention provides a method for assigning treatment comprising administration of Factor VIII (FVIII) to an individual diagnosed with severe Hemophilia, the method comprising the steps of: (a) detecting the presence of at least one single nucleotide polymorphism (SNP) selected from the group consisting of a SNP listed in Table 2 and a SNP listed in Table 4, in a biological sample from the individual; and (b) predicting the risk of the individual of developing antibodies to FVIII, and (c) assigning therapy comprising administration of Factor VIII to the individual. In a preferred embodiment, the at least one SNP is selected from those listed in Table 4. In another preferred embodiment, the at least one SNP is selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888.

In a fifth aspect, the present invention provides a method for assigning treatment comprising administration of Factor VIII bypass therapy to an individual diagnosed with Hemophilia, the method comprising the steps of: (a) detecting the presence of at least one single nucleotide polymorphism (SNP) selected from the group consisting of a SNP listed in Table 1, a SNP listed in Table 2, a SNP listed in Table 3, and a SNP listed in Table 4, in a biological sample from the individual; and (b) predicting the risk of the individual of developing antibodies to FVIII, and (c) assigning therapy comprising administration of Factor VIII bypass therapy to the individual. In a preferred embodiment, the at least one SNP is selected from those listed in Table 3. In another preferred embodiment, the at least one SNP is selected from the group consisting of rs12368829, rs11744216, rs1863993, rs4147385, rs12546235, rs4242389, rs10054825, rs17535213, rs10072056, and rs17725712.

In a sixth aspect, the present invention provides a method for assigning treatment comprising administration of Factor VIII bypass therapy to an individual diagnosed with severe Hemophilia, the method comprising the steps of: (a) detecting the presence of at least one single nucleotide polymorphism (SNP) selected from the group consisting of a SNP listed in Table 2 and a SNP listed in Table 4, in a biological sample from the individual; and (b) predicting the risk of the individual of developing antibodies to FVIII, and (c) assigning therapy comprising administration of Factor VIII bypass therapy to the individual. In a preferred embodiment, the at least one SNP is selected from those listed in Table 4. In another preferred embodiment, the at least one SNP is selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888.

In a seventh aspect, the present invention provides a diagnostic kit for predicting the risk of developing antibodies against Factor VIII (FVIII) in an individual diagnosed with Hemophilia, the kit comprising at least one oligonucleotide capable of being used to detect at least one single nucleotide polymorphism (SNP) selected from the group consisting of a SNP listed in Table 1, a SNP listed in Table 2, a SNP listed in Table 3, and a SNP listed in Table 4. In a preferred embodiment, the at least one SNP is selected from those listed in Table 3. In another preferred embodiment, the at least one SNP is selected from the group consisting of rs12368829, rs11744216, rs1863993, rs4147385, rs12546235, rs4242389, rs10054825, rs17535213, rs10072056, and rs17725712.

In an eighth aspect, the present invention provides a diagnostic kit for predicting the risk of developing antibodies against Factor VIII (FVIII) in an individual diagnosed with severe Hemophilia, the kit comprising at least one oligonucleotide capable of being used to detect at least one single nucleotide polymorphism (SNP) selected from the group consisting of a SNP listed in Table 2 and a SNP listed in Table 4. In a preferred embodiment, the at least one SNP is selected from those listed in Table 4. In another preferred embodiment, the at least one SNP is selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888.

In a ninth aspect, the present invention provides a microarray for predicting the risk of developing antibodies against Factor VIII (FVIII) in an individual diagnosed with Hemophilia, the microarray comprising a support having a plurality of discrete regions, each discrete region having a nucleic acid fragment spotted thereon, wherein at least one nucleic acid fragment spotted on the support comprises a sequence that is complementary to a genomic sequence that flanks a single nucleotide polymorphism (SNP) selected from the group consisting of a SNP listed in Table 1, a SNP listed in Table 2, a SNP listed in Table 3, and a SNP listed in Table 4. In a preferred embodiment, the at least one SNP is selected from those listed in Table 3. In another preferred embodiment, the at least one SNP is selected from the group consisting of rs12368829, rs11744216, rs1863993, rs4147385, rs12546235, rs4242389, rs10054825, rs17535213, rs10072056, and rs17725712.

In a tenth aspect, the present invention provides a microarray for predicting the risk of developing antibodies against Factor VIII (FVIII) in an individual diagnosed with severe Hemophilia, the microarray comprising a support having a plurality of discrete regions, each discrete region having a nucleic acid fragment spotted thereon, wherein at least one nucleic acid fragment spotted on the support comprises a sequence that is complementary to a genomic sequence that flanks a single nucleotide polymorphism (SNP) selected from the group consisting of a SNP listed in Table 2 and a SNP listed in Table 4. In a preferred embodiment, the at least one SNP is selected from those listed in Table 4. In another preferred embodiment, the at least one SNP is selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888.

Table 1. SNPs associated with inhibitor status in the Hemophilia Inhibitor Genetics Study (HIGS) Combined Cohort, as determined in the study described in Example 1.

Table 2. SNPs associated with inhibitor status in a subgroup of individuals with severe hemophilia, as determined in the study described in Example 1.

Table 3. SNPs associated with inhibitor status in the Hemophilia Inhibitor Genetics Study (HIGS) Combined Cohort, as determined in the study described in Example 2.

Table 4. SNPs associated with inhibitor status in a subgroup of individuals with severe hemophilia, as determined in the study described in Example 2.

DETAILED DESCRIPTION OF THE INVENTION

I. Introduction

The development of inhibitory alloantibodies against factor VIII is intricately connected with an individual's immune response to FVIII. For this reason, it has been proposed that risk factors associated with inhibitor development may include genotypes or polymorphisms associated with immune and inflammatory response. The immune response to FVIII is believed to develop as an immune response to an external antigen: the antigen is recognized and processed by antigen-presenting cells (APCs) into smaller fragments, then presented on the surface of the APCs in association with major histocompatibility complex (MHC) class II molecules, where it can be recognized by CD4+ T cells specific for FVIII, which in turn, in the presence of costimulatory signals, direct B cells to generate antibodies to FVIII (reviewed in Reding, *Haemophilia*, 12 (Suppl. 6):30-36 (2006)).

Several studies have found a weak association between MLC/human leukocyte antigen (HLA) class I alleles A3, B7, and C7, and MLC/HLA class II alleles DQA0102, DQB0602, DR15 and higher risk of inhibitor development, while HLA class I allele C2 and HLA class II alleles DQA0103, DQB0603, and DR13 were weakly associated with a protective effect against inhibitor development (Oldenburg et al., *Thromb Haemost*, 77:238-242 (1997); Hay et al., *Thromb Haemost*, 77:234-237 (1997)). However, other studies, including the more recent Malmo International Brother Study (MIBS), have not found any associations between HLA genotype and inhibitor development (Lippert et al., *Thromb Haemost*, 64:564-568 (1990); Astermark et al., *Blood*, 108:3739-3745 (2006)). Other studies have found associations between inhibitor development and a single nucleotide polymorphism (SNP) in the promoter region of TNFA, encoding the immunomodulatory and pro-inflammatory cytokine tumor necrosis factor α (Astermark et al., *Blood*, 108:3739-3745 (2006)); a 134 bp long variant of a CA repeat microsatellite in the promoter region of IL10, encoding the anti-inflammatory cytokine interleukin-10 (Astermark et al., *Blood*, 107:3167-3172 (2006)); and a SNP in the promoter region of CTLA4, encoding cytotoxic T-lymphocyte associated protein-4, a receptor mainly displayed on activated T-cells (Astermark et al., *J. Thromb. Haemost.*, 5:263-265 (2007)). However, no association was found between inhibitor development and polymorphisms in IL1beta and IL4, which encode cytokines and which have both been associated with risk of developing other autoimmune disorders (Astermark et al., *Blood*, 107:3167-3172 (2006)). It is clear that other genetic markers influencing the immune response to FVIII remain to be identified. Recently, Pavlova et al. (Pavlova A et al., *Haemophilia* 2010 May; 16(102):107-12) identified a significantly higher frequency of DRB1*16 [odds ratio (OR) 10.2, 95% CI: 5.32-19.57, P<0.0001] and DQB1*0502 (OR 2.2, 95% CI: 1.12-4.54, P<0.05) HLA class II aleles was observed in patients with acquired hemophilia A (AH). In contrast, the frequency of DRB1*15 and DQB1*0602 alleles was found to be decreased in patients with AH corresponding to an OR of 0.4 for both HLA loci.

The present invention relates to the discovery that SNPs in multiple other immune response, immune modulator, and inflammatory response genes are associated with inhibitor development in hemophiliac patients. In the present invention, a combined cohort of three study populations, the Hemophilia Inhibitor Genetics Study (HIGS), the Malmö International Brother Study (MIBS), and the Hemophilia Growth and Development Study (HGDS), was formed to conduct an association study to test the hypothesis that antibody development to FVIII is mediated by immune response and immune modifier genes. It was discovered that out of 14,626 SNPs from 1,081 genes including cytokines and their receptors, chemokines and their receptors, pathway genes involved in inflammatory and immune responses, and HLA genes, 329 SNPs were associated with FVIII inhibitor status. The 329 SNPs of the present invention are described herein, e.g. in Tables 1, 2, 3, and 4. The SNPs described herein can be used to predict the risk of an individual developing antibodies to FVIII. Predicting whether an individual is at risk of developing antibodies to FVIII, whether it is prior to the individual receiving FVIII therapy or once the individual has begun receiving FVIII therapy, is important because such a prediction makes it possible to adjust the dosage and/or timing of FVIII therapy provided to the individual, or to provide or adjust an alternative therapy such as bypass therapy, in order to avoid the individual developing antibodies to FVIII.

The present invention also relates to the discovery of strong SNP associations between inhibitor development and six markers within five genes. It was discovered that in the combined cohort, strong SNP associations with FVIII inhibitor status for the total group were observed in the DOCK2, MAPK9, F13A1, CD36, and PTPRR genes. A strong SNP association was found for the SNP rs11744216, a C>G variant in an intronic region of the DOCK2 gene (odds ratio or "OR" of 0.28 and a p-value or "p" of 0.00004); for the SNP rs1863993, a C>T variant in an intronic region of the DOCK2 gene (OR 3.9, p=0.0002); for the SNP rs4147385, a C>T variant in an intronic region of the MAPK9 gene (OR 2.0, p=0.0003); for the SNP rs13206518, a T>C variant in an intronic region of the MAPK9 gene (OR 0.32, p=0.00007); for the SNP rs3211834, a A>C variant in an intronic region of the CD36 gene (OR 0.56, p=0.0002); and for the SNP rs1567748, a A>C variant in an intronic region of the PTPRR gene (OR 0.51, p=0.0003).

The six SNPs that were discovered to be strongly associated with inhibitor status are significant because they are located in genes that are implicated in processes of immune and/or inflammatory response and/or modulation. In some instances, the genes of the present invention are implicated in T cell development and/or T cell responsiveness. DOCK2, or Dedicator of cytokinesis 2, is specifically expressed in hematopoietic cells. It has been shown that DOCK2 regulates T cell responsiveness through immunological synapse formation and that DOCK2 is required in T cell precursors for the development of natural killer T cells, which are important for immune regulation and host defense against pathogens (Kunisaki et al., *J. Immunol.*, 176:4640-4645 (2006)). MAPK9, also known as mitogen-activated protein kinase 9, Jun kinase 2, or stress activate protein kinase, is believed to play a key role in T cell differentiation. For example, mice deficient in Mapk9 exhibit disruption in CD4+ T cell differentiation, causing selective polarization of CD4+ T cells to the Th2 phenotype (Jaeschke et al., *Proc. Natl. Acad. Sci. USA*, 102:6931-6935 (2005); Rincón and Davis, *Immunol. Rev.*, 228:212-224 (2009)). A balance between Th1 cells (IL-1 and IFN-γ secreting cells that induce cellular immune response) and Th2 cells (IL-4, IL-5, and IL-10 secreting cells that downregulate the inflammatory activities of Th1) is critical for proper immune response, and in some autoimmune diseases there is a disruption of the Th1/Th2 balance. PTPRR, or protein tyrosine phosphatase receptor type R, is a signaling molecule that has been found to regulate MAP kinase activity, and therefore may also be implicated in regulating T cell differentiation by regulating MAPK9 activity.

In some instances, the genes described herein are implicated in inflammatory response. CD36, or cluster of differentiation 36, is a class B scavenger receptor that has been shown to regulate inflammatory signaling. For example, β-amyloid, a peptide associated with Alzheimer's disease, initiates a CD36-dependent pro-inflammatory signaling cascade in mononuclear cells (Moore et al., *J. Biol. Chem.*, 277:47373-47379 (2002)), and CD36 is required a β-amyloid-induced CD36 upregulation of the inflammatory cytokine IL-1β (El Khoury et al., *J. Exp. Med.*, 197:1657-1666 (2003)).

In some instances, the genes described herein are implicated in the blood coagulation cascade. F13A1 encodes coagulation factor XIII (FXIII) A subunit. Upon FXIII activation by thrombin, activated FXIII acts on fibrin to form crosslinks between fibrin molecules as the final step in blood clot formation. SNPs in F13A1 have been reported to be associated with other aspects blood coagulation, specifically plasma fibrinogen concentration and fibrin clot porosity (Mannila et al., *Thromb. Haemost.*, 95:420-427 (2006)).

The present invention also relates to the discovery of strong SNP associations between inhibitor development in patients with severe hemophilia and four markers within three genes. It was discovered that in the combined cohort, strong SNP associations with FVIII inhibitor status for the subgroup with severe hemophilia were observed in the DOCK2, MAPK9, and CD36 genes. For this subgroup, a strong association with inhibitor development was found for the SNP rs4147385, a C>T variant in an intronic region of the MAPK9 gene (OR 2.3, p=0.00003); for the SNP rs11744216, a C>G variant in an intronic region of the DOCK2 gene (OR 0.30, p=0.00008); for the SNP rs1863993, a C>T variant in an intronic region of the DOCK2 gene (OR 4.4, p=0.0009); and for the SNP rs3211834, a A>C variant in an intronic region of the CD36 gene (OR 0.59, p=0.0008).

In one aspect, the present invention provides a method for predicting the risk of an individual developing antibodies to factor VIII (FVIII), the method comprising the steps of identifying at least one single nucleotide polymorphism (SNP) selected from the group consisting of the SNPs listed in Table 1, and predicting the risk of the individual of developing antibodies to FVIII.

In one embodiment, the SNP is located in a gene selected from the group consisting of DOCK2, MAPK9, F13A1, CD36, and PTPRR. In one embodiment, the SNP is selected from the group consisting of rs11744216, rs13206518, rs3211834, rs1863993, rs4147385, and rs1567748.

In one embodiment, the method further comprises the steps of amplifying genomic DNA of the individual using oligonucleotide primers that amplify the SNP selected from the group consisting of the SNPS listed in Table 1, and identifying the nucleotides present at the SNP.

In one embodiment, the individual has not yet received FVIII therapy. In one embodiment, the individual has received FVIII therapy. In one embodiment, the prediction allows for adjusting a dosage of FVIII therapy received by the individual. In one embodiment, the prediction allows for providing or adjusting a dosage of bypass therapy received by the individual.

In one embodiment, the individual has severe hemophilia. In one embodiment, the individual has severe hemophilia and the SNP is located in a gene selected from the group consisting of DOCK2, MAPK9, and CD36. In one embodiment, the individual has severe hemophilia and the SNP is selected from the group consisting of rs11744216, rs1863993, rs4147385, and rs3211834.

In one embodiment, the method further comprises the steps of analyzing a sample from the individual with an assay that specifically detects the SNP selected from the group consisting of the SNPs listed in Table 1, and identifying the nucleotides present at the SNP. In one embodiment, the assay or step of identification comprises a technique selected from the group consisting of mass spectroscopy, RT-PCR, microarray hybridization, pyrosequencing, thermal cycle sequencing, capillary array sequencing, and solid phase sequencing. In one embodiment, the assay comprises microarray hybridization.

In another aspect, the present invention provides an oligonucleotide from 10 to 60 nucleotides in length that contacts at least one single nucleotide polymorphism (SNP) selected from the group consisting of the SNPs listed in Table 1. In one embodiment, the oligonucleotide contacts a SNP located in a gene selected from the group consisting of DOCK2, MAPK9, F13A1, CD36, and PTPRR. In one embodiment, the oligonucleotide contacts a SNP selected from the group consisting of rs11744216, rs13206518, rs3211834, rs1863993, rs4147385, and rs1567748. In one embodiment, the oligonucleotide is used to predict the risk of an individual developing antibodies to factor VIII (FVIII) and to adjust a dosage of FVIII therapy received by the individual. In one embodiment, the oligonucleotide is used to provide or adjust a dosage of bypass therapy received by the individual.

In another aspect, the present invention provides a diagnostic kit comprising oligonucleotides to detect at least one single nucleotide polymorphism (SNP) selected from the group consisting of the SNPs listed in Table 1. In one embodiment, the kit comprises oligonucleotides that detect a SNP located in a gene selected from the group consisting of DOCK2, MAPK9, F13A1, CD36, and PTPRR. In one embodiment, the kit comprises oligonucleotides that detect a SNP selected from the group consisting of rs11744216, rs13206518, rs3211834, rs1863993, rs4147385, and rs1567748. In one embodiment, the kit is used to predict the risk of an individual developing antibodies to factor VIII (FVIII) and to adjust a dosage of FVIII therapy received by the individual. In one embodiment, the kit is used to provide or adjust a dosage of bypass therapy received by the individual.

In yet another aspect, the present invention provides a microarray comprising a support having a plurality of discrete regions, each discrete region having a nucleic acid fragment spotted thereon, wherein the nucleic acid fragment comprises a sequence that is complementary to a single nucleotide polymorphism (SNP) selected from the group consisting of the SNPs listed in Table 1. In one embodiment, the microarray is used to predict the risk of an individual developing antibodies to factor VIII (FVIII) and to adjust a dosage of FVIII therapy received by the individual. In one embodiment, the microarray is used to provide or adjust a dosage of bypass therapy received by the individual.

In still another aspect, the present invention provides an isolated nucleic acid comprising a single nucleotide polymorphism (SNP) selected from the group consisting of the SNPs listed in Table 1. In one embodiment, the SNP is located in a gene selected from the group consisting of DOCK2, MAPK9, F13A1, CD36, and PTPRR. In one embodiment, the SNP is selected from the group consisting of rs11744216, rs13206518, rs3211834, rs1863993, rs4147385, and rs1567748.

The present invention may be understood more readily by reference to the following detailed description of specific embodiments and the Examples included therein.

II. Definitions

As used herein, the following terms have the meanings ascribed to them unless specified otherwise.

As used herein, the term "factor VIII" or "FVIII" refers to any form of factor VIII molecule with the typical characteristics of blood coagulation factor VIII, whether derived from blood plasma or produced through the use of recombinant DNA techniques, and including all modified forms of factor VIII. Factor VIII (FVIII) exists naturally and in therapeutic preparations as a heterogeneous distribution of polypeptides arising from a single gene product (see, e.g., Andersson et al., *Proc. Nati. Acad. Sci. USA*, 83:2979-2983 (1986)). Commercially available examples of therapeutic preparations containing Factor VIII include those sold under the trade names of HEMOFIL M, ADVATE, and RECOMBINATE (available from Baxter Healthcare Corporation, Deerfield, Ill., U.S.A.).

As used herein, the term "inhibitory antibodies to factor VIII" refers to antibodies that decrease or neutralize the procoagulant function of factor VIII. Inhibitory antibodies to factor VIII may develop in individuals who are not hemophiliacs, or they may develop in individuals with mild, moderate, or severe hemophilia. An individual may develop inhibitory antibodies to factor VIII prior to receiving any factor VIII therapy, or an individual may develop inhibitory antibodies to factor VIII after the onset of factor VIII therapy. In an individual receiving factor VIII therapy, inhibitory antibodies to factor VIII often appear early in the course of therapy, typically after about 9 to 11 exposure days, but sometimes develop sooner or later than 9 to 11 exposure days, within about 100 exposure days, and may develop at any time after the onset of factor VIII therapy.

As used herein, the term "single nucleotide polymorphism" or "SNP" refers to the occurrence of two or more genetically determined alternative genotypes in a population. A SNP can occur in a coding (i.e. gene) region of the genome, including the promoter region, untranslated 5' and 3' regions, introns, and coding regions found in the mRNA, or alternatively can occur in a noncoding region of the genome. In some embodiments, the SNPs associated with gene sequences of the invention may be located within 300,000; 200,000; 100,000; 75,000; 50,000; or 10,000 base pairs from the gene sequence. SNP analysis is useful for detecting differences between polynucleotide sequences, such as the sequences identified in Table 1, that are associated with increased risk of developing a disease or condition, such as developing inhibitory antibodies to FVIII. These polynucleotide sequences may occur in or near any of the genes listed in Table 1, including for example DOCK2, MAPK9, F13A1, CD36, and PTPRR. The SNPs of the present invention are useful, for instance, for predicting the risk of developing inhibitory antibodies to FVIII. For example, if an individual carries at least one SNP linked to a disease-associated allele of the gene sequences of the invention, the individual is likely at increased risk for developing inhibitory antibodies to FVIII.

It will be understood by the skilled artisan that SNPs may be used singly or in combination with other SNPs for any of the uses, e.g., predicting the risk of developing inhibitory antibodies to FVIII, disclosed herein.

As used herein, the term "gene" refers to the segment of DNA involved in producing a polypeptide chain; it includes regions preceding and following the coding region, such as the promoter and 3'-untranslated region, respectively, as well as intervening sequences (introns) between individual coding segments (exons).

As used herein, the term "oligonucleotide" refers to a nucleic acid sequence of approximately 5 nucleotides or greater in length, and up to as many as approximately 100 nucleotides in length, which can be used as a primer, probe, or amplimer. Oligonucleotides are often between about 10 and about 50 nucleotides in length, more often between about 10 and about 40 nucleotides, very often between about 15 and about 30 nucleotides, and the terms oligonucleotides or oligomers can also refer to synthetic and/or non-naturally occurring nucleic acids (i.e., comprising nucleic acid analogues or modified backbone residues or linkages)

As used herein, the term "nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).ash conditions can be utilized to provide conditions of similar stringency.

As used herein, the term "sample" includes extractions of nucleic acid such as DNA, sections of tissues such as biopsy and autopsy samples, and frozen sections taken for histological purposes. Such samples include blood and blood fractions or products (e.g., serum, buffy coat, plasma, platelets, red blood cells, and the like), sputum, cheek cells tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish.

As used herein, the terms "hemophilia" or "haemophilia" refer to a group of disease states broadly characterized by reduced blood clotting or coagulation. Hemophilia may refer to Type A, Type B, or Type C hemophilia, or to the composite of all three diseases types. Type A hemophilia (hemophilia A) is caused by a reduction or loss of factor VIII (FVIII) activity and is the most prominent of the hemophilia subtypes. Type B hemophilia (hemophilia B) results from the loss or reduction of factor IX (FIX) clotting function. Type C hemophilia (hemophilia C) is a consequence of the loss or reduction in factor XI (FXI) clotting activity. Hemophilia A and B are X-linked diseases, while hemophilia C is autosomal. Common treatments for hemophilia include both prophylactic and on-demand administration of clotting factors, such as FVIII, FIX, including Bebulin®-VH, and FXI, as well as FEIBA-VH, desmopressin, and plasma infusions.

As used herein, the term "FVIII therapy" includes any therapeutic approach of providing factor VIII to a patient to relieve, diminish, or prevent the reoccurrence of one or more symptoms (i.e., clinical factors) associated with hemophilia. The term encompasses administering any compound, drug, procedure, or regimen comprising factor VIII, including any modified form of factor VIII, which is useful for maintaining or improving the health of an individual with hemophilia and includes any of the therapeutic agents described herein. One skilled in the art will appreciate that either the course of FVIII therapy or the dose of FVIII therapy can be changed, e.g., based upon the results obtained in accordance with the present invention.

As used herein, the term "bypass therapy" includes any therapeutic approach of providing non-factor VIII hemostatic agents, compounds or coagulation factors to a patient to relieve, diminish, or prevent the reoccurrence of one or more symptoms (i.e., clinical factors) associated with hemophilia. Non-FVIII compounds and coagulation factors that may be provided include, but are not limited to, Factor VIII Inhibitor Bypass Activity (FEIBA), recombinant activated factor VII (FVIIa), prothrombin complex concentrates, and activated prothrombin complex concentrates. These non-FVIII compounds and coagulation factors may be recombinant or plasma-derived. One skilled in the art will appreciate that either the course of bypass therapy or the dose of bypass therapy can be changed, e.g., based upon the results obtained in accordance with the present invention.

As used herein, a "combination therapy comprising administration of FVIII and a FVIII bypass agent" includes any therapeutic approach of providing both Factor VIII and a non-Factor VIII hemostatic agent to a patient to relieve, diminish, or prevent the reoccurrence of one or more symptoms (i.e., clinical factors) associated with hemophilia. The term encompasses administering any compound, drug, procedure, or regimen comprising factor VIII, including any modified form of factor VIII, which is useful for maintaining or improving the health of an individual with hemophilia and includes any of the therapeutic agents described herein. Non-FVIII compounds and coagulation factors that may be provided include, but are not limited to, Factor VIII Inhibitor Bypass Activity (FEIBA), recombinant activated factor VII (FVIIa), prothrombin complex concentrates, and activated prothrombin complex concentrates. The Factor VIII and non-Factor VIII compounds and coagulation factors may be recombinant or plasma-derived.

In one embodiment, combination therapy may refer to administration of Factor VIII and a non-FVIII hemostatic agent in a single therapeutic dose. In another embodiment, combination therapy may refer to administration of Factor VIII and a non-FVIII hemostatic agent in separate therapeutic doses. For example, Factor VIII and a non-FVIII hemostatic agent may be administered in separate doses received according to a single dosage schedule, or alternatively in separate doses received according to separate dosing schedules. In one embodiment, the dosing schedules for the Factor VIII and the non-FVIII hemostatic agent may be concurrent or alternating (i.e., overlapping). In another embodiments, the dosing schedules may be non-overlapping (i.e., where one dosing regime is completed before beginning a second dosing regime with the alternate therapy). One skilled in the art will appreciate that either the course and/or dose of FVIII therapy and/or non-FVIII hemostatic agent (i.e., FVIII bypass agent) can be changed, e.g., based upon the results obtained in accordance with the present invention. In one embodiment, the identification of SNPs corresponding to one or more SNPs found in Tables 1 to 4, in a sample from a patient diagnosed with Hemophilia, will allow one of skill in the art to tailor the combination therapy (i.e., increase or decrease the regime and/or dose of one or both of the Factor VIII and FVIII bypass agent) to the individual, based on the individuals risk of developing Factor VIII inhibitors.

The terms "therapeutically effective amount or dose" or "therapeutically sufficient amount or dose" or "effective or sufficient amount or dose" refer to a dose that produces therapeutic effects for which it is administered. For example, a therapeutically effective amount of a drug useful for treating hemophilia can be the amount that is capable of preventing or relieving one or more symptoms associated with hemophilia. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, an "increased risk" of developing antibodies against Factor VIII refers to an increased probability or increased likelihood that an individual will develop antibodies against Factor VIII, for example, in response to treatment comprising administration of Factor VIII. In one embodiment, the increased risk is in comparison with an average risk of developing Factor VIII inhibitors in a given Hemophilia A population (e.g., the average risk ascribed to an individual for which SNP genotyping has not been performed. In certain embodiments, an increased risk will correspond to at least a 5% increased risk. In another embodiment, an increased risk will correspond to at least a 10% increased risk. In another embodiment, an increased risk will correspond to at least a 25% increased risk. In another embodiment, an increased risk will correspond to at least a 50% increased risk. In another embodiment, an increased risk will correspond to at least a 75% increased risk. In another embodiment, an increased risk will correspond to at least a 100% increased risk. In another embodiment, an increased risk will correspond to at least a 150% increased risk. In another embodiment, an increased risk will correspond to at least a 200% increased risk. In another embodiment, an increased risk will correspond to at least a 250% increased risk. In another embodiment, an increased risk will correspond to at least a 300% increased risk. In yet other embodiments, an increased risk will correspond to at least a 5% increased risk, or at least a 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 525%, 550%, 575%, 600%, 625%, 650%, 675%, 700%, 750%, 800%, 850%, 900%, 950%, 1000%, or greater increased risk.

As used herein, a "decreased risk" of developing antibodies against Factor VIII refers to a decreased probability or decreased likelihood that a individual will develop antibodies against Factor VIII, for example, in response to treatment comprising administration of Factor VIII. In one embodiment, the decreased risk is in comparison with a average risk of developing Factor VIII inhibitors in a given Hemophilia A population (e.g., the average risk ascribed to a individual for which SNP genotyping has not been performed). In certain embodiments, a decreased risk will correspond to at least a 5% decreased risk. In another embodiment, a decreased risk will correspond to at least a 10% decreased risk. In another embodiment, a decreased risk will correspond to at least a 25% decreased risk. In another embodiment, a decreased risk will correspond to at least a 50% decreased risk. In another embodiment, a decreased risk will correspond to at least a 75% decreased risk. In another embodiment, a decreased risk will correspond to at least a 100% decreased risk. In another embodiment, a decreased risk will correspond to at least a 150% decreased risk. In another embodiment, a decreased risk will correspond to at least a 200% decreased risk. In another embodiment, a decreased risk will correspond to at least a 250% decreased risk. In another embodiment, a decreased risk will correspond to at least a 300% decreased risk. In yet other embodiments, a decreased risk will correspond to at least a 5% decreased risk, or at least a 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 525%, 550%, 575%, 600%, 625%, 650%, 675%, 700%, 750%, 800%, 850%, 900%, 950%, 1000%, or greater decreased risk.

III. Predictive Methods and Assays

In certain aspects, the present invention provides methods for predicting the risk of an individual developing antibodies to factor VIII (FVIII). Risk prediction involves identifying at least one single nucleotide polymorphism (SNP) selected from the group consisting of the SNPs listed in Table 1, and on the basis of the nucleotides present at the SNP, determining whether the individual is more likely to develop antibodies to FVIII or not. SNP analysis is useful for detecting differences between alleles of the polynucleotides (e.g., genes) of the invention. For example, if an individual carries at least one SNP linked to a disease or condition-associated allele of the gene sequences of the invention, the individual is likely at an increased risk of developing antibodies to FVIII. In some embodiments, the SNP associated with the gene sequences of the invention is located within 300,000; 200,000; 100,000; 75,000; 50,000; or 10,000 base pairs from the gene sequence.

Predicting the risk of an individual developing antibodies to FVIII may be performed when the individual has not received any FVIII therapy. Alternatively, risk prediction may be performed soon after the individual begins receiving FVIII therapy. Alternatively, risk prediction may be performed at any time when there are suspected symptoms of FVIII antibody development in the individual. One of skill in the art will be able to identify symptoms of FVIII antibody development in the individual.

In some embodiments, the present invention provides methods of predicting the risk of an individual developing antibodies to FVIII comprising identifying a SNP located in a gene selected from the group consisting of DOCK2, MAPK9, F13A1, CD36, and PTPRR. In one embodiment, the method comprises identifying the SNP rs11744216 and determining whether the individual has a C>G polymorphism that is associated with increased risk of developing antibodies to FVIII. In one embodiment, the method comprises identifying the SNP rs13206518 and determining whether the individual has a T>C polymorphism that is associated with increased risk of developing antibodies to FVIII. In one embodiment, the method comprises identifying the SNP rs3211834 and determining whether the individual has a A>C polymorphism that is associated with increased risk of developing antibodies to FVIII. In one embodiment, the method comprises identifying the SNP rs1863993 and determining whether the individual has a C>T polymorphism that is associated with increased risk of developing antibodies to FVIII. In one embodiment, the method comprises identifying the SNP rs4147385 and determining whether the individual has a C>T polymorphism that is associated with increased risk of developing antibodies to FVIII. In one embodiment, the method comprises identifying the SNP rs1567748 and determining whether the individual has a A>C polymorphism that is associated with increased risk of developing antibodies to FVIII.

The predictive methods of the present invention may also be used to determine how to provide or adjust a dosage of therapy received by the individual. In some embodiments, the identification of a variant or condition-associated genotype for a SNP selected from the SNPs listed in Table 1 allows for adjusting a dosage of FVIII therapy received by the individual. In some embodiments, the identification of a variant or condition-associated genotype for a SNP selected from the SNPs listed in Table 1 allows for providing or adjusting a dosage of bypass therapy received by the individual.

In some embodiments of the present invention, the individual for whom the risk prediction is desired may be an individual who has severe hemophilia. In some embodiments wherein the individual for whom the risk prediction is desired has severe hemophilia, the SNP to be identified may be located in a gene selected from the group consisting of DOCK2, MAPK9, and CD36 (Table 2). In one embodiment, the individual has severe hemophilia and the method comprises identifying the SNP rs11744216 and determining whether the individual has a C>G polymorphism that is associated with increased risk of developing antibodies to FVIII. In one embodiment, the individual has severe hemophilia and the method comprises identifying the SNP rs1863993 and determining whether the individual has a C>T polymorphism that is associated with increased risk of developing antibodies to FVIII. In one embodiment, the individual has severe hemophilia and the method comprises identifying the SNP rs4147385 and determining whether the individual has a C>T polymorphism that is associated with increased risk of developing antibodies to FVIII. In one embodiment, the individual has severe hemophilia and the method comprises identifying the SNP rs3211834 and determining whether the individual has a A>C polymorphism that is associated with increased risk of developing antibodies to FVIII.

The genotype of the SNP of interest in the individual may be measured by taking a blood, saliva, urine, or other tissue sample containing nucleic acid, e.g., DNA, from the individual and analyzing the sample with an assay that specifically detects the presence of the SNP of interest. Alternatively, the genotype of the SNP of interest in the individual may be measured by taking a blood, saliva, urine, or other tissue sample from the individual and amplifying the genomic DNA of the sample using oligonucleotide primers that amplify the SNP of interest.

A. Methods for Predicting Risk in Hemophilia Patients

In one aspect, the present invention provides methods for predicting the risk of developing antibodies against Factor VIII (FVIII) in an individual diagnosed with Hemophilia A by detecting the presence of one or more of the SNPs identified herein. In one embodiment, the method comprises the steps of detecting the presence of at least one single nucleotide polymorphism (SNP) selected from the group consisting of a SNP listed in Table 1, a SNP listed in Table 2, a SNP listed in Table 3, and a SNP listed in Table 4, in a biological sample from the individual; and predicting the risk of the individual of developing antibodies to FVIII.

Generally, the predicted risk associated with each SNP is relative to the Odds ratio (OR) calculated for that particular SNP. Therefore, the detection of a SNP with an OR less than one is generally associated with a reduced likelihood (i.e., a reduced risk) of the individual developing antibodies against Factor VIII. Likewise, the detection of a SNP with an OR greater than one is generally associated with an increased likelihood (i.e., a reduced risk) of the individual developing antibodies against Factor VIII. Accordingly, treatment can then be assigned and/or administered to an individual diagnosed with Hemophilia A appropriately based on the relative risk of the individual developing antibodies against Factor VIII.

1. Individuals Diagnosed with Hemophilia A

In one embodiment, the present invention provides a method for predicting the risk of developing antibodies against Factor VIII (FVIII) in an individual diagnosed with Hemophilia A the method comprising the steps of detecting the presence of at least one single nucleotide polymorphism (SNP) selected from the group consisting of a SNP listed in Table 1, a SNP listed in Table 2, a SNP listed in Table 3, and a SNP listed in Table 4, in a biological sample from the individual; and predicting the risk of the individual of developing antibodies to FVIII.

In one embodiment of the method, the individual has been diagnosed with mild Hemophilia. In another embodiment, the individual has been diagnosed with moderate Hemophilia. In yet another embodiment, the individual has been diagnosed with severe Hemophilia.

In one embodiment of the method, the step of detecting the presence of at least one SNP comprises amplifying a nucleic acid present in the biological sample. In another embodiment, the step of detecting the presence of at least one SNP comprises a technique selected from the group consisting of mass spectroscopy, RT-PCR, microarray hybridization, pyrosequencing, thermal cycle sequencing, capillary array sequencing, solid phase sequencing, a hybridization-based method, an enzymatic-based method, a PCR-based method, a sequencing method, a ssDNA conformational method, and a DNA melting temperature assay.

In one embodiment, the method further comprises assigning and/or administering a treatment to the individual based on the predicted risk of developing antibodies against Factor VIII. In a specific embodiment, treatment comprising administration of Factor VIII is assigned to an individual with a predicted decreased risk of developing antibodies against Factor VIII. In another specific embodiment, treatment comprising Factor VIII bypass therapy is assigned to an individual with a predicted increased risk of developing antibodies against Factor VIII.

In yet another specific embodiment, combination therapy comprising administration of Factor VIII and a FVIII bypass agent is assigned to an individual based on the predicted risk of developing antibodies against Factor VIII. In one specific embodiment, a combination therapy is assigned to an individual with a predicted decreased risk of developing antibodies against Factor VIII. In another specific embodiment, a combination therapy is assigned to an individual with a predicted increased risk of developing antibodies against Factor VIII.

In one embodiment, treatment comprising administration of Factor VIII is provided to an individual with a predicted decreased risk of developing antibodies against Factor VIII. In another specific embodiment, treatment comprising Factor VIII bypass therapy is provided to an individual with a predicted increased risk of developing antibodies against Factor VIII.

In yet another embodiment, combination therapy comprising administration of Factor VIII and a FVIII bypass agent is provided to an individual based on the predicted risk of developing antibodies against Factor VIII. In one specific embodiment, a combination therapy is provided to an individual with a predicted decreased risk of developing antibodies against Factor VIII. In another specific embodiment, a combination therapy is provided to an individual with a predicted increased risk of developing antibodies against Factor VIII.

In one embodiment, the method further comprises adjusting a dosage of a treatment comprising administration of Factor VIII to the individual based on the predicted risk of developing antibodies against Factor VIII. In a specific embodiment, a dosage of Factor VIII to be administered to an individual with a predicted decreased risk of developing antibodies against Factor VIII is increased. In another specific embodiment, a dosage of Factor VIII to be administered to an individual with a predicted increased risk of developing antibodies against Factor VIII is decreased.

In another embodiment, the method further comprises adjusting the dosage and/or frequency of Factor VIII administration in a combination therapy based on the predicted risk of developing antibodies against FVIII. In one embodiment, the method comprises increasing the dosage or frequency of Factor VIII administered in a combination therapy to an individual with a predicted decreased risk of developing antibodies against Factor VIII. In another embodiment, the method comprises decreasing the dosage or frequency of Factor VIII administered in a combination therapy to an individual with a predicted increased risk of developing antibodies against Factor VIII.

In another embodiment, the method further comprises adjusting the dosage and/or frequency of a non-FVIII hemostatic agent administered in a combination therapy based on the predicted risk of developing antibodies against FVIII. In one embodiment, the method comprises increasing the dosage or frequency of a non-FVIII hemostatic agent administered in a combination therapy to an individual with a predicted increased risk of developing antibodies against Factor VIII. In another embodiment, the method comprises decreasing the dosage or frequency of a non-FVIII hemostatic agent administered in a combination therapy to an individual with a predicted decreased risk of developing antibodies against Factor VIII.

In another embodiment, the method further comprises adjusting the dosage and/or frequency of both Factor VIII and a non-FVIII hemostatic agent administered in a combination therapy based on the predicted risk of developing antibodies against FVIII. In this fashion, a combination therapy may be optimized for an individual with a specific predicted risk of developing antibodies against FVIII. Optimization of the dosage and/or frequency of Factor VIII and non-FVIII hemostatic agents in combination therapy may be achieved by any combination of increasing the frequency of FVIII administration, decreasing the frequency of FVIII administration, increasing the dosage of FVIII, decreasing the dosage of FVIII, increasing the frequency of non-FVIII hemostatic agent administration, decreasing the frequency of non-FVIII hemostatic agent administration, increasing the dosage of a non-FVIII hemostatic agent, and decreasing the dosage of a non-FVIII hemostatic agent.

In a specific embodiment, the method comprises increasing the frequency and/or dosage of FVIII and decreasing the frequency and/or dosage of a non-FVIII hemostatic agent administered to an individual with a predicted decreased risk of developing antibodies against Factor VIII.

In another specific embodiment, the method comprises decreasing the frequency and/or dosage of FVIII and increasing the frequency and/or dosage of a non-FVIII hemostatic agent administered to an individual with a predicted increased risk of developing antibodies against Factor VIII.

In a preferred embodiment, the method comprises the detection of at least one SNP selected from those listed in Table 3. In a specific embodiment, the method comprises the detection of at least on SNP selected from the group consisting of rs12368829, rs11744216, rs1863993, rs4147385, rs12546235, rs4242389, rs10054825, rs17535213, rs10072056, and rs17725712. In one embodiment, at least one detected SNP is rs12368829. In another embodiment, at least one detected SNP is rs11744216. In another embodiment, at least one detected SNP is rs1863993. In another embodiment, at least one detected SNP is rs4147385. In another embodiment, at least one detected SNP is rs12546235. In another embodiment, at least one detected SNP is rs4242389. In another embodiment, at least one detected SNP is rs10054825. In another embodiment, at least one detected SNP is rs17535213. In another embodiment, at least one detected SNP is rs10072056. In another embodiment, at least one detected SNP is rs17725712.

a) Prior to Factor VIII Therapy

In one embodiment, the present invention relates specifically to an individual or group of individuals diagnosed with Hemophilia A that have not previously received Factor VIII therapy (i.e., not received treatment comprising administration of Factor VIII).

In one embodiment, a method is provided for predicting the risk of developing antibodies against Factor VIII (FVIII) in an individual diagnosed with Hemophilia A, who has not previously received treatment comprising administration of FVIII, comprising detecting the presence of at least one single nucleotide polymorphism (SNP) selected from the group consisting of a SNP listed in Table 1, a SNP listed in Table 2, a SNP listed in Table 3, and a SNP listed in Table 4, in a biological sample from the individual; and predicting the risk of the individual of developing antibodies to FVIII.

In one embodiment of the method, the individual has been diagnosed with mild Hemophilia. In another embodiment, the individual has been diagnosed with moderate Hemophilia. In yet another embodiment, the individual has been diagnosed with severe Hemophilia.

In one embodiment of the method, the step of detecting the presence of at least one SNP comprises amplifying a nucleic acid present in the biological sample. In another embodiment, the step of detecting the presence of at least one SNP comprises a technique selected from the group consisting of mass spectroscopy, RT-PCR, microarray hybridization, pyrosequencing, thermal cycle sequencing, capillary array sequencing, solid phase sequencing, a hybridization-based method, an enzymatic-based method, a PCR-based method, a sequencing method, a ssDNA conformational method, and a DNA melting temperature assay.

In one embodiment, the method further comprises assigning and/or administering a treatment to the individual based on the predicted risk of developing antibodies against Factor VIII. In a specific embodiment, treatment comprising administration of Factor VIII is assigned to an individual with a predicted decreased risk of developing antibodies against Factor VIII. In another specific embodiment, treatment comprising Factor VIII bypass therapy is assigned to an individual with a predicted increased risk of developing antibodies against Factor VIII.

In yet another specific embodiment, combination therapy comprising administration of Factor VIII and a FVIII bypass agent is assigned to an individual based on the predicted risk of developing antibodies against Factor VIII. In one specific embodiment, a combination therapy is assigned to an individual with a predicted decreased risk of developing antibodies against Factor VIII. In another specific embodiment, a combination therapy is assigned to an individual with a predicted increased risk of developing antibodies against Factor VIII.

In one embodiment, treatment comprising administration of Factor VIII is provided to an individual with a predicted decreased risk of developing antibodies against Factor VIII. In another specific embodiment, treatment comprising Factor VIII bypass therapy is provided to an individual with a predicted increased risk of developing antibodies against Factor VIII.

In yet another embodiment, combination therapy comprising administration of Factor VIII and a FVIII bypass agent is provided to an individual based on the predicted risk of developing antibodies against Factor VIII. In one specific embodiment, a combination therapy is provided to an individual with a predicted decreased risk of developing antibodies against Factor VIII. In another specific embodiment, a combination therapy is provided to an individual with a predicted increased risk of developing antibodies against Factor VIII.

In one embodiment, the method further comprises adjusting a dosage of a treatment comprising administration of Factor VIII to the individual based on the predicted risk of developing antibodies against Factor VIII. In a specific embodiment, a dosage of Factor VIII to be administered to an individual with a predicted decreased risk of developing antibodies against Factor VIII is increased. In another specific embodiment, a dosage of Factor VIII to be administered to an individual with a predicted increased risk of developing antibodies against Factor VIII is decreased.

In another embodiment, the method further comprises adjusting the dosage and/or frequency of Factor VIII administration in a combination therapy based on the predicted risk of developing antibodies against FVIII. In one embodiment, the method comprises increasing the dosage or frequency of Factor VIII administered in a combination therapy to an individual with a predicted decreased risk of developing antibodies against Factor VIII. In another embodiment, the method comprises decreasing the dosage or frequency of Factor VIII administered in a combination therapy to an individual with a predicted increased risk of developing antibodies against Factor VIII.

In another embodiment, the method further comprises adjusting the dosage and/or frequency of a non-FVIII hemostatic agent administered in a combination therapy based on the predicted risk of developing antibodies against FVIII. In one embodiment, the method comprises increasing the dosage or frequency of a non-FVIII hemostatic agent administered in a combination therapy to an individual with a predicted increased risk of developing antibodies against Factor VIII. In another embodiment, the method comprises decreasing the dosage or frequency of a non-FVIII hemostatic agent administered in a combination therapy to an individual with a predicted decreased risk of developing antibodies against Factor VIII.

In another embodiment, the method further comprises adjusting the dosage and/or frequency of both Factor VIII and a non-FVIII hemostatic agent administered in a combination therapy based on the predicted risk of developing antibodies against FVIII. In this fashion, a combination therapy may be optimized for an individual with a specific predicted risk of developing antibodies against FVIII. Optimization of the dosage and/or frequency of Factor VIII and non-FVIII hemostatic agents in combination therapy may be achieved by any combination of increasing the frequency of FVIII administration, decreasing the frequency of FVIII administration, increasing the dosage of FVIII, decreasing the dosage of FVIII, increasing the frequency of non-FVIII hemostatic agent administration, decreasing the frequency of non-FVIII hemostatic agent administration, increasing the dosage of a non-FVIII hemostatic agent, and decreasing the dosage of a non-FVIII hemostatic agent.

In a specific embodiment, the method comprises increasing the frequency and/or dosage of FVIII and decreasing the frequency and/or dosage of a non-FVIII hemostatic agent administered to an individual with a predicted decreased risk of developing antibodies against Factor VIII.

In another specific embodiment, the method comprises decreasing the frequency and/or dosage of FVIII and increasing the frequency and/or dosage of a non-FVIII hemostatic agent administered to an individual with a predicted increased risk of developing antibodies against Factor VIII.

In a preferred embodiment, the method comprises the detection of at least one SNP selected from those listed in Table 3. In a specific embodiment, the method comprises the detection of at least on SNP selected from the group consisting of rs12368829, rs11744216, rs1863993, rs4147385, rs12546235, rs4242389, rs10054825, rs17535213, rs10072056, and rs17725712. In one embodiment, at least one detected SNP is rs12368829. In another embodiment, at least one detected SNP is rs11744216. In another embodiment, at least one detected SNP is rs1863993. In another embodiment, at least one detected SNP is rs4147385. In another embodiment, at least one detected SNP is rs12546235. In another embodiment, at least one detected SNP is rs4242389. In another embodiment, at least one detected SNP is rs10054825. In another embodiment, at least one detected SNP is rs17535213. In another embodiment, at least one detected SNP is rs10072056. In another embodiment, at least one detected SNP is rs17725712.

b) After Initial Factor VIII Therapy

In one embodiment, the present invention relates specifically to an individual or group of individuals diagnosed with Hemophilia A that have previously received Factor VIII therapy (i.e., received treatment comprising administration of Factor VIII).

In one embodiment, a method is provided for predicting the risk of developing antibodies against Factor VIII (FVIII) in an individual diagnosed with Hemophilia A, who has previously received treatment comprising administration of FVIII, comprising detecting the presence of at least one single nucleotide polymorphism (SNP) selected from the group consisting of a SNP listed in Table 1, a SNP listed in Table 2, a SNP listed in Table 3, and a SNP listed in Table 4, in a biological sample from the individual; and predicting the risk of the individual of developing antibodies to FVIII.

In one embodiment of the method, the individual has been diagnosed with mild Hemophilia. In another embodiment, the individual has been diagnosed with moderate Hemophilia. In yet another embodiment, the individual has been diagnosed with severe Hemophilia.

In one embodiment of the method, the step of detecting the presence of at least one SNP comprises amplifying a nucleic acid present in the biological sample. In another embodiment, the step of detecting the presence of at least one SNP comprises a technique selected from the group consisting of mass spectroscopy, RT-PCR, microarray hybridization, pyrosequencing, thermal cycle sequencing, capillary array sequencing, solid phase sequencing, a hybridization-based method, an enzymatic-based method, a PCR-based method, a sequencing method, a ssDNA conformational method, and a DNA melting temperature assay.

In one embodiment, the method further comprises assigning and/or administering a treatment to the individual based on the predicted risk of developing antibodies against Factor VIII. In a specific embodiment, treatment comprising administration of Factor VIII is assigned to an individual with a predicted decreased risk of developing antibodies against Factor VIII. In another specific embodiment, treatment comprising Factor VIII bypass therapy is assigned to an individual with a predicted increased risk of developing antibodies against Factor VIII.

In yet another specific embodiment, combination therapy comprising administration of Factor VIII and a FVIII bypass agent is assigned to an individual based on the predicted risk of developing antibodies against Factor VIII. In one specific embodiment, a combination therapy is assigned to an individual with a predicted decreased risk of developing antibodies against Factor VIII. In another specific embodiment, a combination therapy is assigned to an individual with a predicted increased risk of developing antibodies against Factor VIII.

In one embodiment, treatment comprising administration of Factor VIII is provided to an individual with a predicted decreased risk of developing antibodies against Factor VIII. In another specific embodiment, treatment comprising Factor VIII bypass therapy is provided to an individual with a predicted increased risk of developing antibodies against Factor VIII.

In yet another embodiment, combination therapy comprising administration of Factor VIII and a FVIII bypass agent is provided to an individual based on the predicted risk of developing antibodies against Factor VIII. In one specific embodiment, a combination therapy is provided to an individual with a predicted decreased risk of developing antibodies against Factor VIII. In another specific embodiment, a combination therapy is provided to an individual with a predicted increased risk of developing antibodies against Factor VIII.

In one embodiment, the method further comprises adjusting a dosage of a treatment comprising administration of Factor VIII to the individual based on the predicted risk of developing antibodies against Factor VIII. In a specific embodiment, a dosage of Factor VIII to be administered to an individual with a predicted decreased risk of developing antibodies against Factor VIII is increased. In another specific embodiment, a dosage of Factor VIII to be administered to an individual with a predicted increased risk of developing antibodies against Factor VIII is decreased.

In another embodiment, the method further comprises adjusting the dosage and/or frequency of Factor VIII administration in a combination therapy based on the predicted risk of developing antibodies against FVIII. In one embodiment, the method comprises increasing the dosage or frequency of Factor VIII administered in a combination therapy to an individual with a predicted decreased risk of developing antibodies against Factor VIII. In another embodiment, the method comprises decreasing the dosage or frequency of Factor VIII administered in a combination therapy to an individual with a predicted increased risk of developing antibodies against Factor VIII.

In another embodiment, the method further comprises adjusting the dosage and/or frequency of a non-FVIII hemostatic agent administered in a combination therapy based on the predicted risk of developing antibodies against FVIII. In one embodiment, the method comprises increasing the dosage or frequency of a non-FVIII hemostatic agent administered in a combination therapy to an individual with a predicted increased risk of developing antibodies against Factor VIII. In another embodiment, the method comprises decreasing the dosage or frequency of a non-FVIII hemostatic agent administered in a combination therapy to an individual with a predicted decreased risk of developing antibodies against Factor VIII.

In another embodiment, the method further comprises adjusting the dosage and/or frequency of both Factor VIII and a non-FVIII hemostatic agent administered in a combination therapy based on the predicted risk of developing antibodies against FVIII. In this fashion, a combination therapy may be optimized for an individual with a specific predicted risk of developing antibodies against FVIII. Optimization of the dosage and/or frequency of Factor VIII and non-FVIII hemostatic agents in combination therapy may be achieved by any combination of increasing the frequency of FVIII administration, decreasing the frequency of FVIII administration, increasing the dosage of FVIII, decreasing the dosage of FVIII, increasing the frequency of non-FVIII hemostatic agent administration, decreasing the frequency of non-FVIII hemostatic agent administration, increasing the dosage of a non-FVIII hemostatic agent, and decreasing the dosage of a non-FVIII hemostatic agent.

In a specific embodiment, the method comprises increasing the frequency and/or dosage of FVIII and decreasing the frequency and/or dosage of a non-FVIII hemostatic agent administered to an individual with a predicted decreased risk of developing antibodies against Factor VIII.

In another specific embodiment, the method comprises decreasing the frequency and/or dosage of FVIII and increasing the frequency and/or dosage of a non-FVIII hemostatic agent administered to an individual with a predicted increased risk of developing antibodies against Factor VIII.

In a preferred embodiment, the method comprises the detection of at least one SNP selected from those listed in Table 3. In a specific embodiment, the method comprises the detection of at least on SNP selected from the group consisting of rs12368829, rs11744216, rs1863993, rs4147385, rs12546235, rs4242389, rs10054825, rs17535213, rs10072056, and rs17725712. In one embodiment, at least one detected SNP is rs12368829. In another embodiment, at least one detected SNP is rs11744216. In another embodiment, at least one detected SNP is rs1863993. In another embodiment, at least one detected SNP is rs4147385. In another embodiment, at least one detected SNP is rs12546235. In another embodiment, at least one detected SNP is rs4242389. In another embodiment, at least one detected SNP is rs10054825. In another embodiment, at least one detected SNP is rs17535213. In another embodiment, at least one detected SNP is rs10072056. In another embodiment, at least one detected SNP is rs17725712.

2. Individuals Diagnosed with Severe Hemophilia A

In one embodiment, the present invention provides a method for predicting the risk of developing antibodies against Factor VIII (FVIII) in an individual diagnosed with severe Hemophilia A, the method comprising the steps of detecting the presence of at least one single nucleotide polymorphism (SNP) selected from the group consisting of a SNP listed in Table 2 and a SNP listed in Table 4, in a biological sample from the individual; and predicting the risk of the individual of developing antibodies to FVIII.

In one embodiment of the method, the step of detecting the presence of at least one SNP comprises amplifying a nucleic acid present in the biological sample. In another embodiment, the step of detecting the presence of at least one SNP comprises a technique selected from the group consisting of mass spectroscopy, RT-PCR, microarray hybridization, pyrosequencing, thermal cycle sequencing, capillary array sequencing, solid phase sequencing, a hybridization-based method, an enzymatic-based method, a PCR-based method, a sequencing method, a ssDNA conformational method, and a DNA melting temperature assay.

In one embodiment, the method further comprises assigning and/or administering a treatment to the individual based on the predicted risk of developing antibodies against Factor VIII. In a specific embodiment, treatment comprising administration of Factor VIII is assigned to an individual with a predicted decreased risk of developing antibodies against Factor VIII. In another specific embodiment, treatment comprising Factor VIII bypass therapy is assigned to an individual with a predicted increased risk of developing antibodies against Factor VIII.

In yet another specific embodiment, combination therapy comprising administration of Factor VIII and a FVIII bypass agent is assigned to an individual based on the predicted risk of developing antibodies against Factor VIII. In one specific embodiment, a combination therapy is assigned to an individual with a predicted decreased risk of developing antibodies against Factor VIII. In another specific embodiment, a combination therapy is assigned to an individual with a predicted increased risk of developing antibodies against Factor VIII.

In one embodiment, treatment comprising administration of Factor VIII is provided to an individual with a predicted decreased risk of developing antibodies against Factor VIII. In another specific embodiment, treatment comprising Factor VIII bypass therapy is provided to an individual with a predicted increased risk of developing antibodies against Factor VIII.

In yet another embodiment, combination therapy comprising administration of Factor VIII and a FVIII bypass agent is provided to an individual based on the predicted risk of developing antibodies against Factor VIII. In one specific embodiment, a combination therapy is provided to an individual with a predicted decreased risk of developing antibodies against Factor VIII. In another specific embodiment, a combination therapy is provided to an individual with a predicted increased risk of developing antibodies against Factor VIII.

In one embodiment, the method further comprises adjusting a dosage of a treatment comprising administration of Factor VIII to the individual based on the predicted risk of developing antibodies against Factor VIII. In a specific embodiment, a dosage of Factor VIII to be administered to an individual with a predicted decreased risk of developing antibodies against Factor VIII is increased. In another specific embodiment, a dosage of Factor VIII to be administered to an individual with a predicted increased risk of developing antibodies against Factor VIII is decreased.

In another embodiment, the method further comprises adjusting the dosage and/or frequency of Factor VIII administration in a combination therapy based on the predicted risk of developing antibodies against FVIII. In one embodiment, the method comprises increasing the dosage or frequency of Factor VIII administered in a combination therapy to an individual with a predicted decreased risk of developing antibodies against Factor VIII. In another embodiment, the method comprises decreasing the dosage or frequency of Factor VIII administered in a combination therapy to an individual with a predicted increased risk of developing antibodies against Factor VIII.

In another embodiment, the method further comprises adjusting the dosage and/or frequency of a non-FVIII hemostatic agent administered in a combination therapy based on the predicted risk of developing antibodies against FVIII. In one embodiment, the method comprises increasing the dosage or frequency of a non-FVIII hemostatic agent administered in a combination therapy to an individual with a predicted increased risk of developing antibodies against Factor VIII. In another embodiment, the method comprises decreasing the dosage or frequency of a non-FVIII hemostatic agent administered in a combination therapy to an individual with a predicted decreased risk of developing antibodies against Factor VIII.

In another embodiment, the method further comprises adjusting the dosage and/or frequency of both Factor VIII and a non-FVIII hemostatic agent administered in a combination therapy based on the predicted risk of developing antibodies against FVIII. In this fashion, a combination therapy may be optimized for an individual with a specific predicted risk of developing antibodies against FVIII. Optimization of the dosage and/or frequency of Factor VIII and non-FVIII hemostatic agents in combination therapy may be achieved by any combination of increasing the frequency of FVIII administration, decreasing the frequency of FVIII administration, increasing the dosage of FVIII, decreasing the dosage of FVIII, increasing the frequency of non-FVIII hemostatic agent administration, decreasing the frequency of non-FVIII hemostatic agent administration, increasing the dosage of a non-FVIII hemostatic agent, and decreasing the dosage of a non-FVIII hemostatic agent.

In a specific embodiment, the method comprises increasing the frequency and/or dosage of FVIII and decreasing the frequency and/or dosage of a non-FVIII hemostatic agent administered to an individual with a predicted decreased risk of developing antibodies against Factor VIII.

In another specific embodiment, the method comprises decreasing the frequency and/or dosage of FVIII and increasing the frequency and/or dosage of a non-FVIII hemostatic agent administered to an individual with a predicted increased risk of developing antibodies against Factor VIII.

In a preferred embodiment, the method comprises the detection of at least one SNP selected from those listed in Table 4. In a specific embodiment, the method comprises the detection of at least on SNP selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888. In one embodiment, at least one detected SNP is rs12368829. In another embodiment, at least one detected SNP is rs4147385. In another embodiment, at least one detected SNP is rs11744216. In another embodiment, at least one detected SNP is rs1863993. In another embodiment, at least one detected SNP is rs17535213. In another embodiment, at least one detected SNP is rs10072056. In another embodiment, at least one detected SNP is rs10054825. In another embodiment, at least one detected SNP is rs12546235. In another embodiment, at least one detected SNP is rs4242389. In another embodiment, at least one detected SNP is rs2071336. In another embodiment, at least one detected SNP is rs414634. In another embodiment, at least one detected SNP is rs17725712. In another embodiment, at least one detected SNP is rs11773821. In another embodiment, at least one detected SNP is rs8005905. In another embodiment, at least one detected SNP is rs9482888.

a) Prior to Factor VIII Therapy

In one embodiment, the present invention relates specifically to an individual or group of individuals diagnosed with severe Hemophilia A that have not previously received Factor VIII therapy (i.e., not received treatment comprising administration of Factor VIII).

In one embodiment, a method is provided for predicting the risk of developing antibodies against Factor VIII (FVIII) in an individual diagnosed with severe Hemophilia A, who has not previously received treatment comprising administration of FVIII, comprising detecting the presence of at least one single nucleotide polymorphism (SNP) selected from the group consisting of a SNP listed in Table 2 and a SNP listed in Table 4, in a biological sample from the individual; and predicting the risk of the individual of developing antibodies to FVIII.

In one embodiment of the method, the individual has been diagnosed with mild Hemophilia. In another embodiment, the individual has been diagnosed with moderate Hemophilia. In yet another embodiment, the individual has been diagnosed with severe Hemophilia.

In one embodiment of the method, the step of detecting the presence of at least one SNP comprises amplifying a nucleic acid present in the biological sample. In another embodiment, the step of detecting the presence of at least one SNP comprises a technique selected from the group consisting of mass spectroscopy, RT-PCR, microarray hybridization, pyrosequencing, thermal cycle sequencing, capillary array sequencing, solid phase sequencing, a hybridization-based method, an enzymatic-based method, a PCR-based method, a sequencing method, a ssDNA conformational method, and a DNA melting temperature assay.

In one embodiment, the method further comprises assigning and/or administering a treatment to the individual based on the predicted risk of developing antibodies against Factor VIII. In a specific embodiment, treatment comprising administration of Factor VIII is assigned to an individual with a predicted decreased risk of developing antibodies against Factor VIII. In another specific embodiment, treatment comprising Factor VIII bypass therapy is assigned to an individual with a predicted increased risk of developing antibodies against Factor VIII.

In yet another specific embodiment, combination therapy comprising administration of Factor VIII and a FVIII bypass agent is assigned to an individual based on the predicted risk of developing antibodies against Factor VIII. In one specific embodiment, a combination therapy is assigned to an individual with a predicted decreased risk of developing antibodies against Factor VIII. In another specific embodiment, a combination therapy is assigned to an individual with a predicted increased risk of developing antibodies against Factor VIII.

In one embodiment, treatment comprising administration of Factor VIII is provided to an individual with a predicted decreased risk of developing antibodies against Factor VIII. In another specific embodiment, treatment comprising Factor VIII bypass therapy is provided to an individual with a predicted increased risk of developing antibodies against Factor VIII.

In yet another embodiment, combination therapy comprising administration of Factor VIII and a FVIII bypass agent is provided to an individual based on the predicted risk of developing antibodies against Factor VIII. In one specific embodiment, a combination therapy is provided to an individual with a predicted decreased risk of developing antibodies against Factor VIII. In another specific embodiment, a combination therapy is provided to an individual with a predicted increased risk of developing antibodies against Factor VIII.

In one embodiment, the method further comprises adjusting a dosage of a treatment comprising administration of Factor VIII to the individual based on the predicted risk of developing antibodies against Factor VIII. In a specific embodiment, a dosage of Factor VIII to be administered to an individual with a predicted decreased risk of developing antibodies against Factor VIII is increased. In another specific embodiment, a dosage of Factor VIII to be administered to an individual with a predicted increased risk of developing antibodies against Factor VIII is decreased.

In another embodiment, the method further comprises adjusting the dosage and/or frequency of Factor VIII administration in a combination therapy based on the predicted risk of developing antibodies against FVIII. In one embodiment, the method comprises increasing the dosage or frequency of Factor VIII administered in a combination therapy to an individual with a predicted decreased risk of developing antibodies against Factor VIII. In another embodiment, the method comprises decreasing the dosage or frequency of Factor VIII administered in a combination therapy to an individual with a predicted increased risk of developing antibodies against Factor VIII.

In another embodiment, the method further comprises adjusting the dosage and/or frequency of a non-FVIII hemostatic agent administered in a combination therapy based on the predicted risk of developing antibodies against FVIII. In one embodiment, the method comprises increasing the dosage or frequency of a non-FVIII hemostatic agent administered in a combination therapy to an individual with a predicted increased risk of developing antibodies against Factor VIII. In another embodiment, the method comprises decreasing the dosage or frequency of a non-FVIII hemostatic agent administered in a combination therapy to an individual with a predicted decreased risk of developing antibodies against Factor VIII.

In another embodiment, the method further comprises adjusting the dosage and/or frequency of both Factor VIII and a non-FVIII hemostatic agent administered in a combination therapy based on the predicted risk of developing antibodies against FVIII. In this fashion, a combination therapy may be optimized for an individual with a specific predicted risk of developing antibodies against FVIII. Optimization of the dosage and/or frequency of Factor VIII and non-FVIII hemostatic agents in combination therapy may be achieved by any combination of increasing the frequency of FVIII administration, decreasing the frequency of FVIII administration, increasing the dosage of FVIII, decreasing the dosage of FVIII, increasing the frequency of non-FVIII hemostatic agent administration, decreasing the frequency of non-FVIII hemostatic agent administration, increasing the dosage of a non-FVIII hemostatic agent, and decreasing the dosage of a non-FVIII hemostatic agent.

In a specific embodiment, the method comprises increasing the frequency and/or dosage of FVIII and decreasing the frequency and/or dosage of a non-FVIII hemostatic agent administered to an individual with a predicted decreased risk of developing antibodies against Factor VIII.

In another specific embodiment, the method comprises decreasing the frequency and/or dosage of FVIII and increasing the frequency and/or dosage of a non-FVIII hemostatic agent administered to an individual with a predicted increased risk of developing antibodies against Factor VIII.

In a preferred embodiment, the method comprises the detection of at least one SNP selected from those listed in Table 4. In a specific embodiment, the method comprises the detection of at least on SNP selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888. In one embodiment, at least one detected SNP is rs12368829. In another embodiment, at least one detected SNP is rs4147385. In another embodiment, at least one detected SNP is rs11744216. In another embodiment, at least one detected SNP is rs1863993. In another embodiment, at least one detected SNP is rs17535213. In another embodiment, at least one detected SNP is rs10072056. In another embodiment, at least one detected SNP is rs10054825. In another embodiment, at least one detected SNP is rs12546235. In another embodiment, at least one detected SNP is rs4242389. In another embodiment, at least one detected SNP is rs2071336. In another embodiment, at least one detected SNP is rs414634. In another embodiment, at least one detected SNP is rs17725712. In another embodiment, at least one detected SNP is rs11773821. In another embodiment, at least one detected SNP is rs8005905. In another embodiment, at least one detected SNP is rs9482888.

b) After Initial Factor VIII Therapy

In one embodiment, the present invention relates specifically to an individual or group of individuals diagnosed with severe Hemophilia A that have previously received Factor VIII therapy (i.e., received treatment comprising administration of Factor VIII).

In one embodiment, a method is provided for predicting the risk of developing antibodies against Factor VIII (FVIII) in an individual diagnosed with severe Hemophilia A, who has previously received treatment comprising administration of FVIII, comprising detecting the presence of at least one single nucleotide polymorphism (SNP) selected from the group consisting of a SNP listed in Table 2 and a SNP listed in Table 4, in a biological sample from the individual; and predicting the risk of the individual of developing antibodies to FVIII.

In one embodiment of the method, the individual has been diagnosed with mild Hemophilia. In another embodiment, the individual has been diagnosed with moderate Hemophilia. In yet another embodiment, the individual has been diagnosed with severe Hemophilia.

In one embodiment of the method, the step of detecting the presence of at least one SNP comprises amplifying a nucleic acid present in the biological sample. In another embodiment, the step of detecting the presence of at least one SNP comprises a technique selected from the group consisting of mass spectroscopy, RT-PCR, microarray hybridization, pyrosequencing, thermal cycle sequencing, capillary array sequencing, solid phase sequencing, a hybridization-based method, an enzymatic-based method, a PCR-based method, a sequencing method, a ssDNA conformational method, and a DNA melting temperature assay.

In one embodiment, the method further comprises assigning and/or administering a treatment to the individual based on the predicted risk of developing antibodies against Factor VIII. In a specific embodiment, treatment comprising administration of Factor VIII is assigned to an individual with a predicted decreased risk of developing antibodies against Factor VIII. In another specific embodiment, treatment comprising Factor VIII bypass therapy is assigned to an individual with a predicted increased risk of developing antibodies against Factor VIII.

In yet another specific embodiment, combination therapy comprising administration of Factor VIII and a FVIII bypass agent is assigned to an individual based on the predicted risk of developing antibodies against Factor VIII. In one specific embodiment, a combination therapy is assigned to an individual with a predicted decreased risk of developing antibodies against Factor VIII. In another specific embodiment, a combination therapy is assigned to an individual with a predicted increased risk of developing antibodies against Factor VIII.

In one embodiment, treatment comprising administration of Factor VIII is provided to an individual with a predicted decreased risk of developing antibodies against Factor VIII. In another specific embodiment, treatment comprising Factor VIII bypass therapy is provided to an individual with a predicted increased risk of developing antibodies against Factor VIII.

In yet another embodiment, combination therapy comprising administration of Factor VIII and a FVIII bypass agent is provided to an individual based on the predicted risk of developing antibodies against Factor VIII. In one specific embodiment, a combination therapy is provided to an individual with a predicted decreased risk of developing antibodies against Factor VIII. In another specific embodiment, a combination therapy is provided to an individual with a predicted increased risk of developing antibodies against Factor VIII.

In one embodiment, the method further comprises adjusting a dosage of a treatment comprising administration of Factor VIII to the individual based on the predicted risk of developing antibodies against Factor VIII. In a specific embodiment, a dosage of Factor VIII to be administered to an individual with a predicted decreased risk of developing antibodies against Factor VIII is increased. In another specific embodiment, a dosage of Factor VIII to be administered to an individual with a predicted increased risk of developing antibodies against Factor VIII is decreased.

In another embodiment, the method further comprises adjusting the dosage and/or frequency of Factor VIII administration in a combination therapy based on the predicted risk of developing antibodies against FVIII. In one embodiment, the method comprises increasing the dosage or frequency of Factor VIII administered in a combination therapy to an individual with a predicted decreased risk of developing antibodies against Factor VIII. In another embodiment, the method comprises decreasing the dosage or frequency of Factor VIII administered in a combination therapy to an individual with a predicted increased risk of developing antibodies against Factor VIII.

In another embodiment, the method further comprises adjusting the dosage and/or frequency of a non-FVIII hemostatic agent administered in a combination therapy based on the predicted risk of developing antibodies against FVIII. In one embodiment, the method comprises increasing the dosage or frequency of a non-FVIII hemostatic agent administered in a combination therapy to an individual with a predicted increased risk of developing antibodies against Factor VIII. In another embodiment, the method comprises decreasing the dosage or frequency of a non-FVIII hemostatic agent administered in a combination therapy to an individual with a predicted decreased risk of developing antibodies against Factor VIII.

In another embodiment, the method further comprises adjusting the dosage and/or frequency of both Factor VIII and a non-FVIII hemostatic agent administered in a combination therapy based on the predicted risk of developing antibodies against FVIII. In this fashion, a combination therapy may be optimized for an individual with a specific predicted risk of developing antibodies against FVIII. Optimization of the dosage and/or frequency of Factor VIII and non-FVIII hemostatic agents in combination therapy may be achieved by any combination of increasing the frequency of FVIII administration, decreasing the frequency of FVIII administration, increasing the dosage of FVIII, decreasing the dosage of FVIII, increasing the frequency of non-FVIII hemostatic agent administration, decreasing the frequency of non-FVIII hemostatic agent administration, increasing the dosage of a non-FVIII hemostatic agent, and decreasing the dosage of a non-FVIII hemostatic agent.

In a specific embodiment, the method comprises increasing the frequency and/or dosage of FVIII and decreasing the frequency and/or dosage of a non-FVIII hemostatic agent administered to an individual with a predicted decreased risk of developing antibodies against Factor VIII.

In another specific embodiment, the method comprises decreasing the frequency and/or dosage of FVIII and increasing the frequency and/or dosage of a non-FVIII hemostatic agent administered to an individual with a predicted increased risk of developing antibodies against Factor VIII.

In a preferred embodiment, the method comprises the detection of at least one SNP selected from those listed in Table 4. In a specific embodiment, the method comprises the detection of at least on SNP selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888. In one embodiment, at least one detected SNP is rs12368829. In another embodiment, at least one detected SNP is rs4147385. In another embodiment, at least one detected SNP is rs11744216. In another embodiment, at least one detected SNP is rs1863993. In another embodiment, at least one detected SNP is rs17535213. In another embodiment, at least one detected SNP is rs10072056. In another embodiment, at least one detected SNP is rs10054825. In another embodiment, at least one detected SNP is rs12546235. In another embodiment, at least one detected SNP is rs4242389. In another embodiment, at least one detected SNP is rs2071336. In another embodiment, at least one detected SNP is rs414634. In another embodiment, at least one detected SNP is rs17725712. In another embodiment, at least one detected SNP is rs11773821. In another embodiment, at least one detected SNP is rs8005905. In another embodiment, at least one detected SNP is rs9482888.

B. Predictive Markers

Among other aspects, the present invention provides novel markers consisting of SNPs for predicting the risk of developing antibodies against Factor VIII (FVIII) in an individual diagnosed with Hemophilia A. Any individual SNP provided in Tables 1 to 4 may be used in conjunction with any other individual SNP provided in Tables 1 to 4 in the methods provided herein for the risk of developing antibodies against Factor VIII (FVIII) in an individual diagnosed with Hemophilia A.

As such, the present invention contemplates methods for detecting the identity of the nucleotide corresponding to the genomic position of any single SNP listed in Tables 1 to 4 in a biological sample from an individual diagnosed with Hemophilia A. In another embodiment, the method comprises detecting the identity of the nucleotide corresponding to the genomic position of at least 2 SNPs listed in Tables 1 to 4 in a sample from an individual diagnosed with Hemophilia A. In yet other embodiments, methods are provided for detecting the identity of the nucleotide corresponding to the genomic position of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, more, or all of the SNPs listed in Tables 1 to 4.

In a related embodiment, the present invention contemplates methods for detecting the presence of any SNP listed in Tables 1 to 4 in a biological sample from an individual diagnosed with Hemophilia A. In another embodiment, the method comprises detecting the presence of at least 2 SNPs listed in Tables 1 to 4 in a sample from an individual diagnosed with Hemophilia A. In yet other embodiments, methods are provided for detecting the presence of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, more, or all of the SNPs listed in Tables 1 to 4. Generally, detecting the presence of at least one SNP in a biological sample from an individual diagnosed with Hemophilia A may comprise detecting the identity of the nucleotide corresponding to the genomic position of multiple SNPs listed in Tables 1 to 4.

In certain embodiments, these SNPs may be used in conjunction with other markers known in the art as useful to help predict the risk of developing antibodies against Factor VIII (FVIII) in an individual diagnosed with Hemophilia A. Non-limiting examples of other markers include, various epitopes and allelic variations of the Factor VIII gene and gene product (see, Millar D S et al., *Hum Genet.* 1990 December; 86(2):219-27; Kazazian H H Jr et al., *Nature* 1988 Mar. 10; 332(6160):164-6; and Ostertag E M et al., *Annu Rev Genet.* 2001; 35:501-38, the disclosures of which are hereby incorporated by reference in their entireties for all purposes).

Genomic information regarding the SNPs listed in Tables 1 to 4 can be obtained from the ENTREZ SNP database accessible via the website for the National Center for Biotechnology Information (NCBI). For example, as can be found on the server mentioned above, SNP rs12368829 corresponds to an A/G single nucleotide polymorphism (SNP) at position 94,473,201 of human chromosome 12 according to build 37.1 of the Celera whole genome sequence. The sequence flanking the SNP comprises the following sequence, with the SNP position underlined in brackets: TTGCCACTACTTGTCTCCAAAGAAAC [A/G]TAAGAATGCTTTATCATACAACAGT (SEQ ID NO:1). Based on the sequence information provided by the NCBI server, one of skill in the art will readily be able to determine the identity of the nucleotide at a position corresponding to any one of the SNPs listed in Tables 1 to 4 in a biological sample from an individual diagnosed with Hemophilia A. Accordingly, Applicants hereby incorporate the information provided on the NCBI server for each of the SNPs listed in Tables 1 to 4 into the present application in its entirety for all purposes.

In one embodiment, the present invention provides a marker useful for predicting the risk of developing antibodies against FVIII in an individual diagnosed with Hemophilia A consisting of SNP rs1003854. In one embodiment, a method is provided for predicting the risk of developing antibodies against FVIII in an individual diagnosed with Hemophilia A comprising the steps of detecting the presence SNP rs1003854 in a biological sample from the individual; and predicting the risk of the individual of developing antibodies to FVIII. In one embodiment, the presence of SNP rs1003854 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10054825. In one embodiment, a method is provided for predicting the risk of developing antibodies against FVIII in an individual diagnosed with Hemophilia A comprising the steps of detecting the presence SNP rs10054825 in a biological sample from the individual; and predicting the risk of the individual of developing antibodies to FVIII. In one embodiment, the presence of SNP rs10054825 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10072056. In one embodiment, a method is provided for predicting the risk of developing antibodies against FVIII in an individual diagnosed with Hemophilia A comprising the steps of detecting the presence SNP rs10072056 in a biological sample from the individual; and predicting the risk of the individual of developing antibodies to FVIII. In one embodiment, the presence of SNP rs10072056 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1007212. In one embodiment, a method is provided for predicting the risk of developing antibodies against FVIII in an individual diagnosed with Hemophilia A comprising the steps of detecting the presence SNP rs1007212 in a biological sample from the individual; and predicting the risk of the individual of developing antibodies to FVIII. In one embodiment, the presence of SNP rs1007212 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10074391. In one embodiment, a method is provided for predicting the risk of developing antibodies against FVIII in an individual diagnosed with Hemophilia A comprising the steps of detecting the presence SNP rs10074391 in a biological sample from the individual; and predicting the risk of the individual of developing antibodies to FVIII. In one embodiment, the presence of SNP rs10074391 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1007822. In one embodiment, a method is provided for predicting the risk of developing antibodies against FVIII in an individual diagnosed with Hemophilia A comprising the steps of detecting the presence SNP rs1007822 in a biological sample from the individual; and predicting the risk of the individual of developing antibodies to FVIII. In one embodiment, the presence of SNP rs1007822 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10104302. In one embodiment, a method is provided for predicting the risk of developing antibodies against FVIII in an individual diagnosed with Hemophilia A comprising the steps of detecting the presence SNP rs10104302 in a biological sample from the individual; and predicting the risk of the individual of developing antibodies to FVIII. In one embodiment, the presence of SNP rs10104302 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10165797. In one embodiment, a method is provided for predicting the risk of developing antibodies against FVIII in an individual diagnosed with Hemophilia A comprising the steps of detecting the presence SNP rs10165797 in a biological sample from the individual; and predicting the risk of the individual of developing antibodies to FVIII. In one embodiment, the presence of SNP rs10165797 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10261447. In one embodiment, a method is provided for predicting the risk of developing antibodies against FVIII in an individual diagnosed with Hemophilia A comprising the steps of detecting the presence SNP rs10261447 in a biological sample from the individual; and predicting the risk of the individual of developing antibodies to FVIII. In one embodiment, the presence of SNP rs10261447 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10406354. In one embodiment, a method is provided for predicting the risk of developing antibodies against FVIII in an individual diagnosed with Hemophilia A comprising the steps of detecting the presence SNP rs10406354 in a biological sample from the individual; and predicting the risk of the individual of developing antibodies to FVIII. In one embodiment, the presence of SNP rs10406354 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1041067. In one embodiment, a method is provided for predicting the risk of developing antibodies against FVIII in an individual diagnosed with Hemophilia A comprising the steps of detecting the presence SNP rs1041067 in a biological sample from the individual; and predicting the risk of the individual of developing antibodies to FVIII. In one embodiment, the presence of SNP rs1041067 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1044141. In one embodiment, a method is provided for predicting the risk of developing antibodies against FVIII in an individual diagnosed with Hemophilia A comprising the steps of detecting the presence SNP rs1044141 in a biological sample from the individual; and predicting the risk of the individual of developing antibodies to FVIII. In one embodiment, the presence of SNP rs1044141 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1046780. In one embodiment, a method is provided for predicting the risk of developing antibodies against FVIII in an individual diagnosed with Hemophilia A comprising the steps of detecting the presence SNP rs1046780 in a biological sample from the individual; and predicting the risk of the individual of developing antibodies to FVIII. In one embodiment, the presence of SNP rs1046780 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10497208. In one embodiment, a method is provided for predicting the risk of developing antibodies against FVIII in an individual diagnosed with Hemophilia A comprising the steps of detecting the presence SNP rs10497208 in a biological sample from the individual; and predicting the risk of the individual of developing antibodies to FVIII. In one embodiment, the presence of SNP rs10497208 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1050382. In one embodiment, a method is provided for predicting the risk of developing antibodies against FVIII in an individual diagnosed with Hemophilia A comprising the steps of detecting the presence SNP rs1050382 in a biological sample from the individual; and predicting the risk of the individual of developing antibodies to FVIII. In one embodiment, the presence of SNP rs1050382 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10514071. In one embodiment, a method is provided for predicting the risk of developing antibodies against FVIII in an individual diagnosed with Hemophilia A comprising the steps of detecting the presence SNP rs10514071 in a biological sample from the individual; and predicting the risk of the individual of developing antibodies to FVIII. In one embodiment, the presence of SNP rs10514071 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1058240. In one embodiment, a method is provided for predicting the risk of developing antibodies against FVIII in an individual diagnosed with Hemophilia A comprising the steps of detecting the presence SNP rs1058240 in a biological sample from the individual; and predicting the risk of the individual of developing antibodies to FVIII. In one embodiment, the presence of SNP rs1058240 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1062069. In one embodiment, a method is provided for predicting the risk of developing antibodies against FVIII in an individual diagnosed with Hemophilia A comprising the steps of detecting the presence SNP rs1062069 in a biological sample from the individual; and predicting the risk of the individual of developing antibodies to FVIII. In one embodiment, the presence of SNP rs1062069 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1075846. In one embodiment, a method is provided for predicting the risk of developing antibodies against FVIII in an individual diagnosed with Hemophilia A comprising the steps of detecting the presence SNP rs1075846 in a biological sample from the individual; and predicting the risk of the individual of developing antibodies to FVIII. In one embodiment, the presence of SNP rs1075846 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10772120. In one embodiment, a method is provided for predicting the risk of developing antibodies against FVIII in an individual diagnosed with Hemophilia A comprising the steps of detecting the presence SNP rs10772120 in a biological sample from the individual; and predicting the risk of the individual of developing antibodies to FVIII. In one embodiment, the presence of SNP rs10772120 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10789841. In one embodiment, a method is provided for predicting the risk of developing antibodies against FVIII in an individual diagnosed with Hemophilia A comprising the steps of detecting the presence SNP rs10789841 in a biological sample from the individual; and predicting the risk of the individual of developing antibodies to FVIII. In one embodiment, the presence of SNP rs10789841 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10797666. In one embodiment, a method is provided for predicting the risk of developing antibodies against FVIII in an individual diagnosed with Hemophilia A comprising the steps of detecting the presence SNP rs10797666 in a biological sample from the individual; and predicting the risk of the individual of developing antibodies to FVIII. In one embodiment, the presence of SNP rs10797666 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10807350. In one embodiment, a method is provided for predicting the risk of developing antibodies against FVIII in an individual diagnosed with Hemophilia A comprising the steps of detecting the presence SNP rs10807350 in a biological sample from the individual; and predicting the risk of the individual of developing antibodies to FVIII. In one embodiment, the presence of SNP rs10807350 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10836342. In one embodiment, a method is provided for predicting the risk of developing antibodies against FVIII in an individual diagnosed with Hemophilia A comprising the steps of detecting the presence SNP rs10836342 in a biological sample from the individual; and predicting the risk of the individual of developing antibodies to FVIII. In one embodiment, the presence of SNP rs10836342 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10854166. In one embodiment, a method is provided for predicting the risk of developing antibodies against FVIII in an individual diagnosed with Hemophilia A comprising the steps of detecting the presence SNP rs10854166 in a biological sample from the individual; and predicting the risk of the individual of developing antibodies to FVIII. In one embodiment, the presence of SNP rs10854166 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10972149. In one embodiment, a method is provided for predicting the risk of developing antibodies against FVIII in an individual diagnosed with Hemophilia A comprising the steps of detecting the presence SNP rs10972149 in a biological sample from the individual; and predicting the risk of the individual of developing antibodies to FVIII. In one embodiment, the presence of SNP rs10972149 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs10977434. In one embodiment, a method is provided for predicting the risk of developing antibodies against FVIII in an individual diagnosed with Hemophilia A comprising the steps of detecting the presence SNP rs10977434 in a biological sample from the individual; and predicting the risk of the individual of developing antibodies to FVIII. In one embodiment, the presence of SNP rs10977434 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11015985. In one embodiment, a method is provided for predicting the risk of developing antibodies against FVIII in an individual diagnosed with Hemophilia A comprising the steps of detecting the presence SNP rs11015985 in a biological sample from the individual; and predicting the risk of the individual of developing antibodies to FVIII. In one embodiment, the presence of SNP rs11015985 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11032349. In one embodiment, a method is provided for predicting the risk of developing antibodies against FVIII in an individual diagnosed with Hemophilia A comprising the steps of detecting the presence SNP rs11032349 in a biological sample from the individual; and predicting the risk of the individual of developing antibodies to FVIII. In one embodiment, the presence of SNP rs11032349 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1105238. In one embodiment, a method is provided for predicting the risk of developing antibodies against FVIII in an individual diagnosed with Hemophilia A comprising the steps of detecting the presence SNP rs1105238 in a biological sample from the individual; and predicting the risk of the individual of developing antibodies to FVIII. In one embodiment, the presence of SNP rs1105238 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11168267. In one embodiment, a method is provided for predicting the risk of developing antibodies against FVIII in an individual diagnosed with Hemophilia A comprising the steps of detecting the presence SNP rs11168267 in a biological sample from the individual; and predicting the risk of the individual of developing antibodies to FVIII. In one embodiment, the presence of SNP rs11168267 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11214108. In one embodiment, a method is provided for predicting the risk of developing antibodies against FVIII in an individual diagnosed with Hemophilia A comprising the steps of detecting the presence SNP rs11214108 in a biological sample from the individual; and predicting the risk of the individual of developing antibodies to FVIII. In one embodiment, the presence of SNP rs11214108 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11237451. In one embodiment, a method is provided for predicting the risk of developing antibodies against FVIII in an individual diagnosed with Hemophilia A comprising the steps of detecting the presence SNP rs11237451 in a biological sample from the individual; and predicting the risk of the individual of developing antibodies to FVIII. In one embodiment, the presence of SNP rs11237451 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11265416. In one embodiment, a method is provided for predicting the risk of developing antibodies against FVIII in an individual diagnosed with Hemophilia A comprising the steps of detecting the presence SNP rs11265416 in a biological sample from the individual; and predicting the risk of the individual of developing antibodies to FVIII. In one embodiment, the presence of SNP rs11265416 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1131510. In one embodiment, a method is provided for predicting the risk of developing antibodies against FVIII in an individual diagnosed with Hemophilia A comprising the steps of detecting the presence SNP rs1131510 in a biological sample from the individual; and predicting the risk of the individual of developing antibodies to FVIII. In one embodiment, the presence of SNP rs1131510 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11574113. In one embodiment, a method is provided for predicting the risk of developing antibodies against FVIII in an individual diagnosed with Hemophilia A comprising the steps of detecting the presence SNP rs11574113 in a biological sample from the individual; and predicting the risk of the individual of developing antibodies to FVIII. In one embodiment, the presence of SNP rs11574113 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11740298. In one embodiment, a method is provided for predicting the risk of developing antibodies against FVIII in an individual diagnosed with Hemophilia A comprising the steps of detecting the presence SNP rs11740298 in a biological sample from the individual; and predicting the risk of the individual of developing antibodies to FVIII. In one embodiment, the presence of SNP rs11740298 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11744216. In one embodiment, a method is provided for predicting the risk of developing antibodies against FVIII in an individual diagnosed with Hemophilia A comprising the steps of detecting the presence SNP rs11744216 in a biological sample from the individual; and predicting the risk of the individual of developing antibodies to FVIII. In one embodiment, the presence of SNP rs11744216 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11773821. In one embodiment, a method is provided for predicting the risk of developing antibodies against FVIII in an individual diagnosed with Hemophilia A comprising the steps of detecting the presence SNP rs11773821 in a biological sample from the individual; and predicting the risk of the individual of developing antibodies to FVIII. In one embodiment, the presence of SNP rs11773821 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11780679. In one embodiment, a method is provided for predicting the risk of developing antibodies against FVIII in an individual diagnosed with Hemophilia A comprising the steps of detecting the presence SNP rs11780679 in a biological sample from the individual; and predicting the risk of the individual of developing antibodies to FVIII. In one embodiment, the presence of SNP rs11780679 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11833550. In one embodiment, a method is provided for predicting the risk of developing antibodies against FVIII in an individual diagnosed with Hemophilia A comprising the steps of detecting the presence SNP rs11833550 in a biological sample from the individual; and predicting the risk of the individual of developing antibodies to FVIII. In one embodiment, the presence of SNP rs11833550 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11852361. In one embodiment, a method is provided for predicting the risk of developing antibodies against FVIII in an individual diagnosed with Hemophilia A comprising the steps of detecting the presence SNP rs11852361 in a biological sample from the individual; and predicting the risk of the individual of developing antibodies to FVIII. In one embodiment, the presence of SNP rs11852361 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs11952962. In one embodiment, a method is provided for predicting the risk of developing antibodies against FVIII in an individual diagnosed with Hemophilia A comprising the steps of detecting the presence SNP rs11952962 in a biological sample from the individual; and predicting the risk of the individual of developing antibodies to FVIII. In one embodiment, the presence of SNP rs11952962 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12001295. In one embodiment, a method is provided for predicting the risk of developing antibodies against FVIII in an individual diagnosed with Hemophilia A comprising the steps of detecting the presence SNP rs12001295 in a biological sample from the individual; and predicting the risk of the individual of developing antibodies to FVIII. In one embodiment, the presence of SNP rs12001295 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12034383. In one embodiment, a method is provided for predicting the risk of developing antibodies against FVIII in an individual diagnosed with Hemophilia A comprising the steps of detecting the presence SNP rs12034383 in a biological sample from the individual; and predicting the risk of the individual of developing antibodies to FVIII. In one embodiment, the presence of SNP rs12034383 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12039194. In one embodiment, a method is provided for predicting the risk of developing antibodies against FVIII in an individual diagnosed with Hemophilia A comprising the steps of detecting the presence SNP rs12039194 in a biological sample from the individual; and predicting the risk of the individual of developing antibodies to FVIII. In one embodiment, the presence of SNP rs12039194 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12051769. In one embodiment, a method is provided for predicting the risk of developing antibodies against FVIII in an individual diagnosed with Hemophilia A comprising the steps of detecting the presence SNP rs12051769 in a biological sample from the individual; and predicting the risk of the individual of developing antibodies to FVIII. In one embodiment, the presence of SNP rs12051769 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1206486. In one embodiment, a method is provided for predicting the risk of developing antibodies against FVIII in an individual diagnosed with Hemophilia A comprising the steps of detecting the presence SNP rs1206486 in a biological sample from the individual; and predicting the risk of the individual of developing antibodies to FVIII. In one embodiment, the presence of SNP rs1206486 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12185980. In one embodiment, a method is provided for predicting the risk of developing antibodies against FVIII in an individual diagnosed with Hemophilia A comprising the steps of detecting the presence SNP rs12185980 in a biological sample from the individual; and predicting the risk of the individual of developing antibodies to FVIII. In one embodiment, the presence of SNP rs12185980 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12310405. In one embodiment, a method is provided for predicting the risk of developing antibodies against FVIII in an individual diagnosed with Hemophilia A comprising the steps of detecting the presence SNP rs12310405 in a biological sample from the individual; and predicting the risk of the individual of developing antibodies to FVIII. In one embodiment, the presence of SNP rs12310405 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12325842. In one embodiment, a method is provided for predicting the risk of developing antibodies against FVIII in an individual diagnosed with Hemophilia A comprising the steps of detecting the presence SNP rs12325842 in a biological sample from the individual; and predicting the risk of the individual of developing antibodies to FVIII. In one embodiment, the presence of SNP rs12325842 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12368829. In one embodiment, a method is provided for predicting the risk of developing antibodies against FVIII in an individual diagnosed with Hemophilia A comprising the steps of detecting the presence SNP rs12368829 in a biological sample from the individual; and predicting the risk of the individual of developing antibodies to FVIII. In one embodiment, the presence of SNP rs12368829 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12451415. In one embodiment, a method is provided for predicting the risk of developing antibodies against FVIII in an individual diagnosed with Hemophilia A comprising the steps of detecting the presence SNP rs12451415 in a biological sample from the individual; and predicting the risk of the individual of developing antibodies to FVIII. In one embodiment, the presence of SNP rs12451415 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12506181. In one embodiment, a method is provided for predicting the risk of developing antibodies against FVIII in an individual diagnosed with Hemophilia A comprising the steps of detecting the presence SNP rs12506181 in a biological sample from the individual; and predicting the risk of the individual of developing antibodies to FVIII. In one embodiment, the presence of SNP rs12506181 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12546235. In one embodiment, a method is provided for predicting the risk of developing antibodies against FVIII in an individual diagnosed with Hemophilia A comprising the steps of detecting the presence SNP rs12546235 in a biological sample from the individual; and predicting the risk of the individual of developing antibodies to FVIII. In one embodiment, the presence of SNP rs12546235 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12546235. In one embodiment, a method is provided for predicting the risk of developing antibodies against FVIII in an individual diagnosed with Hemophilia A comprising the steps of detecting the presence SNP rs12546235 in a biological sample from the individual; and predicting the risk of the individual of developing antibodies to FVIII. In one embodiment, the presence of SNP rs12546235 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12625871. In one embodiment, a method is provided for predicting the risk of developing antibodies against FVIII in an individual diagnosed with Hemophilia A comprising the steps of detecting the presence SNP rs12625871 in a biological sample from the individual; and predicting the risk of the individual of developing antibodies to FVIII. In one embodiment, the presence of SNP rs12625871 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1264456. In one embodiment, a method is provided for predicting the risk of developing antibodies against FVIII in an individual diagnosed with Hemophilia A comprising the steps of detecting the presence SNP rs1264456 in a biological sample from the individual; and predicting the risk of the individual of developing antibodies to FVIII. In one embodiment, the presence of SNP rs1264456 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12667537. In one embodiment, a method is provided for predicting the risk of developing antibodies against FVIII in an individual diagnosed with Hemophilia A comprising the steps of detecting the presence SNP rs12667537 in a biological sample from the individual; and predicting the risk of the individual of developing antibodies to FVIII. In one embodiment, the presence of SNP rs12667537 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1267843. In one embodiment, a method is provided for predicting the risk of developing antibodies against FVIII in an individual diagnosed with Hemophilia A comprising the steps of detecting the presence SNP rs1267843 in a biological sample from the individual; and predicting the risk of the individual of developing antibodies to FVIII. In one embodiment, the presence of SNP rs1267843 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12692566. In one embodiment, a method is provided for predicting the risk of developing antibodies against FVIII in an individual diagnosed with Hemophilia A comprising the steps of detecting the presence SNP rs12692566 in a biological sample from the individual; and predicting the risk of the individual of developing antibodies to FVIII. In one embodiment, the presence of SNP rs12692566 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12810163. In one embodiment, a method is provided for predicting the risk of developing antibodies against FVIII in an individual diagnosed with Hemophilia A comprising the steps of detecting the presence SNP rs12810163 in a biological sample from the individual; and predicting the risk of the individual of developing antibodies to FVIII. In one embodiment, the presence of SNP rs12810163 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12814009. In one embodiment, a method is provided for predicting the risk of developing antibodies against FVIII in an individual diagnosed with Hemophilia A comprising the steps of detecting the presence SNP rs12814009 in a biological sample from the individual; and predicting the risk of the individual of developing antibodies to FVIII. In one embodiment, the presence of SNP rs12814009 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12831813. In one embodiment, a method is provided for predicting the risk of developing antibodies against FVIII in an individual diagnosed with Hemophilia A comprising the steps of detecting the presence SNP rs12831813 in a biological sample from the individual; and predicting the risk of the individual of developing antibodies to FVIII. In one embodiment, the presence of SNP rs12831813 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12881815. In one embodiment, a method is provided for predicting the risk of developing antibodies against FVIII in an individual diagnosed with Hemophilia A comprising the steps of detecting the presence SNP rs12881815 in a biological sample from the individual; and predicting the risk of the individual of developing antibodies to FVIII. In one embodiment, the presence of SNP rs12881815 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12959952. In one embodiment, a method is provided for predicting the risk of developing antibodies against FVIII in an individual diagnosed with Hemophilia A comprising the steps of detecting the presence SNP rs12959952 in a biological sample from the individual; and predicting the risk of the individual of developing antibodies to FVIII. In one embodiment, the presence of SNP rs12959952 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs12969613. In one embodiment, a method is provided for predicting the risk of developing antibodies against FVIII in an individual diagnosed with Hemophilia A comprising the steps of detecting the presence SNP rs12969613 in a biological sample from the individual; and predicting the risk of the individual of developing antibodies to FVIII. In one embodiment, the presence of SNP rs12969613 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs13042473. In one embodiment, a method is provided for predicting the risk of developing antibodies against FVIII in an individual diagnosed with Hemophilia A comprising the steps of detecting the presence SNP rs13042473 in a biological sample from the individual; and predicting the risk of the individual of developing antibodies to FVIII. In one embodiment, the presence of SNP rs13042473 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs13096099. In one embodiment, a method is provided for predicting the risk of developing antibodies against FVIII in an individual diagnosed with Hemophilia A comprising the steps of detecting the presence SNP rs13096099 in a biological sample from the individual; and predicting the risk of the individual of developing antibodies to FVIII. In one embodiment, the presence of SNP rs13096099 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs13172280. In one embodiment, a method is provided for predicting the risk of developing antibodies against FVIII in an individual diagnosed with Hemophilia A comprising the steps of detecting the presence SNP rs13172280 in a biological sample from the individual; and predicting the risk of the individual of developing antibodies to FVIII. In one embodiment, the presence of SNP rs13172280 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs13173943. In one embodiment, a method is provided for predicting the risk of developing antibodies against FVIII in an individual diagnosed with Hemophilia A comprising the steps of detecting the presence SNP rs13173943 in a biological sample from the individual; and predicting the risk of the individual of developing antibodies to FVIII. In one embodiment, the presence of SNP rs13173943 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs13206518. In one embodiment, a method is provided for predicting the risk of developing antibodies against FVIII in an individual diagnosed with Hemophilia A comprising the steps of detecting the presence SNP rs13206518 in a biological sample from the individual; and predicting the risk of the individual of developing antibodies to FVIII. In one embodiment, the presence of SNP rs13206518 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1378796. In one embodiment, a method is provided for predicting the risk of developing antibodies against FVIII in an individual diagnosed with Hemophilia A comprising the steps of detecting the presence SNP rs1378796 in a biological sample from the individual; and predicting the risk of the individual of developing antibodies to FVIII. In one embodiment, the presence of SNP rs1378796 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1411479. In one embodiment, a method is provided for predicting the risk of developing antibodies against FVIII in an individual diagnosed with Hemophilia A comprising the steps of detecting the presence SNP rs1411479 in a biological sample from the individual; and predicting the risk of the individual of developing antibodies to FVIII. In one embodiment, the presence of SNP rs1411479 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1436522. In one embodiment, a method is provided for predicting the risk of developing antibodies against FVIII in an individual diagnosed with Hemophilia A comprising the steps of detecting the presence SNP rs1436522 in a biological sample from the individual; and predicting the risk of the individual of developing antibodies to FVIII. In one embodiment, the presence of SNP rs1436522 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1457238. In one embodiment, a method is provided for predicting the risk of developing antibodies against FVIII in an individual diagnosed with Hemophilia A comprising the steps of detecting the presence SNP rs1457238 in a biological sample from the individual; and predicting the risk of the individual of developing antibodies to FVIII. In one embodiment, the presence of SNP rs1457238 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1465073. In one embodiment, a method is provided for predicting the risk of developing antibodies against FVIII in an individual diagnosed with Hemophilia A comprising the steps of detecting the presence SNP rs1465073 in a biological sample from the individual; and predicting the risk of the individual of developing antibodies to FVIII. In one embodiment, the presence of SNP rs1465073 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1519602. In one embodiment, a method is provided for predicting the risk of developing antibodies against FVIII in an individual diagnosed with Hemophilia A comprising the steps of detecting the presence SNP rs1519602 in a biological sample from the individual; and predicting the risk of the individual of developing antibodies to FVIII. In one embodiment, the presence of SNP rs1519602 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1523474. In one embodiment, a method is provided for predicting the risk of developing antibodies against FVIII in an individual diagnosed with Hemophilia A comprising the steps of detecting the presence SNP rs1523474 in a biological sample from the individual; and predicting the risk of the individual of developing antibodies to FVIII. In one embodiment, the presence of SNP rs1523474 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1552323. In one embodiment, a method is provided for predicting the risk of developing antibodies against FVIII in an individual diagnosed with Hemophilia A comprising the steps of detecting the presence SNP rs1552323 in a biological sample from the individual; and predicting the risk of the individual of developing antibodies to FVIII. In one embodiment, the presence of SNP rs1552323 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1567748. In one embodiment, a method is provided for predicting the risk of developing antibodies against FVIII in an individual diagnosed with Hemophilia A comprising the steps of detecting the presence SNP rs1567748 in a biological sample from the individual; and predicting the risk of the individual of developing antibodies to FVIII. In one embodiment, the presence of SNP rs1567748 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1573706. In one embodiment, a method is provided for predicting the risk of developing antibodies against FVIII in an individual diagnosed with Hemophilia A comprising the steps of detecting the presence SNP rs1573706 in a biological sample from the individual; and predicting the risk of the individual of developing antibodies to FVIII. In one embodiment, the presence of SNP rs1573706 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs161021. In one embodiment, a method is provided for predicting the risk of developing antibodies against FVIII in an individual diagnosed with Hemophilia A comprising the steps of detecting the presence SNP rs161021 in a biological sample from the individual; and predicting the risk of the individual of developing antibodies to FVIII. In one embodiment, the presence of SNP rs161021 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs161042. In one embodiment, a method is provided for predicting the risk of developing antibodies against FVIII in an individual diagnosed with Hemophilia A comprising the steps of detecting the presence SNP rs161042 in a biological sample from the individual; and predicting the risk of the individual of developing antibodies to FVIII. In one embodiment, the presence of SNP rs161042 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1638006. In one embodiment, a method is provided for predicting the risk of developing antibodies against FVIII in an individual diagnosed with Hemophilia A comprising the steps of detecting the presence SNP rs1638006 in a biological sample from the individual; and predicting the risk of the individual of developing antibodies to FVIII. In one embodiment, the presence of SNP rs1638006 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs169142. In one embodiment, a method is provided for predicting the risk of developing antibodies against FVIII in an individual diagnosed with Hemophilia A comprising the steps of detecting the presence SNP rs169142 in a biological sample from the individual; and predicting the risk of the individual of developing antibodies to FVIII. In one embodiment, the presence of SNP rs169142 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17110948. In one embodiment, a method is provided for predicting the risk of developing antibodies against FVIII in an individual diagnosed with Hemophilia A comprising the steps of detecting the presence SNP rs17110948 in a biological sample from the individual; and predicting the risk of the individual of developing antibodies to FVIII. In one embodiment, the presence of SNP rs17110948 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17113227. In one embodiment, a method is provided for predicting the risk of developing antibodies against FVIII in an individual diagnosed with Hemophilia A comprising the steps of detecting the presence SNP rs17113227 in a biological sample from the individual; and predicting the risk of the individual of developing antibodies to FVIII. In one embodiment, the presence of SNP rs17113227 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17141840. In one embodiment, a method is provided for predicting the risk of developing antibodies against FVIII in an individual diagnosed with Hemophilia A comprising the steps of detecting the presence SNP rs17141840 in a biological sample from the individual; and predicting the risk of the individual of developing antibodies to FVIII. In one embodiment, the presence of SNP rs17141840 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17201075. In one embodiment, a method is provided for predicting the risk of developing antibodies against FVIII in an individual diagnosed with Hemophilia A comprising the steps of detecting the presence SNP rs17201075 in a biological sample from the individual; and predicting the risk of the individual of developing antibodies to FVIII. In one embodiment, the presence of SNP rs17201075 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17228097. In one embodiment, a method is provided for predicting the risk of developing antibodies against FVIII in an individual diagnosed with Hemophilia A comprising the steps of detecting the presence SNP rs17228097 in a biological sample from the individual; and predicting the risk of the individual of developing antibodies to FVIII. In one embodiment, the presence of SNP rs17228097 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1724120. In one embodiment, a method is provided for predicting the risk of developing antibodies against FVIII in an individual diagnosed with Hemophilia A comprising the steps of detecting the presence SNP rs1724120 in a biological sample from the individual; and predicting the risk of the individual of developing antibodies to FVIII. In one embodiment, the presence of SNP rs1724120 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17283264. In one embodiment, a method is provided for predicting the risk of developing antibodies against FVIII in an individual diagnosed with Hemophilia A comprising the steps of detecting the presence SNP rs17283264 in a biological sample from the individual; and predicting the risk of the individual of developing antibodies to FVIII. In one embodiment, the presence of SNP rs17283264 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17317153. In one embodiment, a method is provided for predicting the risk of developing antibodies against FVIII in an individual diagnosed with Hemophilia A comprising the steps of detecting the presence SNP rs17317153 in a biological sample from the individual; and predicting the risk of the individual of developing antibodies to FVIII. In one embodiment, the presence of SNP rs17317153 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17419586. In one embodiment, a method is provided for predicting the risk of developing antibodies against FVIII in an individual diagnosed with Hemophilia A comprising the steps of detecting the presence SNP rs17419586 in a biological sample from the individual; and predicting the risk of the individual of developing antibodies to FVIII. In one embodiment, the presence of SNP rs17419586 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17535213. In one embodiment, a method is provided for predicting the risk of developing antibodies against FVIII in an individual diagnosed with Hemophilia A comprising the steps of detecting the presence SNP rs17535213 in a biological sample from the individual; and predicting the risk of the individual of developing antibodies to FVIII. In one embodiment, the presence of SNP rs17535213 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17652304. In one embodiment, a method is provided for predicting the risk of developing antibodies against FVIII in an individual diagnosed with Hemophilia A comprising the steps of detecting the presence SNP rs17652304 in a biological sample from the individual; and predicting the risk of the individual of developing antibodies to FVIII. In one embodiment, the presence of SNP rs17652304 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17671456. In one embodiment, a method is provided for predicting the risk of developing antibodies against FVIII in an individual diagnosed with Hemophilia A comprising the steps of detecting the presence SNP rs17671456 in a biological sample from the individual; and predicting the risk of the individual of developing antibodies to FVIII. In one embodiment, the presence of SNP rs17671456 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17725712. In one embodiment, a method is provided for predicting the risk of developing antibodies against FVIII in an individual diagnosed with Hemophilia A comprising the steps of detecting the presence SNP rs17725712 in a biological sample from the individual; and predicting the risk of the individual of developing antibodies to FVIII. In one embodiment, the presence of SNP rs17725712 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17748322. In one embodiment, a method is provided for predicting the risk of developing antibodies against FVIII in an individual diagnosed with Hemophilia A comprising the steps of detecting the presence SNP rs17748322 in a biological sample from the individual; and predicting the risk of the individual of developing antibodies to FVIII. In one embodiment, the presence of SNP rs17748322 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17763453. In one embodiment, a method is provided for predicting the risk of developing antibodies against FVIII in an individual diagnosed with Hemophilia A comprising the steps of detecting the presence SNP rs17763453 in a biological sample from the individual; and predicting the risk of the individual of developing antibodies to FVIII. In one embodiment, the presence of SNP rs17763453 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17811425. In one embodiment, a method is provided for predicting the risk of developing antibodies against FVIII in an individual diagnosed with Hemophilia A comprising the steps of detecting the presence SNP rs17811425 in a biological sample from the individual; and predicting the risk of the individual of developing antibodies to FVIII. In one embodiment, the presence of SNP rs17811425 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17815972. In one embodiment, a method is provided for predicting the risk of developing antibodies against FVIII in an individual diagnosed with Hemophilia A comprising the steps of detecting the presence SNP rs17815972 in a biological sample from the individual; and predicting the risk of the individual of developing antibodies to FVIII. In one embodiment, the presence of SNP rs17815972 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1781795. In one embodiment, a method is provided for predicting the risk of developing antibodies against FVIII in an individual diagnosed with Hemophilia A comprising the steps of detecting the presence SNP rs1781795 in a biological sample from the individual; and predicting the risk of the individual of developing antibodies to FVIII. In one embodiment, the presence of SNP rs1781795 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17834679. In one embodiment, a method is provided for predicting the risk of developing antibodies against FVIII in an individual diagnosed with Hemophilia A comprising the steps of detecting the presence SNP rs17834679 in a biological sample from the individual; and predicting the risk of the individual of developing antibodies to FVIII. In one embodiment, the presence of SNP rs17834679 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs17875513. In one embodiment, a method is provided for predicting the risk of developing antibodies against FVIII in an individual diagnosed with Hemophilia A comprising the steps of detecting the presence SNP rs17875513 in a biological sample from the individual; and predicting the risk of the individual of developing antibodies to FVIII. In one embodiment, the presence of SNP rs17875513 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1797646. In one embodiment, a method is provided for predicting the risk of developing antibodies against FVIII in an individual diagnosed with Hemophilia A comprising the steps of detecting the presence SNP rs1797646 in a biological sample from the individual; and predicting the risk of the individual of developing antibodies to FVIII. In one embodiment, the presence of SNP rs1797646 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1797647. In one embodiment, a method is provided for predicting the risk of developing antibodies against FVIII in an individual diagnosed with Hemophilia A comprising the steps of detecting the presence SNP rs1797647 in a biological sample from the individual; and predicting the risk of the individual of developing antibodies to FVIII. In one embodiment, the presence of SNP rs1797647 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1838065. In one embodiment, a method is provided for predicting the risk of developing antibodies against FVIII in an individual diagnosed with Hemophilia A comprising the steps of detecting the presence SNP rs1838065 in a biological sample from the individual; and predicting the risk of the individual of developing antibodies to FVIII. In one embodiment, the presence of SNP rs1838065 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1863993. In one embodiment, a method is provided for predicting the risk of developing antibodies against FVIII in an individual diagnosed with Hemophilia A comprising the steps of detecting the presence SNP rs1863993 in a biological sample from the individual; and predicting the risk of the individual of developing antibodies to FVIII. In one embodiment, the presence of SNP rs1863993 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1865462. In one embodiment, a method is provided for predicting the risk of developing antibodies against FVIII in an individual diagnosed with Hemophilia A comprising the steps of detecting the presence SNP rs1865462 in a biological sample from the individual; and predicting the risk of the individual of developing antibodies to FVIII. In one embodiment, the presence of SNP rs1865462 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1877563. In one embodiment, a method is provided for predicting the risk of developing antibodies against FVIII in an individual diagnosed with Hemophilia A comprising the steps of detecting the presence SNP rs1877563 in a biological sample from the individual; and predicting the risk of the individual of developing antibodies to FVIII. In one embodiment, the presence of SNP rs1877563 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1882019. In one embodiment, a method is provided for predicting the risk of developing antibodies against FVIII in an individual diagnosed with Hemophilia A comprising the steps of detecting the presence SNP rs1882019 in a biological sample from the individual; and predicting the risk of the individual of developing antibodies to FVIII. In one embodiment, the presence of SNP rs1882019 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1884564. In one embodiment, a method is provided for predicting the risk of developing antibodies against FVIII in an individual diagnosed with Hemophilia A comprising the steps of detecting the presence SNP rs1884564 in a biological sample from the individual; and predicting the risk of the individual of developing antibodies to FVIII. In one embodiment, the presence of SNP rs1884564 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1885831. In one embodiment, a method is provided for predicting the risk of developing antibodies against FVIII in an individual diagnosed with Hemophilia A comprising the steps of detecting the presence SNP rs1885831 in a biological sample from the individual; and predicting the risk of the individual of developing antibodies to FVIII. In one embodiment, the presence of SNP rs1885831 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1892803. In one embodiment, a method is provided for predicting the risk of developing antibodies against FVIII in an individual diagnosed with Hemophilia A comprising the steps of detecting the presence SNP rs1892803 in a biological sample from the individual; and predicting the risk of the individual of developing antibodies to FVIII. In one embodiment, the presence of SNP rs1892803 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1918309. In one embodiment, a method is provided for predicting the risk of developing antibodies against FVIII in an individual diagnosed with Hemophilia A comprising the steps of detecting the presence SNP rs1918309 in a biological sample from the individual; and predicting the risk of the individual of developing antibodies to FVIII. In one embodiment, the presence of SNP rs1918309 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1983165. In one embodiment, a method is provided for predicting the risk of developing antibodies against FVIII in an individual diagnosed with Hemophilia A comprising the steps of detecting the presence SNP rs1983165 in a biological sample from the individual; and predicting the risk of the individual of developing antibodies to FVIII. In one embodiment, the presence of SNP rs1983165 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs1984399. In one embodiment, a method is provided for predicting the risk of developing antibodies against FVIII in an individual diagnosed with Hemophilia A comprising the steps of detecting the presence SNP rs1984399 in a biological sample from the individual; and predicting the risk of the individual of developing antibodies to FVIII. In one embodiment, the presence of SNP rs1984399 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2010452. In one embodiment, a method is provided for predicting the risk of developing antibodies against FVIII in an individual diagnosed with Hemophilia A comprising the steps of detecting the presence SNP rs2010452 in a biological sample from the individual; and predicting the risk of the individual of developing antibodies to FVIII. In one embodiment, the presence of SNP rs2010452 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2020902. In one embodiment, a method is provided for predicting the risk of developing antibodies against FVIII in an individual diagnosed with Hemophilia A comprising the steps of detecting the presence SNP rs2020902 in a biological sample from the individual; and predicting the risk of the individual of developing antibodies to FVIII. In one embodiment, the presence of SNP rs2020902 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2069933. In one embodiment, a method is provided for predicting the risk of developing antibodies against FVIII in an individual diagnosed with Hemophilia A comprising the steps of detecting the presence SNP rs2069933 in a biological sample from the individual; and predicting the risk of the individual of developing antibodies to FVIII. In one embodiment, the presence of SNP rs2069933 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2070123. In one embodiment, a method is provided for predicting the risk of developing antibodies against FVIII in an individual diagnosed with Hemophilia A comprising the steps of detecting the presence SNP rs2070123 in a biological sample from the individual; and predicting the risk of the individual of developing antibodies to FVIII. In one embodiment, the presence of SNP rs2070123 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2070783. In one embodiment, a method is provided for predicting the risk of developing antibodies against FVIII in an individual diagnosed with Hemophilia A comprising the steps of detecting the presence SNP rs2070783 in a biological sample from the individual; and predicting the risk of the individual of developing antibodies to FVIII. In one embodiment, the presence of SNP rs2070783 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2071081. In one embodiment, a method is provided for predicting the risk of developing antibodies against FVIII in an individual diagnosed with Hemophilia A comprising the steps of detecting the presence SNP rs2071081 in a biological sample from the individual; and predicting the risk of the individual of developing antibodies to FVIII. In one embodiment, the presence of SNP rs2071081 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2071336. In one embodiment, a method is provided for predicting the risk of developing antibodies against FVIII in an individual diagnosed with Hemophilia A comprising the steps of detecting the presence SNP rs2071336 in a biological sample from the individual; and predicting the risk of the individual of developing antibodies to FVIII. In one embodiment, the presence of SNP rs2071336 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2076620. In one embodiment, a method is provided for predicting the risk of developing antibodies against FVIII in an individual diagnosed with Hemophilia A comprising the steps of detecting the presence SNP rs2076620 in a biological sample from the individual; and predicting the risk of the individual of developing antibodies to FVIII. In one embodiment, the presence of SNP rs2076620 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2076846. In one embodiment, a method is provided for predicting the risk of developing antibodies against FVIII in an individual diagnosed with Hemophilia A comprising the steps of detecting the presence SNP rs2076846 in a biological sample from the individual; and predicting the risk of the individual of developing antibodies to FVIII. In one embodiment, the presence of SNP rs2076846 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs208250. In one embodiment, a method is provided for predicting the risk of developing antibodies against FVIII in an individual diagnosed with Hemophilia A comprising the steps of detecting the presence SNP rs208250 in a biological sample from the individual; and predicting the risk of the individual of developing antibodies to FVIII. In one embodiment, the presence of SNP rs208250 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs210431. In one embodiment, a method is provided for predicting the risk of developing antibodies against FVIII in an individual diagnosed with Hemophilia A comprising the steps of detecting the presence SNP rs210431 in a biological sample from the individual; and predicting the risk of the individual of developing antibodies to FVIII. In one embodiment, the presence of SNP rs210431 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2157605. In one embodiment, a method is provided for predicting the risk of developing antibodies against FVIII in an individual diagnosed with Hemophilia A comprising the steps of detecting the presence SNP rs2157605 in a biological sample from the individual; and predicting the risk of the individual of developing antibodies to FVIII. In one embodiment, the presence of SNP rs2157605 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2163057. In one embodiment, a method is provided for predicting the risk of developing antibodies against FVIII in an individual diagnosed with Hemophilia A comprising the steps of detecting the presence SNP rs2163057 in a biological sample from the individual; and predicting the risk of the individual of developing antibodies to FVIII. In one embodiment, the presence of SNP rs2163057 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2179694. In one embodiment, a method is provided for predicting the risk of developing antibodies against FVIII in an individual diagnosed with Hemophilia A comprising the steps of detecting the presence SNP rs2179694 in a biological sample from the individual; and predicting the risk of the individual of developing antibodies to FVIII. In one embodiment, the presence of SNP rs2179694 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2227562. In one embodiment, a method is provided for predicting the risk of developing antibodies against FVIII in an individual diagnosed with Hemophilia A comprising the steps of detecting the presence SNP rs2227562 in a biological sample from the individual; and predicting the risk of the individual of developing antibodies to FVIII. In one embodiment, the presence of SNP rs2227562 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2227827. In one embodiment, a method is provided for predicting the risk of developing antibodies against FVIII in an individual diagnosed with Hemophilia A comprising the steps of detecting the presence SNP rs2227827 in a biological sample from the individual; and predicting the risk of the individual of developing antibodies to FVIII. In one embodiment, the presence of SNP rs2227827 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2231375. In one embodiment, a method is provided for predicting the risk of developing antibodies against FVIII in an individual diagnosed with Hemophilia A comprising the steps of detecting the presence SNP rs2231375 in a biological sample from the individual; and predicting the risk of the individual of developing antibodies to FVIII. In one embodiment, the presence of SNP rs2231375 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2238337. In one embodiment, a method is provided for predicting the risk of developing antibodies against FVIII in an individual diagnosed with Hemophilia A comprising the steps of detecting the presence SNP rs2238337 in a biological sample from the individual; and predicting the risk of the individual of developing antibodies to FVIII. In one embodiment, the presence of SNP rs2238337 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2242660. In one embodiment, a method is provided for predicting the risk of developing antibodies against FVIII in an individual diagnosed with Hemophilia A comprising the steps of detecting the presence SNP rs2242660 in a biological sample from the individual; and predicting the risk of the individual of developing antibodies to FVIII. In one embodiment, the presence of SNP rs2242660 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2255364. In one embodiment, a method is provided for predicting the risk of developing antibodies against FVIII in an individual diagnosed with Hemophilia A comprising the steps of detecting the presence SNP rs2255364 in a biological sample from the individual; and predicting the risk of the individual of developing antibodies to FVIII. In one embodiment, the presence of SNP rs2255364 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2267908. In one embodiment, a method is provided for predicting the risk of developing antibodies against FVIII in an individual diagnosed with Hemophilia A comprising the steps of detecting the presence SNP rs2267908 in a biological sample from the individual; and predicting the risk of the individual of developing antibodies to FVIII. In one embodiment, the presence of SNP rs2267908 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2268890. In one embodiment, a method is provided for predicting the risk of developing antibodies against FVIII in an individual diagnosed with Hemophilia A comprising the steps of detecting the presence SNP rs2268890 in a biological sample from the individual; and predicting the risk of the individual of developing antibodies to FVIII. In one embodiment, the presence of SNP rs2268890 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2275603. In one embodiment, a method is provided for predicting the risk of developing antibodies against FVIII in an individual diagnosed with Hemophilia A comprising the steps of detecting the presence SNP rs2275603 in a biological sample from the individual; and predicting the risk of the individual of developing antibodies to FVIII. In one embodiment, the presence of SNP rs2275603 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2278324. In one embodiment, a method is provided for predicting the risk of developing antibodies against FVIII in an individual diagnosed with Hemophilia A comprising the steps of detecting the presence SNP rs2278324 in a biological sample from the individual; and predicting the risk of the individual of developing antibodies to FVIII. In one embodiment, the presence of SNP rs2278324 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2279590. In one embodiment, a method is provided for predicting the risk of developing antibodies against FVIII in an individual diagnosed with Hemophilia A comprising the steps of detecting the presence SNP rs2279590 in a biological sample from the individual; and predicting the risk of the individual of developing antibodies to FVIII. In one embodiment, the presence of SNP rs2279590 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2283539. In one embodiment, a method is provided for predicting the risk of developing antibodies against FVIII in an individual diagnosed with Hemophilia A comprising the steps of detecting the presence SNP rs2283539 in a biological sample from the individual; and predicting the risk of the individual of developing antibodies to FVIII. In one embodiment, the presence of SNP rs2283539 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2286414. In one embodiment, a method is provided for predicting the risk of developing antibodies against FVIII in an individual diagnosed with Hemophilia A comprising the steps of detecting the presence SNP rs2286414 in a biological sample from the individual; and predicting the risk of the individual of developing antibodies to FVIII. In one embodiment, the presence of SNP rs2286414 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2287768. In one embodiment, a method is provided for predicting the risk of developing antibodies against FVIII in an individual diagnosed with Hemophilia A comprising the steps of detecting the presence SNP rs2287768 in a biological sample from the individual; and predicting the risk of the individual of developing antibodies to FVIII. In one embodiment, the presence of SNP rs2287768 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2288522. In one embodiment, a method is provided for predicting the risk of developing antibodies against FVIII in an individual diagnosed with Hemophilia A comprising the steps of detecting the presence SNP rs2288522 in a biological sample from the individual; and predicting the risk of the individual of developing antibodies to FVIII. In one embodiment, the presence of SNP rs2288522 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2295616. In one embodiment, a method is provided for predicting the risk of developing antibodies against FVIII in an individual diagnosed with Hemophilia A comprising the steps of detecting the presence SNP rs2295616 in a biological sample from the individual; and predicting the risk of the individual of developing antibodies to FVIII. In one embodiment, the presence of SNP rs2295616 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2296449. In one embodiment, a method is provided for predicting the risk of developing antibodies against FVIII in an individual diagnosed with Hemophilia A comprising the steps of detecting the presence SNP rs2296449 in a biological sample from the individual; and predicting the risk of the individual of developing antibodies to FVIII. In one embodiment, the presence of SNP rs2296449 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2298877. In one embodiment, a method is provided for predicting the risk of developing antibodies against FVIII in an individual diagnosed with Hemophilia A comprising the steps of detecting the presence SNP rs2298877 in a biological sample from the individual; and predicting the risk of the individual of developing antibodies to FVIII. In one embodiment, the presence of SNP rs2298877 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2302267. In one embodiment, a method is provided for predicting the risk of developing antibodies against FVIII in an individual diagnosed with Hemophilia A comprising the steps of detecting the presence SNP rs2302267 in a biological sample from the individual; and predicting the risk of the individual of developing antibodies to FVIII. In one embodiment, the presence of SNP rs2302267 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2302759. In one embodiment, a method is provided for predicting the risk of developing antibodies against FVIII in an individual diagnosed with Hemophilia A comprising the steps of detecting the presence SNP rs2302759 in a biological sample from the individual; and predicting the risk of the individual of developing antibodies to FVIII. In one embodiment, the presence of SNP rs2302759 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2302821. In one embodiment, a method is provided for predicting the risk of developing antibodies against FVIII in an individual diagnosed with Hemophilia A comprising the steps of detecting the presence SNP rs2302821 in a biological sample from the individual; and predicting the risk of the individual of developing antibodies to FVIII. In one embodiment, the presence of SNP rs2302821 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2305340. In one embodiment, a method is provided for predicting the risk of developing antibodies against FVIII in an individual diagnosed with Hemophilia A comprising the steps of detecting the presence SNP rs2305340 in a biological sample from the individual; and predicting the risk of the individual of developing antibodies to FVIII. In one embodiment, the presence of SNP rs2305340 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2335478. In one embodiment, a method is provided for predicting the risk of developing antibodies against FVIII in an individual diagnosed with Hemophilia A comprising the steps of detecting the presence SNP rs2335478 in a biological sample from the individual; and predicting the risk of the individual of developing antibodies to FVIII. In one embodiment, the presence of SNP rs2335478 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs241430. In one embodiment, a method is provided for predicting the risk of developing antibodies against FVIII in an individual diagnosed with Hemophilia A comprising the steps of detecting the presence SNP rs241430 in a biological sample from the individual; and predicting the risk of the individual of developing antibodies to FVIII. In one embodiment, the presence of SNP rs241430 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs244076. In one embodiment, a method is provided for predicting the risk of developing antibodies against FVIII in an individual diagnosed with Hemophilia A comprising the steps of detecting the presence SNP rs244076 in a biological sample from the individual; and predicting the risk of the individual of developing antibodies to FVIII. In one embodiment, the presence of SNP rs244076 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs244090. In one embodiment, a method is provided for predicting the risk of developing antibodies against FVIII in an individual diagnosed with Hemophilia A comprising the steps of detecting the presence SNP rs244090 in a biological sample from the individual; and predicting the risk of the individual of developing antibodies to FVIII. In one embodiment, the presence of SNP rs244090 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs244091. In one embodiment, a method is provided for predicting the risk of developing antibodies against FVIII in an individual diagnosed with Hemophilia A comprising the steps of detecting the presence SNP rs244091 in a biological sample from the individual; and predicting the risk of the individual of developing antibodies to FVIII. In one embodiment, the presence of SNP rs244091 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs244656. In one embodiment, a method is provided for predicting the risk of developing antibodies against FVIII in an individual diagnosed with Hemophilia A comprising the steps of detecting the presence SNP rs244656 in a biological sample from the individual; and predicting the risk of the individual of developing antibodies to FVIII. In one embodiment, the presence of SNP rs244656 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs246390. In one embodiment, a method is provided for predicting the risk of developing antibodies against FVIII in an individual diagnosed with Hemophilia A comprising the steps of detecting the presence SNP rs246390 in a biological sample from the individual; and predicting the risk of the individual of developing antibodies to FVIII. In one embodiment, the presence of SNP rs246390 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs246392. In one embodiment, a method is provided for predicting the risk of developing antibodies against FVIII in an individual diagnosed with Hemophilia A comprising the steps of detecting the presence SNP rs246392 in a biological sample from the individual; and predicting the risk of the individual of developing antibodies to FVIII. In one embodiment, the presence of SNP rs246392 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs246394. In one embodiment, a method is provided for predicting the risk of developing antibodies against FVIII in an individual diagnosed with Hemophilia A comprising the steps of detecting the presence SNP rs246394 in a biological sample from the individual; and predicting the risk of the individual of developing antibodies to FVIII. In one embodiment, the presence of SNP rs246394 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs246395. In one embodiment, a method is provided for predicting the risk of developing antibodies against FVIII in an individual diagnosed with Hemophilia A comprising the steps of detecting the presence SNP rs246395 in a biological sample from the individual; and predicting the risk of the individual of developing antibodies to FVIII. In one embodiment, the presence of SNP rs246395 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2569190. In one embodiment, a method is provided for predicting the risk of developing antibodies against FVIII in an individual diagnosed with Hemophilia A comprising the steps of detecting the presence SNP rs2569190 in a biological sample from the individual; and predicting the risk of the individual of developing antibodies to FVIII. In one embodiment, the presence of SNP rs2569190 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2575674. In one embodiment, a method is provided for predicting the risk of developing antibodies against FVIII in an individual diagnosed with Hemophilia A comprising the steps of detecting the presence SNP rs2575674 in a biological sample from the individual; and predicting the risk of the individual of developing antibodies to FVIII. In one embodiment, the presence of SNP rs2575674 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2584019. In one embodiment, a method is provided for predicting the risk of developing antibodies against FVIII in an individual diagnosed with Hemophilia A comprising the steps of detecting the presence SNP rs2584019 in a biological sample from the individual; and predicting the risk of the individual of developing antibodies to FVIII. In one embodiment, the presence of SNP rs2584019 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2595204. In one embodiment, a method is provided for predicting the risk of developing antibodies against FVIII in an individual diagnosed with Hemophilia A comprising the steps of detecting the presence SNP rs2595204 in a biological sample from the individual; and predicting the risk of the individual of developing antibodies to FVIII. In one embodiment, the presence of SNP rs2595204 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2596606. In one embodiment, a method is provided for predicting the risk of developing antibodies against FVIII in an individual diagnosed with Hemophilia A comprising the steps of detecting the presence SNP rs2596606 in a biological sample from the individual; and predicting the risk of the individual of developing antibodies to FVIII. In one embodiment, the presence of SNP rs2596606 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2838733. In one embodiment, a method is provided for predicting the risk of developing antibodies against FVIII in an individual diagnosed with Hemophilia A comprising the steps of detecting the presence SNP rs2838733 in a biological sample from the individual; and predicting the risk of the individual of developing antibodies to FVIII. In one embodiment, the presence of SNP rs2838733 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2844463. In one embodiment, a method is provided for predicting the risk of developing antibodies against FVIII in an individual diagnosed with Hemophilia A comprising the steps of detecting the presence SNP rs2844463 in a biological sample from the individual; and predicting the risk of the individual of developing antibodies to FVIII. In one embodiment, the presence of SNP rs2844463 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2853884. In one embodiment, a method is provided for predicting the risk of developing antibodies against FVIII in an individual diagnosed with Hemophilia A comprising the steps of detecting the presence SNP rs2853884 in a biological sample from the individual; and predicting the risk of the individual of developing antibodies to FVIII. In one embodiment, the presence of SNP rs2853884 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2869460. In one embodiment, a method is provided for predicting the risk of developing antibodies against FVIII in an individual diagnosed with Hemophilia A comprising the steps of detecting the presence SNP rs2869460 in a biological sample from the individual; and predicting the risk of the individual of developing antibodies to FVIII. In one embodiment, the presence of SNP rs2869460 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2869461. In one embodiment, a method is provided for predicting the risk of developing antibodies against FVIII in an individual diagnosed with Hemophilia A comprising the steps of detecting the presence SNP rs2869461 in a biological sample from the individual; and predicting the risk of the individual of developing antibodies to FVIII. In one embodiment, the presence of SNP rs2869461 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs2879097. In one embodiment, a method is provided for predicting the risk of developing antibodies against FVIII in an individual diagnosed with Hemophilia A comprising the steps of detecting the presence SNP rs2879097 in a biological sample from the individual; and predicting the risk of the individual of developing antibodies to FVIII. In one embodiment, the presence of SNP rs2879097 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3024486. In one embodiment, a method is provided for predicting the risk of developing antibodies against FVIII in an individual diagnosed with Hemophilia A comprising the steps of detecting the presence SNP rs3024486 in a biological sample from the individual; and predicting the risk of the individual of developing antibodies to FVIII. In one embodiment, the presence of SNP rs3024486 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3024498. In one embodiment, a method is provided for predicting the risk of developing antibodies against FVIII in an individual diagnosed with Hemophilia A comprising the steps of detecting the presence SNP rs3024498 in a biological sample from the individual; and predicting the risk of the individual of developing antibodies to FVIII. In one embodiment, the presence of SNP rs3024498 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs304839. In one embodiment, a method is provided for predicting the risk of developing antibodies against FVIII in an individual diagnosed with Hemophilia A comprising the steps of detecting the presence SNP rs304839 in a biological sample from the individual; and predicting the risk of the individual of developing antibodies to FVIII. In one embodiment, the presence of SNP rs304839 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs310247. In one embodiment, a method is provided for predicting the risk of developing antibodies against FVIII in an individual diagnosed with Hemophilia A comprising the steps of detecting the presence SNP rs310247 in a biological sample from the individual; and predicting the risk of the individual of developing antibodies to FVIII. In one embodiment, the presence of SNP rs310247 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs31519. In one embodiment, a method is provided for predicting the risk of developing antibodies against FVIII in an individual diagnosed with Hemophilia A comprising the steps of detecting the presence SNP rs31519 in a biological sample from the individual; and predicting the risk of the individual of developing antibodies to FVIII. In one embodiment, the presence of SNP rs31519 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3181096. In one embodiment, a method is provided for predicting the risk of developing antibodies against FVIII in an individual diagnosed with Hemophilia A comprising the steps of detecting the presence SNP rs3181096 in a biological sample from the individual; and predicting the risk of the individual of developing antibodies to FVIII. In one embodiment, the presence of SNP rs3181096 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3211821. In one embodiment, a method is provided for predicting the risk of developing antibodies against FVIII in an individual diagnosed with Hemophilia A comprising the steps of detecting the presence SNP rs3211821 in a biological sample from the individual; and predicting the risk of the individual of developing antibodies to FVIII. In one embodiment, the presence of SNP rs3211821 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3211834. In one embodiment, a method is provided for predicting the risk of developing antibodies against FVIII in an individual diagnosed with Hemophilia A comprising the steps of detecting the presence SNP rs3211834 in a biological sample from the individual; and predicting the risk of the individual of developing antibodies to FVIII. In one embodiment, the presence of SNP rs3211834 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3733236. In one embodiment, a method is provided for predicting the risk of developing antibodies against FVIII in an individual diagnosed with Hemophilia A comprising the steps of detecting the presence SNP rs3733236 in a biological sample from the individual; and predicting the risk of the individual of developing antibodies to FVIII. In one embodiment, the presence of SNP rs3733236 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3733678. In one embodiment, a method is provided for predicting the risk of developing antibodies against FVIII in an individual diagnosed with Hemophilia A comprising the steps of detecting the presence SNP rs3733678 in a biological sample from the individual; and predicting the risk of the individual of developing antibodies to FVIII. In one embodiment, the presence of SNP rs3733678 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3736101. In one embodiment, a method is provided for predicting the risk of developing antibodies against FVIII in an individual diagnosed with Hemophilia A comprising the steps of detecting the presence SNP rs3736101 in a biological sample from the individual; and predicting the risk of the individual of developing antibodies to FVIII. In one embodiment, the presence of SNP rs3736101 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3736395. In one embodiment, a method is provided for predicting the risk of developing antibodies against FVIII in an individual diagnosed with Hemophilia A comprising the steps of detecting the presence SNP rs3736395 in a biological sample from the individual; and predicting the risk of the individual of developing antibodies to FVIII. In one embodiment, the presence of SNP rs3736395 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3788151. In one embodiment, a method is provided for predicting the risk of developing antibodies against FVIII in an individual diagnosed with Hemophilia A comprising the steps of detecting the presence SNP rs3788151 in a biological sample from the individual; and predicting the risk of the individual of developing antibodies to FVIII. In one embodiment, the presence of SNP rs3788151 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3795326. In one embodiment, a method is provided for predicting the risk of developing antibodies against FVIII in an individual diagnosed with Hemophilia A comprising the steps of detecting the presence SNP rs3795326 in a biological sample from the individual; and predicting the risk of the individual of developing antibodies to FVIII. In one embodiment, the presence of SNP rs3795326 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3797390. In one embodiment, a method is provided for predicting the risk of developing antibodies against FVIII in an individual diagnosed with Hemophilia A comprising the steps of detecting the presence SNP rs3797390 in a biological sample from the individual; and predicting the risk of the individual of developing antibodies to FVIII. In one embodiment, the presence of SNP rs3797390 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3815003. In one embodiment, a method is provided for predicting the risk of developing antibodies against FVIII in an individual diagnosed with Hemophilia A comprising the steps of detecting the presence SNP rs3815003 in a biological sample from the individual; and predicting the risk of the individual of developing antibodies to FVIII. In one embodiment, the presence of SNP rs3815003 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3816724. In one embodiment, a method is provided for predicting the risk of developing antibodies against FVIII in an individual diagnosed with Hemophilia A comprising the steps of detecting the presence SNP rs3816724 in a biological sample from the individual; and predicting the risk of the individual of developing antibodies to FVIII. In one embodiment, the presence of SNP rs3816724 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3819496. In one embodiment, a method is provided for predicting the risk of developing antibodies against FVIII in an individual diagnosed with Hemophilia A comprising the steps of detecting the presence SNP rs3819496 in a biological sample from the individual; and predicting the risk of the individual of developing antibodies to FVIII. In one embodiment, the presence of SNP rs3819496 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3826392. In one embodiment, a method is provided for predicting the risk of developing antibodies against FVIII in an individual diagnosed with Hemophilia A comprising the steps of detecting the presence SNP rs3826392 in a biological sample from the individual; and predicting the risk of the individual of developing antibodies to FVIII. In one embodiment, the presence of SNP rs3826392 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3828016. In one embodiment, a method is provided for predicting the risk of developing antibodies against FVIII in an individual diagnosed with Hemophilia A comprising the steps of detecting the presence SNP rs3828016 in a biological sample from the individual; and predicting the risk of the individual of developing antibodies to FVIII. In one embodiment, the presence of SNP rs3828016 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs3845422. In one embodiment, a method is provided for predicting the risk of developing antibodies against FVIII in an individual diagnosed with Hemophilia A comprising the steps of detecting the presence SNP rs3845422 in a biological sample from the individual; and predicting the risk of the individual of developing antibodies to FVIII. In one embodiment, the presence of SNP rs3845422 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs390406. In one embodiment, a method is provided for predicting the risk of developing antibodies against FVIII in an individual diagnosed with Hemophilia A comprising the steps of detecting the presence SNP rs390406 in a biological sample from the individual; and predicting the risk of the individual of developing antibodies to FVIII. In one embodiment, the presence of SNP rs390406 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4027402. In one embodiment, a method is provided for predicting the risk of developing antibodies against FVIII in an individual diagnosed with Hemophilia A comprising the steps of detecting the presence SNP rs4027402 in a biological sample from the individual; and predicting the risk of the individual of developing antibodies to FVIII. In one embodiment, the presence of SNP rs4027402 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4077341. In one embodiment, a method is provided for predicting the risk of developing antibodies against FVIII in an individual diagnosed with Hemophilia A comprising the steps of detecting the presence SNP rs4077341 in a biological sample from the individual; and predicting the risk of the individual of developing antibodies to FVIII. In one embodiment, the presence of SNP rs4077341 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4094864. In one embodiment, a method is provided for predicting the risk of developing antibodies against FVIII in an individual diagnosed with Hemophilia A comprising the steps of detecting the presence SNP rs4094864 in a biological sample from the individual; and predicting the risk of the individual of developing antibodies to FVIII. In one embodiment, the presence of SNP rs4094864 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4104. In one embodiment, a method is provided for predicting the risk of developing antibodies against FVIII in an individual diagnosed with Hemophilia A comprising the steps of detecting the presence SNP rs4104 in a biological sample from the individual; and predicting the risk of the individual of developing antibodies to FVIII. In one embodiment, the presence of SNP rs4104 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs414634. In one embodiment, a method is provided for predicting the risk of developing antibodies against FVIII in an individual diagnosed with Hemophilia A comprising the steps of detecting the presence SNP rs414634 in a biological sample from the individual; and predicting the risk of the individual of developing antibodies to FVIII. In one embodiment, the presence of SNP rs414634 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4147385. In one embodiment, a method is provided for predicting the risk of developing antibodies against FVIII in an individual diagnosed with Hemophilia A comprising the steps of detecting the presence SNP rs4147385 in a biological sample from the individual; and predicting the risk of the individual of developing antibodies to FVIII. In one embodiment, the presence of SNP rs4147385 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs424051. In one embodiment, a method is provided for predicting the risk of developing antibodies against FVIII in an individual diagnosed with Hemophilia A comprising the steps of detecting the presence SNP rs424051 in a biological sample from the individual; and predicting the risk of the individual of developing antibodies to FVIII. In one embodiment, the presence of SNP rs424051 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4242389. In one embodiment, a method is provided for predicting the risk of developing antibodies against FVIII in an individual diagnosed with Hemophilia A comprising the steps of detecting the presence SNP rs4242389 in a biological sample from the individual; and predicting the risk of the individual of developing antibodies to FVIII. In one embodiment, the presence of SNP rs4242389 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4245886. In one embodiment, a method is provided for predicting the risk of developing antibodies against FVIII in an individual diagnosed with Hemophilia A comprising the steps of detecting the presence SNP rs4245886 in a biological sample from the individual; and predicting the risk of the individual of developing antibodies to FVIII. In one embodiment, the presence of SNP rs4245886 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4251520. In one embodiment, a method is provided for predicting the risk of developing antibodies against FVIII in an individual diagnosed with Hemophilia A comprising the steps of detecting the presence SNP rs4251520 in a biological sample from the individual; and predicting the risk of the individual of developing antibodies to FVIII. In one embodiment, the presence of SNP rs4251520 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4253655. In one embodiment, a method is provided for predicting the risk of developing antibodies against FVIII in an individual diagnosed with Hemophilia A comprising the steps of detecting the presence SNP rs4253655 in a biological sample from the individual; and predicting the risk of the individual of developing antibodies to FVIII. In one embodiment, the presence of SNP rs4253655 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs440238. In one embodiment, a method is provided for predicting the risk of developing antibodies against FVIII in an individual diagnosed with Hemophilia A comprising the steps of detecting the presence SNP rs440238 in a biological sample from the individual; and predicting the risk of the individual of developing antibodies to FVIII. In one embodiment, the presence of SNP rs440238 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4462251. In one embodiment, a method is provided for predicting the risk of developing antibodies against FVIII in an individual diagnosed with Hemophilia A comprising the steps of detecting the presence SNP rs4462251 in a biological sample from the individual; and predicting the risk of the individual of developing antibodies to FVIII. In one embodiment, the presence of SNP rs4462251 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4472605. In one embodiment, a method is provided for predicting the risk of developing antibodies against FVIII in an individual diagnosed with Hemophilia A comprising the steps of detecting the presence SNP rs4472605 in a biological sample from the individual; and predicting the risk of the individual of developing antibodies to FVIII. In one embodiment, the presence of SNP rs4472605 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4485556. In one embodiment, a method is provided for predicting the risk of developing antibodies against FVIII in an individual diagnosed with Hemophilia A comprising the steps of detecting the presence SNP rs4485556 in a biological sample from the individual; and predicting the risk of the individual of developing antibodies to FVIII. In one embodiment, the presence of SNP rs4485556 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4498385. In one embodiment, a method is provided for predicting the risk of developing antibodies against FVIII in an individual diagnosed with Hemophilia A comprising the steps of detecting the presence SNP rs4498385 in a biological sample from the individual; and predicting the risk of the individual of developing antibodies to FVIII. In one embodiment, the presence of SNP rs4498385 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4572808. In one embodiment, a method is provided for predicting the risk of developing antibodies against FVIII in an individual diagnosed with Hemophilia A comprising the steps of detecting the presence SNP rs4572808 in a biological sample from the individual; and predicting the risk of the individual of developing antibodies to FVIII. In one embodiment, the presence of SNP rs4572808 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4639174. In one embodiment, a method is provided for predicting the risk of developing antibodies against FVIII in an individual diagnosed with Hemophilia A comprising the steps of detecting the presence SNP rs4639174 in a biological sample from the individual; and predicting the risk of the individual of developing antibodies to FVIII. In one embodiment, the presence of SNP rs4639174 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4646077. In one embodiment, a method is provided for predicting the risk of developing antibodies against FVIII in an individual diagnosed with Hemophilia A comprising the steps of detecting the presence SNP rs4646077 in a biological sample from the individual; and predicting the risk of the individual of developing antibodies to FVIII. In one embodiment, the presence of SNP rs4646077 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4698806. In one embodiment, a method is provided for predicting the risk of developing antibodies against FVIII in an individual diagnosed with Hemophilia A comprising the steps of detecting the presence SNP rs4698806 in a biological sample from the individual; and predicting the risk of the individual of developing antibodies to FVIII. In one embodiment, the presence of SNP rs4698806 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4724231. In one embodiment, a method is provided for predicting the risk of developing antibodies against FVIII in an individual diagnosed with Hemophilia A comprising the steps of detecting the presence SNP rs4724231 in a biological sample from the individual; and predicting the risk of the individual of developing antibodies to FVIII. In one embodiment, the presence of SNP rs4724231 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4752894. In one embodiment, a method is provided for predicting the risk of developing antibodies against FVIII in an individual diagnosed with Hemophilia A comprising the steps of detecting the presence SNP rs4752894 in a biological sample from the individual; and predicting the risk of the individual of developing antibodies to FVIII. In one embodiment, the presence of SNP rs4752894 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4752896. In one embodiment, a method is provided for predicting the risk of developing antibodies against FVIII in an individual diagnosed with Hemophilia A comprising the steps of detecting the presence SNP rs4752896 in a biological sample from the individual; and predicting the risk of the individual of developing antibodies to FVIII. In one embodiment, the presence of SNP rs4752896 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4752904. In one embodiment, a method is provided for predicting the risk of developing antibodies against FVIII in an individual diagnosed with Hemophilia A comprising the steps of detecting the presence SNP rs4752904 in a biological sample from the individual; and predicting the risk of the individual of developing antibodies to FVIII. In one embodiment, the presence of SNP rs4752904 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4756331. In one embodiment, a method is provided for predicting the risk of developing antibodies against FVIII in an individual diagnosed with Hemophilia A comprising the steps of detecting the presence SNP rs4756331 in a biological sample from the individual; and predicting the risk of the individual of developing antibodies to FVIII. In one embodiment, the presence of SNP rs4756331 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4798598. In one embodiment, a method is provided for predicting the risk of developing antibodies against FVIII in an individual diagnosed with Hemophilia A comprising the steps of detecting the presence SNP rs4798598 in a biological sample from the individual; and predicting the risk of the individual of developing antibodies to FVIII. In one embodiment, the presence of SNP rs4798598 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4820059. In one embodiment, a method is provided for predicting the risk of developing antibodies against FVIII in an individual diagnosed with Hemophilia A comprising the steps of detecting the presence SNP rs4820059 in a biological sample from the individual; and predicting the risk of the individual of developing antibodies to FVIII. In one embodiment, the presence of SNP rs4820059 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4902264. In one embodiment, a method is provided for predicting the risk of developing antibodies against FVIII in an individual diagnosed with Hemophilia A comprising the steps of detecting the presence SNP rs4902264 in a biological sample from the individual; and predicting the risk of the individual of developing antibodies to FVIII. In one embodiment, the presence of SNP rs4902264 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4953292. In one embodiment, a method is provided for predicting the risk of developing antibodies against FVIII in an individual diagnosed with Hemophilia A comprising the steps of detecting the presence SNP rs4953292 in a biological sample from the individual; and predicting the risk of the individual of developing antibodies to FVIII. In one embodiment, the presence of SNP rs4953292 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4955104. In one embodiment, a method is provided for predicting the risk of developing antibodies against FVIII in an individual diagnosed with Hemophilia A comprising the steps of detecting the presence SNP rs4955104 in a biological sample from the individual; and predicting the risk of the individual of developing antibodies to FVIII. In one embodiment, the presence of SNP rs4955104 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4955272. In one embodiment, a method is provided for predicting the risk of developing antibodies against FVIII in an individual diagnosed with Hemophilia A comprising the steps of detecting the presence SNP rs4955272 in a biological sample from the individual; and predicting the risk of the individual of developing antibodies to FVIII. In one embodiment, the presence of SNP rs4955272 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs4966019. In one embodiment, a method is provided for predicting the risk of developing antibodies against FVIII in an individual diagnosed with Hemophilia A comprising the steps of detecting the presence SNP rs4966019 in a biological sample from the individual; and predicting the risk of the individual of developing antibodies to FVIII. In one embodiment, the presence of SNP rs4966019 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs496888. In one embodiment, a method is provided for predicting the risk of developing antibodies against FVIII in an individual diagnosed with Hemophilia A comprising the steps of detecting the presence SNP rs496888 in a biological sample from the individual; and predicting the risk of the individual of developing antibodies to FVIII. In one embodiment, the presence of SNP rs496888 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs499205. In one embodiment, a method is provided for predicting the risk of developing antibodies against FVIII in an individual diagnosed with Hemophilia A comprising the steps of detecting the presence SNP rs499205 in a biological sample from the individual; and predicting the risk of the individual of developing antibodies to FVIII. In one embodiment, the presence of SNP rs499205 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs509749. In one embodiment, a method is provided for predicting the risk of developing antibodies against FVIII in an individual diagnosed with Hemophilia A comprising the steps of detecting the presence SNP rs509749 in a biological sample from the individual; and predicting the risk of the individual of developing antibodies to FVIII. In one embodiment, the presence of SNP rs509749 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs5743220. In one embodiment, a method is provided for predicting the risk of developing antibodies against FVIII in an individual diagnosed with Hemophilia A comprising the steps of detecting the presence SNP rs5743220 in a biological sample from the individual; and predicting the risk of the individual of developing antibodies to FVIII. In one embodiment, the presence of SNP rs5743220 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs5743740. In one embodiment, a method is provided for predicting the risk of developing antibodies against FVIII in an individual diagnosed with Hemophilia A comprising the steps of detecting the presence SNP rs5743740 in a biological sample from the individual; and predicting the risk of the individual of developing antibodies to FVIII. In one embodiment, the presence of SNP rs5743740 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs5746154. In one embodiment, a method is provided for predicting the risk of developing antibodies against FVIII in an individual diagnosed with Hemophilia A comprising the steps of detecting the presence SNP rs5746154 in a biological sample from the individual; and predicting the risk of the individual of developing antibodies to FVIII. In one embodiment, the presence of SNP rs5746154 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs599563. In one embodiment, a method is provided for predicting the risk of developing antibodies against FVIII in an individual diagnosed with Hemophilia A comprising the steps of detecting the presence SNP rs599563 in a biological sample from the individual; and predicting the risk of the individual of developing antibodies to FVIII. In one embodiment, the presence of SNP rs599563 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs5996577. In one embodiment, a method is provided for predicting the risk of developing antibodies against FVIII in an individual diagnosed with Hemophilia A comprising the steps of detecting the presence SNP rs5996577 in a biological sample from the individual; and predicting the risk of the individual of developing antibodies to FVIII. In one embodiment, the presence of SNP rs5996577 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6016685. In one embodiment, a method is provided for predicting the risk of developing antibodies against FVIII in an individual diagnosed with Hemophilia A comprising the steps of detecting the presence SNP rs6016685 in a biological sample from the individual; and predicting the risk of the individual of developing antibodies to FVIII. In one embodiment, the presence of SNP rs6016685 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6021183. In one embodiment, a method is provided for predicting the risk of developing antibodies against FVIII in an individual diagnosed with Hemophilia A comprising the steps of detecting the presence SNP rs6021183 in a biological sample from the individual; and predicting the risk of the individual of developing antibodies to FVIII. In one embodiment, the presence of SNP rs6021183 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6058391. In one embodiment, a method is provided for predicting the risk of developing antibodies against FVIII in an individual diagnosed with Hemophilia A comprising the steps of detecting the presence SNP rs6058391 in a biological sample from the individual; and predicting the risk of the individual of developing antibodies to FVIII. In one embodiment, the presence of SNP rs6058391 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6060855. In one embodiment, a method is provided for predicting the risk of developing antibodies against FVIII in an individual diagnosed with Hemophilia A comprising the steps of detecting the presence SNP rs6060855 in a biological sample from the individual; and predicting the risk of the individual of developing antibodies to FVIII. In one embodiment, the presence of SNP rs6060855 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6065460. In one embodiment, a method is provided for predicting the risk of developing antibodies against FVIII in an individual diagnosed with Hemophilia A comprising the steps of detecting the presence SNP rs6065460 in a biological sample from the individual; and predicting the risk of the individual of developing antibodies to FVIII. In one embodiment, the presence of SNP rs6065460 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6065467. In one embodiment, a method is provided for predicting the risk of developing antibodies against FVIII in an individual diagnosed with Hemophilia A comprising the steps of detecting the presence SNP rs6065467 in a biological sample from the individual; and predicting the risk of the individual of developing antibodies to FVIII. In one embodiment, the presence of SNP rs6065467 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6093584. In one embodiment, a method is provided for predicting the risk of developing antibodies against FVIII in an individual diagnosed with Hemophilia A comprising the steps of detecting the presence SNP rs6093584 in a biological sample from the individual; and predicting the risk of the individual of developing antibodies to FVIII. In one embodiment, the presence of SNP rs6093584 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs613613. In one embodiment, a method is provided for predicting the risk of developing antibodies against FVIII in an individual diagnosed with Hemophilia A comprising the steps of detecting the presence SNP rs613613 in a biological sample from the individual; and predicting the risk of the individual of developing antibodies to FVIII. In one embodiment, the presence of SNP rs613613 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6214. In one embodiment, a method is provided for predicting the risk of developing antibodies against FVIII in an individual diagnosed with Hemophilia A comprising the steps of detecting the presence SNP rs6214 in a biological sample from the individual; and predicting the risk of the individual of developing antibodies to FVIII. In one embodiment, the presence of SNP rs6214 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs638251. In one embodiment, a method is provided for predicting the risk of developing antibodies against FVIII in an individual diagnosed with Hemophilia A comprising the steps of detecting the presence SNP rs638251 in a biological sample from the individual; and predicting the risk of the individual of developing antibodies to FVIII. In one embodiment, the presence of SNP rs638251 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6476985. In one embodiment, a method is provided for predicting the risk of developing antibodies against FVIII in an individual diagnosed with Hemophilia A comprising the steps of detecting the presence SNP rs6476985 in a biological sample from the individual; and predicting the risk of the individual of developing antibodies to FVIII. In one embodiment, the presence of SNP rs6476985 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6482644. In one embodiment, a method is provided for predicting the risk of developing antibodies against FVIII in an individual diagnosed with Hemophilia A comprising the steps of detecting the presence SNP rs6482644 in a biological sample from the individual; and predicting the risk of the individual of developing antibodies to FVIII. In one embodiment, the presence of SNP rs6482644 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6482647. In one embodiment, a method is provided for predicting the risk of developing antibodies against FVIII in an individual diagnosed with Hemophilia A comprising the steps of detecting the presence SNP rs6482647 in a biological sample from the individual; and predicting the risk of the individual of developing antibodies to FVIII. In one embodiment, the presence of SNP rs6482647 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6544865. In one embodiment, a method is provided for predicting the risk of developing antibodies against FVIII in an individual diagnosed with Hemophilia A comprising the steps of detecting the presence SNP rs6544865 in a biological sample from the individual; and predicting the risk of the individual of developing antibodies to FVIII. In one embodiment, the presence of SNP rs6544865 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6580942. In one embodiment, a method is provided for predicting the risk of developing antibodies against FVIII in an individual diagnosed with Hemophilia A comprising the steps of detecting the presence SNP rs6580942 in a biological sample from the individual; and predicting the risk of the individual of developing antibodies to FVIII. In one embodiment, the presence of SNP rs6580942 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs660597. In one embodiment, a method is provided for predicting the risk of developing antibodies against FVIII in an individual diagnosed with Hemophilia A comprising the steps of detecting the presence SNP rs660597 in a biological sample from the individual; and predicting the risk of the individual of developing antibodies to FVIII. In one embodiment, the presence of SNP rs660597 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6621980. In one embodiment, a method is provided for predicting the risk of developing antibodies against FVIII in an individual diagnosed with Hemophilia A comprising the steps of detecting the presence SNP rs6621980 in a biological sample from the individual; and predicting the risk of the individual of developing antibodies to FVIII. In one embodiment, the presence of SNP rs6621980 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6670616. In one embodiment, a method is provided for predicting the risk of developing antibodies against FVIII in an individual diagnosed with Hemophilia A comprising the steps of detecting the presence SNP rs6670616 in a biological sample from the individual; and predicting the risk of the individual of developing antibodies to FVIII. In one embodiment, the presence of SNP rs6670616 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6742576. In one embodiment, a method is provided for predicting the risk of developing antibodies against FVIII in an individual diagnosed with Hemophilia A comprising the steps of detecting the presence SNP rs6742576 in a biological sample from the individual; and predicting the risk of the individual of developing antibodies to FVIII. In one embodiment, the presence of SNP rs6742576 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6751395. In one embodiment, a method is provided for predicting the risk of developing antibodies against FVIII in an individual diagnosed with Hemophilia A comprising the steps of detecting the presence SNP rs6751395 in a biological sample from the individual; and predicting the risk of the individual of developing antibodies to FVIII. In one embodiment, the presence of SNP rs6751395 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6769530. In one embodiment, a method is provided for predicting the risk of developing antibodies against FVIII in an individual diagnosed with Hemophilia A comprising the steps of detecting the presence SNP rs6769530 in a biological sample from the individual; and predicting the risk of the individual of developing antibodies to FVIII. In one embodiment, the presence of SNP rs6769530 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6780432. In one embodiment, a method is provided for predicting the risk of developing antibodies against FVIII in an individual diagnosed with Hemophilia A comprising the steps of detecting the presence SNP rs6780432 in a biological sample from the individual; and predicting the risk of the individual of developing antibodies to FVIII. In one embodiment, the presence of SNP rs6780432 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6782288. In one embodiment, a method is provided for predicting the risk of developing antibodies against FVIII in an individual diagnosed with Hemophilia A comprising the steps of detecting the presence SNP rs6782288 in a biological sample from the individual; and predicting the risk of the individual of developing antibodies to FVIII. In one embodiment, the presence of SNP rs6782288 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6829390. In one embodiment, a method is provided for predicting the risk of developing antibodies against FVIII in an individual diagnosed with Hemophilia A comprising the steps of detecting the presence SNP rs6829390 in a biological sample from the individual; and predicting the risk of the individual of developing antibodies to FVIII. In one embodiment, the presence of SNP rs6829390 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6837303. In one embodiment, a method is provided for predicting the risk of developing antibodies against FVIII in an individual diagnosed with Hemophilia A comprising the steps of detecting the presence SNP rs6837303 in a biological sample from the individual; and predicting the risk of the individual of developing antibodies to FVIII. In one embodiment, the presence of SNP rs6837303 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6850557. In one embodiment, a method is provided for predicting the risk of developing antibodies against FVIII in an individual diagnosed with Hemophilia A comprising the steps of detecting the presence SNP rs6850557 in a biological sample from the individual; and predicting the risk of the individual of developing antibodies to FVIII. In one embodiment, the presence of SNP rs6850557 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6863088. In one embodiment, a method is provided for predicting the risk of developing antibodies against FVIII in an individual diagnosed with Hemophilia A comprising the steps of detecting the presence SNP rs6863088 in a biological sample from the individual; and predicting the risk of the individual of developing antibodies to FVIII. In one embodiment, the presence of SNP rs6863088 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs6917187. In one embodiment, a method is provided for predicting the risk of developing antibodies against FVIII in an individual diagnosed with Hemophilia A comprising the steps of detecting the presence SNP rs6917187 in a biological sample from the individual; and predicting the risk of the individual of developing antibodies to FVIII. In one embodiment, the presence of SNP rs6917187 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs704697. In one embodiment, a method is provided for predicting the risk of developing antibodies against FVIII in an individual diagnosed with Hemophilia A comprising the steps of detecting the presence SNP rs704697 in a biological sample from the individual; and predicting the risk of the individual of developing antibodies to FVIII. In one embodiment, the presence of SNP rs704697 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs704853. In one embodiment, a method is provided for predicting the risk of developing antibodies against FVIII in an individual diagnosed with Hemophilia A comprising the steps of detecting the presence SNP rs704853 in a biological sample from the individual; and predicting the risk of the individual of developing antibodies to FVIII. In one embodiment, the presence of SNP rs704853 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs706121. In one embodiment, a method is provided for predicting the risk of developing antibodies against FVIII in an individual diagnosed with Hemophilia A comprising the steps of detecting the presence SNP rs706121 in a biological sample from the individual; and predicting the risk of the individual of developing antibodies to FVIII. In one embodiment, the presence of SNP rs706121 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7072398. In one embodiment, a method is provided for predicting the risk of developing antibodies against FVIII in an individual diagnosed with Hemophilia A comprising the steps of detecting the presence SNP rs7072398 in a biological sample from the individual; and predicting the risk of the individual of developing antibodies to FVIII. In one embodiment, the presence of SNP rs7072398 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7099752. In one embodiment, a method is provided for predicting the risk of developing antibodies against FVIII in an individual diagnosed with Hemophilia A comprising the steps of detecting the presence SNP rs7099752 in a biological sample from the individual; and predicting the risk of the individual of developing antibodies to FVIII. In one embodiment, the presence of SNP rs7099752 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7124275. In one embodiment, a method is provided for predicting the risk of developing antibodies against FVIII in an individual diagnosed with Hemophilia A comprising the steps of detecting the presence SNP rs7124275 in a biological sample from the individual; and predicting the risk of the individual of developing antibodies to FVIII. In one embodiment, the presence of SNP rs7124275 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7130876. In one embodiment, a method is provided for predicting the risk of developing antibodies against FVIII in an individual diagnosed with Hemophilia A comprising the steps of detecting the presence SNP rs7130876 in a biological sample from the individual; and predicting the risk of the individual of developing antibodies to FVIII. In one embodiment, the presence of SNP rs7130876 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7170919. In one embodiment, a method is provided for predicting the risk of developing antibodies against FVIII in an individual diagnosed with Hemophilia A comprising the steps of detecting the presence SNP rs7170919 in a biological sample from the individual; and predicting the risk of the individual of developing antibodies to FVIII. In one embodiment, the presence of SNP rs7170919 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs717176. In one embodiment, a method is provided for predicting the risk of developing antibodies against FVIII in an individual diagnosed with Hemophilia A comprising the steps of detecting the presence SNP rs717176 in a biological sample from the individual; and predicting the risk of the individual of developing antibodies to FVIII. In one embodiment, the presence of SNP rs717176 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7246376. In one embodiment, a method is provided for predicting the risk of developing antibodies against FVIII in an individual diagnosed with Hemophilia A comprising the steps of detecting the presence SNP rs7246376 in a biological sample from the individual; and predicting the risk of the individual of developing antibodies to FVIII. In one embodiment, the presence of SNP rs7246376 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs728373. In one embodiment, a method is provided for predicting the risk of developing antibodies against FVIII in an individual diagnosed with Hemophilia A comprising the steps of detecting the presence SNP rs728373 in a biological sample from the individual; and predicting the risk of the individual of developing antibodies to FVIII. In one embodiment, the presence of SNP rs728373 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7289754. In one embodiment, a method is provided for predicting the risk of developing antibodies against FVIII in an individual diagnosed with Hemophilia A comprising the steps of detecting the presence SNP rs7289754 in a biological sample from the individual; and predicting the risk of the individual of developing antibodies to FVIII. In one embodiment, the presence of SNP rs7289754 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7290696. In one embodiment, a method is provided for predicting the risk of developing antibodies against FVIII in an individual diagnosed with Hemophilia A comprising the steps of detecting the presence SNP rs7290696 in a biological sample from the individual; and predicting the risk of the individual of developing antibodies to FVIII. In one embodiment, the presence of SNP rs7290696 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs731305. In one embodiment, a method is provided for predicting the risk of developing antibodies against FVIII in an individual diagnosed with Hemophilia A comprising the steps of detecting the presence SNP rs731305 in a biological sample from the individual; and predicting the risk of the individual of developing antibodies to FVIII. In one embodiment, the presence of SNP rs731305 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7348444. In one embodiment, a method is provided for predicting the risk of developing antibodies against FVIII in an individual diagnosed with Hemophilia A comprising the steps of detecting the presence SNP rs7348444 in a biological sample from the individual; and predicting the risk of the individual of developing antibodies to FVIII. In one embodiment, the presence of SNP rs7348444 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7359387. In one embodiment, a method is provided for predicting the risk of developing antibodies against FVIII in an individual diagnosed with Hemophilia A comprising the steps of detecting the presence SNP rs7359387 in a biological sample from the individual; and predicting the risk of the individual of developing antibodies to FVIII. In one embodiment, the presence of SNP rs7359387 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7541717. In one embodiment, a method is provided for predicting the risk of developing antibodies against FVIII in an individual diagnosed with Hemophilia A comprising the steps of detecting the presence SNP rs7541717 in a biological sample from the individual; and predicting the risk of the individual of developing antibodies to FVIII. In one embodiment, the presence of SNP rs7541717 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7559522. In one embodiment, a method is provided for predicting the risk of developing antibodies against FVIII in an individual diagnosed with Hemophilia A comprising the steps of detecting the presence SNP rs7559522 in a biological sample from the individual; and predicting the risk of the individual of developing antibodies to FVIII. In one embodiment, the presence of SNP rs7559522 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs763361. In one embodiment, a method is provided for predicting the risk of developing antibodies against FVIII in an individual diagnosed with Hemophilia A comprising the steps of detecting the presence SNP rs763361 in a biological sample from the individual; and predicting the risk of the individual of developing antibodies to FVIII. In one embodiment, the presence of SNP rs763361 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7641625. In one embodiment, a method is provided for predicting the risk of developing antibodies against FVIII in an individual diagnosed with Hemophilia A comprising the steps of detecting the presence SNP rs7641625 in a biological sample from the individual; and predicting the risk of the individual of developing antibodies to FVIII. In one embodiment, the presence of SNP rs7641625 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7647903. In one embodiment, a method is provided for predicting the risk of developing antibodies against FVIII in an individual diagnosed with Hemophilia A comprising the steps of detecting the presence SNP rs7647903 in a biological sample from the individual; and predicting the risk of the individual of developing antibodies to FVIII. In one embodiment, the presence of SNP rs7647903 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs766502. In one embodiment, a method is provided for predicting the risk of developing antibodies against FVIII in an individual diagnosed with Hemophilia A comprising the steps of detecting the presence SNP rs766502 in a biological sample from the individual; and predicting the risk of the individual of developing antibodies to FVIII. In one embodiment, the presence of SNP rs766502 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7690305. In one embodiment, a method is provided for predicting the risk of developing antibodies against FVIII in an individual diagnosed with Hemophilia A comprising the steps of detecting the presence SNP rs7690305 in a biological sample from the individual; and predicting the risk of the individual of developing antibodies to FVIII. In one embodiment, the presence of SNP rs7690305 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7692976. In one embodiment, a method is provided for predicting the risk of developing antibodies against FVIII in an individual diagnosed with Hemophilia A comprising the steps of detecting the presence SNP rs7692976 in a biological sample from the individual; and predicting the risk of the individual of developing antibodies to FVIII. In one embodiment, the presence of SNP rs7692976 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP 146106438. In one embodiment, a method is provided for predicting the risk of developing antibodies against FVIII in an individual diagnosed with Hemophilia A comprising the steps of detecting the presence SNP 146106438 in a biological sample from the individual; and predicting the risk of the individual of developing antibodies to FVIII. In one embodiment, the presence of SNP 146106438 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7732671. In one embodiment, a method is provided for predicting the risk of developing antibodies against FVIII in an individual diagnosed with Hemophilia A comprising the steps of detecting the presence SNP rs7732671 in a biological sample from the individual; and predicting the risk of the individual of developing antibodies to FVIII. In one embodiment, the presence of SNP rs7732671 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7851161. In one embodiment, a method is provided for predicting the risk of developing antibodies against FVIII in an individual diagnosed with Hemophilia A comprising the steps of detecting the presence SNP rs7851161 in a biological sample from the individual; and predicting the risk of the individual of developing antibodies to FVIII. In one embodiment, the presence of SNP rs7851161 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs791587. In one embodiment, a method is provided for predicting the risk of developing antibodies against FVIII in an individual diagnosed with Hemophilia A comprising the steps of detecting the presence SNP rs791587 in a biological sample from the individual; and predicting the risk of the individual of developing antibodies to FVIII. In one embodiment, the presence of SNP rs791587 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs793816. In one embodiment, a method is provided for predicting the risk of developing antibodies against FVIII in an individual diagnosed with Hemophilia A comprising the steps of detecting the presence SNP rs793816 in a biological sample from the individual; and predicting the risk of the individual of developing antibodies to FVIII. In one embodiment, the presence of SNP rs793816 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs7987909. In one embodiment, a method is provided for predicting the risk of developing antibodies against FVIII in an individual diagnosed with Hemophilia A comprising the steps of detecting the presence SNP rs7987909 in a biological sample from the individual; and predicting the risk of the individual of developing antibodies to FVIII. In one embodiment, the presence of SNP rs7987909 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs8005905. In one embodiment, a method is provided for predicting the risk of developing antibodies against FVIII in an individual diagnosed with Hemophilia A comprising the steps of detecting the presence SNP rs8005905 in a biological sample from the individual; and predicting the risk of the individual of developing antibodies to FVIII. In one embodiment, the presence of SNP rs8005905 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs805274. In one embodiment, a method is provided for predicting the risk of developing antibodies against FVIII in an individual diagnosed with Hemophilia A comprising the steps of detecting the presence SNP rs805274 in a biological sample from the individual; and predicting the risk of the individual of developing antibodies to FVIII. In one embodiment, the presence of SNP rs805274 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs805287. In one embodiment, a method is provided for predicting the risk of developing antibodies against FVIII in an individual diagnosed with Hemophilia A comprising the steps of detecting the presence SNP rs805287 in a biological sample from the individual; and predicting the risk of the individual of developing antibodies to FVIII. In one embodiment, the presence of SNP rs805287 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs8064821. In one embodiment, a method is provided for predicting the risk of developing antibodies against FVIII in an individual diagnosed with Hemophilia A comprising the steps of detecting the presence SNP rs8064821 in a biological sample from the individual; and predicting the risk of the individual of developing antibodies to FVIII. In one embodiment, the presence of SNP rs8064821 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs8078439. In one embodiment, a method is provided for predicting the risk of developing antibodies against FVIII in an individual diagnosed with Hemophilia A comprising the steps of detecting the presence SNP rs8078439 in a biological sample from the individual; and predicting the risk of the individual of developing antibodies to FVIII. In one embodiment, the presence of SNP rs8078439 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs8086815. In one embodiment, a method is provided for predicting the risk of developing antibodies against FVIII in an individual diagnosed with Hemophilia A comprising the steps of detecting the presence SNP rs8086815 in a biological sample from the individual; and predicting the risk of the individual of developing antibodies to FVIII. In one embodiment, the presence of SNP rs8086815 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs831603. In one embodiment, a method is provided for predicting the risk of developing antibodies against FVIII in an individual diagnosed with Hemophilia A comprising the steps of detecting the presence SNP rs831603 in a biological sample from the individual; and predicting the risk of the individual of developing antibodies to FVIII. In one embodiment, the presence of SNP rs831603 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs832517. In one embodiment, a method is provided for predicting the risk of developing antibodies against FVIII in an individual diagnosed with Hemophilia A comprising the steps of detecting the presence SNP rs832517 in a biological sample from the individual; and predicting the risk of the individual of developing antibodies to FVIII. In one embodiment, the presence of SNP rs832517 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs866484. In one embodiment, a method is provided for predicting the risk of developing antibodies against FVIII in an individual diagnosed with Hemophilia A comprising the steps of detecting the presence SNP rs866484 in a biological sample from the individual; and predicting the risk of the individual of developing antibodies to FVIII. In one embodiment, the presence of SNP rs866484 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs872071. In one embodiment, a method is provided for predicting the risk of developing antibodies against FVIII in an individual diagnosed with Hemophilia A comprising the steps of detecting the presence SNP rs872071 in a biological sample from the individual; and predicting the risk of the individual of developing antibodies to FVIII. In one embodiment, the presence of SNP rs872071 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs875258. In one embodiment, a method is provided for predicting the risk of developing antibodies against FVIII in an individual diagnosed with Hemophilia A comprising the steps of detecting the presence SNP rs875258 in a biological sample from the individual; and predicting the risk of the individual of developing antibodies to FVIII. In one embodiment, the presence of SNP rs875258 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs878081. In one embodiment, a method is provided for predicting the risk of developing antibodies against FVIII in an individual diagnosed with Hemophilia A comprising the steps of detecting the presence SNP rs878081 in a biological sample from the individual; and predicting the risk of the individual of developing antibodies to FVIII. In one embodiment, the presence of SNP rs878081 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs896769. In one embodiment, a method is provided for predicting the risk of developing antibodies against FVIII in an individual diagnosed with Hemophilia A comprising the steps of detecting the presence SNP rs896769 in a biological sample from the individual; and predicting the risk of the individual of developing antibodies to FVIII. In one embodiment, the presence of SNP rs896769 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs910682. In one embodiment, a method is provided for predicting the risk of developing antibodies against FVIII in an individual diagnosed with Hemophilia A comprising the steps of detecting the presence SNP rs910682 in a biological sample from the individual; and predicting the risk of the individual of developing antibodies to FVIII. In one embodiment, the presence of SNP rs910682 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs926479. In one embodiment, a method is provided for predicting the risk of developing antibodies against FVIII in an individual diagnosed with Hemophilia A comprising the steps of detecting the presence SNP rs926479 in a biological sample from the individual; and predicting the risk of the individual of developing antibodies to FVIII. In one embodiment, the presence of SNP rs926479 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs927010. In one embodiment, a method is provided for predicting the risk of developing antibodies against FVIII in an individual diagnosed with Hemophilia A comprising the steps of detecting the presence SNP rs927010 in a biological sample from the individual; and predicting the risk of the individual of developing antibodies to FVIII. In one embodiment, the presence of SNP rs927010 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs927335. In one embodiment, a method is provided for predicting the risk of developing antibodies against FVIII in an individual diagnosed with Hemophilia A comprising the steps of detecting the presence SNP rs927335 in a biological sample from the individual; and predicting the risk of the individual of developing antibodies to FVIII. In one embodiment, the presence of SNP rs927335 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9310940. In one embodiment, a method is provided for predicting the risk of developing antibodies against FVIII in an individual diagnosed with Hemophilia A comprising the steps of detecting the presence SNP rs9310940 in a biological sample from the individual; and predicting the risk of the individual of developing antibodies to FVIII. In one embodiment, the presence of SNP rs9310940 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9313487. In one embodiment, a method is provided for predicting the risk of developing antibodies against FVIII in an individual diagnosed with Hemophilia A comprising the steps of detecting the presence SNP rs9313487 in a biological sample from the individual; and predicting the risk of the individual of developing antibodies to FVIII. In one embodiment, the presence of SNP rs9313487 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs933226. In one embodiment, a method is provided for predicting the risk of developing antibodies against FVIII in an individual diagnosed with Hemophilia A comprising the steps of detecting the presence SNP rs933226 in a biological sample from the individual; and predicting the risk of the individual of developing antibodies to FVIII. In one embodiment, the presence of SNP rs933226 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9426315. In one embodiment, a method is provided for predicting the risk of developing antibodies against FVIII in an individual diagnosed with Hemophilia A comprising the steps of detecting the presence SNP rs9426315 in a biological sample from the individual; and predicting the risk of the individual of developing antibodies to FVIII. In one embodiment, the presence of SNP rs9426315 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9482888. In one embodiment, a method is provided for predicting the risk of developing antibodies against FVIII in an individual diagnosed with Hemophilia A comprising the steps of detecting the presence SNP rs9482888 in a biological sample from the individual; and predicting the risk of the individual of developing antibodies to FVIII. In one embodiment, the presence of SNP rs9482888 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9487735. In one embodiment, a method is provided for predicting the risk of developing antibodies against FVIII in an individual diagnosed with Hemophilia A comprising the steps of detecting the presence SNP rs9487735 in a biological sample from the individual; and predicting the risk of the individual of developing antibodies to FVIII. In one embodiment, the presence of SNP rs9487735 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs949664. In one embodiment, a method is provided for predicting the risk of developing antibodies against FVIII in an individual diagnosed with Hemophilia A comprising the steps of detecting the presence SNP rs949664 in a biological sample from the individual; and predicting the risk of the individual of developing antibodies to FVIII. In one embodiment, the presence of SNP rs949664 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs970283. In one embodiment, a method is provided for predicting the risk of developing antibodies against FVIII in an individual diagnosed with Hemophilia A comprising the steps of detecting the presence SNP rs970283 in a biological sample from the individual; and predicting the risk of the individual of developing antibodies to FVIII. In one embodiment, the presence of SNP rs970283 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs976881. In one embodiment, a method is provided for predicting the risk of developing antibodies against FVIII in an individual diagnosed with Hemophilia A comprising the steps of detecting the presence SNP rs976881 in a biological sample from the individual; and predicting the risk of the individual of developing antibodies to FVIII. In one embodiment, the presence of SNP rs976881 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9817149. In one embodiment, a method is provided for predicting the risk of developing antibodies against FVIII in an individual diagnosed with Hemophilia A comprising the steps of detecting the presence SNP rs9817149 in a biological sample from the individual; and predicting the risk of the individual of developing antibodies to FVIII. In one embodiment, the presence of SNP rs9817149 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9826296. In one embodiment, a method is provided for predicting the risk of developing antibodies against FVIII in an individual diagnosed with Hemophilia A comprising the steps of detecting the presence SNP rs9826296 in a biological sample from the individual; and predicting the risk of the individual of developing antibodies to FVIII. In one embodiment, the presence of SNP rs9826296 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9831803. In one embodiment, a method is provided for predicting the risk of developing antibodies against FVIII in an individual diagnosed with Hemophilia A comprising the steps of detecting the presence SNP rs9831803 in a biological sample from the individual; and predicting the risk of the individual of developing antibodies to FVIII. In one embodiment, the presence of SNP rs9831803 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9862163. In one embodiment, a method is provided for predicting the risk of developing antibodies against FVIII in an individual diagnosed with Hemophilia A comprising the steps of detecting the presence SNP rs9862163 in a biological sample from the individual; and predicting the risk of the individual of developing antibodies to FVIII. In one embodiment, the presence of SNP rs9862163 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9867325. In one embodiment, a method is provided for predicting the risk of developing antibodies against FVIII in an individual diagnosed with Hemophilia A comprising the steps of detecting the presence SNP rs9867325 in a biological sample from the individual; and predicting the risk of the individual of developing antibodies to FVIII. In one embodiment, the presence of SNP rs9867325 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9892152. In one embodiment, a method is provided for predicting the risk of developing antibodies against FVIII in an individual diagnosed with Hemophilia A comprising the steps of detecting the presence SNP rs9892152 in a biological sample from the individual; and predicting the risk of the individual of developing antibodies to FVIII. In one embodiment, the presence of SNP rs9892152 is predictive of an increased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

In one embodiment, the present invention provides a marker useful for predicting the risk of developing antibodies against FVIII in an individual diagnosed with Hemophilia A consisting of SNP rs9991904. In one embodiment, a method is provided for predicting the risk of developing antibodies against FVIII in an individual diagnosed with Hemophilia A comprising the steps of detecting the presence SNP rs9991904 in a biological sample from the individual; and predicting the risk of the individual of developing antibodies to FVIII. In one embodiment, the presence of SNP rs9991904 is predictive of a decreased risk of developing antibodies against Factor VIII. In one embodiment, the method further comprises assigning a therapy comprising administration of Factor VIII to the individual. In another embodiment, the method further comprises assigning a therapy comprising Factor VIII bypass therapy to the individual. In another embodiment, the method further comprises increasing a dosage of a therapy comprising administration of FVIII to be administered to the individual. In another embodiment, the method further comprises decreasing a dosage of a therapy comprising administration of FVIII to be administered to the individual. In another embodiment, the method further comprises detecting the presence of at least a second SNP selected from the group consisting of the SNPs listed in Tables 1, 2, 3, and 4. In another embodiment, the method further comprises detecting the presence of at least 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, or more SNPs selected from the group consisting of the SNPs listed in Tables 1, 2, 3, and 4.

C. Methods for Detecting SNPs

The present invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)). Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

Any suitable method can be used to detect (i.e. screen for or identify) a SNP, e.g., restriction fragment length polymorphisms and electrophoretic gel analysis or mass spectroscopy, or PCR analysis. Various real-time PCR methods can be used to detect SNPs, including, e.g., Taqman or molecular beacon-based assays (e.g., U.S. Pat. Nos. 5,210,015; 5,487,972; Tyagi et al., Nature Biotechnology 14:303 (1996); and PCT WO 95/13399) are useful to monitor for the presence of absence of a SNP. Additional SNP detection methods include, e.g., DNA sequencing, sequencing by hybridization, dot blotting, oligonucleotide array (DNA chip or bead chip) hybridization analysis, or are described in, e.g., U.S. Pat. No. 6,177,249; Landegren et al., Genome Research, 8:769-776 (1998); Botstein et al., Am J Human Genetics 32:314-331 (1980); Meyers et al., Methods in Enzymology 155:501-527 (1987); Keen et al., Trends in Genetics 7:5 (1991); Myers et al., Science 230:1242-1246 (1985); and Kwok et al., Genomics 23:138-144 (1994).

Analysis of the genotype of an nucleic acid marker can be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), and sequencing by hybridization (Chee et al., *Science*, 274:610-614 (1996); Drmanac et al., *Science*, 260:1649-1652 (1993); Drmanac et al., *Nature Biotech.*, 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for genotyping a subject at a polymorphic site include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE) and pyrosequencing.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocyante (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) *Science*, 251: 767-777; Sheldon et al. (1993) *Clinical Chemistry* 39(4): 718-719, and Kozal et al. (1996) *Nature Medicine* 2(7): 753-759.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system, in particular RT-PCR or real time PCR, and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation.

In some embodiments of the present invention, the target nucleic acid or the probe is immobilized on a solid support. Solid supports suitable for use in the assays of the invention are known to those of skill in the art. As used herein, a solid support is a matrix of material in a substantially fixed arrangement. One preferred example is the Illumina® BeadChip array. The array comprises silica beads which are self-assembled into ordered microwells. Each 3 μm silica bead comprises a plurality of 50 mer, transcript-specific oligonucleotide probes that have been immobilized on the bead. To generate a BeadChip, thousands to tens of thousands of unique oligonucleotides, each complementary to a different target sequence, are synthesized. These oligos are then immobilized in separate reactions to the beads, generating a corresponding number of unique bead types. The beads are pooled together, and then loaded by a self-assembly process into microwells that have been etched into the surface of a BeadChip. Each bead type is represented on the array surface an average of more than thirty times.

In some embodiments, the identification of a single nucleotide polymorphism of the present invention is accomplished through the use of a whole-genome amplification method. One preferred example is the Illumina® Infinium® assay. Briefly, 750 ng of human genomic DNA is isothermally amplified overnight. The amplified product is then fragmented by a controlled enzymatic digestion. The DNA is then precipitated and resuspended and applied to a BeadChip that has been prepared for hybridization. DNA samples are applied to the BeadChip and incubated overnight. The amplified and fragmented DNA samples anneal to locus-specific 50-mers (on beads). Each bead type corresponds to each allele per SNP locus. After hybridization, allelic specificity is conferred by enzymatic base extension and revealed by fluorescent staining.

IV. Compositions, Kits, and Arrays

The invention also provides compositions, kits, and arrays for practicing the methods described herein using polynucleotides of the invention.

In some embodiments, the oligonucleotides, kits, and arrays of the present invention may be used to predict the risk of an individual developing antibodies to factor VIII (FVIII) and to adjust a dosage of FVIII therapy received by the individual. In some embodiments, the oligonucleotides, kits, and arrays of the present invention may be used to predict the risk of an individual developing antibodies to FVIII and to adjust a dosage of bypass therapy received by the individual.

A. Probes

In exemplary embodiments, a kit described herein comprises a capture probe or capture probe set. Capture probes sets comprise a plurality of "capture probes," which are compounds used to detect the presence or absence of, or to quantify, relatively or absolutely, a target species or target sequence. Generally, a capture probe allows the attachment of a target sequence to a solid support for the purposes of detection as further described herein. Attachment of the target species to the capture binding ligand can be direct or indirect and can be covalent or noncovalent. Capture probes that bind directly to a target species may be said to be "selective" for, "specifically bind" or "selectively bind" their target. It should be noted that capture probes are designed to be perfectly or substantially complementary to either of the strands (e.g. either the sense or the antisense strand) of a double stranded polynucleotide, such as a gene. Thus, in some cases, a capture probe described herein is perfectly or substantially complementary to the sense strand; that is, assuming the sense strand is referred to as "Watson", the capture probe would be "Crick". In some cases, a capture probe described herein is perfectly or substantially complementary to the antisense strand. For detecting a SNP, a capture probe selective for an allele of a gene typically spans the one or more nucleic acids that differs from corresponding nucleic acids in a different allele of a gene. For detecting an insertion, a capture probe selective for an allele of a gene typically spans one or more nucleic acids that are present compared to the corresponding site in a different allele of a gene in which the nucleic acids are absent. For detecting a deletion, a capture probe selective for an allele of a gene typically spans a site where one or more nucleic acids are absent compared to the corresponding site in a different allele of a gene in which the nucleic acids are present.

Capture probes that "selectively bind" to or are "selective" for (i.e., are "complementary" or "substantially complementary" to) a target nucleic acid find use in the present invention. "Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules may be said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98% to 100%, and in some embodiments, at least a percentage selected from 90%, 91%, 92%, 93%, 94%, 95%, 96%, 97%, 98% and 99%. Where one single stranded RNA or DNA molecule is shorter than another, the two single stranded RNA or DNA molecules may be said to be substantially complementary when the nucleotides of the longer strand, optimally aligned and compared and with appropriate nucleotide insertions or deletions, pair with at least about 80% of the nucleotides of the shorter strand, usually at least about 90% to 95%, and more preferably from about 98% to 100%, and in some embodiments, at least a percentage selected from 90%, 91%, 92%, 93%, 94%, 95%, 96%, 97%, 98% and 99%. Alternatively, substantial complementarity exists (i.e., one sequence is selective for another) when an RNA or DNA strand will hybridize under selective hybridization conditions (for example, stringent conditions or high stringency conditions as known in the art) to its complement. Typically, selective hybridization will occur when there is at least about 65% complementarity over a stretch of at least 14 to 25 nucleotides, preferably at least about 75%, more preferably at least about 90% (or 91%, 92%, 93%, 94%, 95%, 96%, 97%, 98% or 99%) complementarity. (See, M. Kanehisa, Nucleic Acids Res., 2004, 12: 203.) In some embodiments, the term "bind" refers to binding under high stringency conditions. In some embodiments, a capture probe that selectively binds to or is selective for a target is perfectly complementary to the target. In some embodiments, a capture probe that selectively binds to or is selective for a target is substantially complementary to the target.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one embodiment, stable duplex means that a duplex structure is not destroyed by a stringent wash, e.g., conditions including temperature of about 5° C. less than the $T_m$ of a strand of the duplex and low monovalent salt concentration, e.g. less than 0.2 M, or less than 0.1 M. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" includes the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

In exemplary embodiments, each of the probes of a capture probe set is suitable for distinguishing at least two different alleles of a given gene (e.g., a SNP associated with a risk risk of developing antibodies against Factor VIII (FVIII) in an individual diagnosed with Hemophilia A). The probes or capture probe sets described herein can be used to determine a polymorphism at a gene locus. As understood in the art, an "allele" refers to a particular alternative form of a gene. For convenience, the term "allele" as used herein can also refer to a combination of alleles at multiple loci that are transmitted together on the same chromosome. That is, an allele can refer to a haplotype. An allele can be characterized, for example, by substitution, insertion or deletion of one or more bases relative to a different allele. A capture probe could thus, in various examples, span a polymorphic site of the gene, span one or more insertions or span nucleic acids flanking a deletion.

An allele may be referred to in various ways. For example, an allele may be referred to by a substitution of a nucleotide for another in a parent polynucleotide strand (e.g., genomic DNA, mRNA, fragments thereof, amplification products thereof and other polynucleotides disclosed herein) or by the substitution of an amino acid for another in a parent polypeptide strand (e.g., a polypeptide resulting from translation of a polynucleotide). In some instances, a reference to an amino acid substitution corresponds to a nucleotide variation in the gene that causes that amino acid substitution in the polypeptide resulting from expression of the gene as understood in the art. Where reference is made to a substitution, both a parent molecule (e.g., gene) and a molecule containing the substitution relative to the parent are contemplated and either or both alleles may be probed. Where reference is made to an insertion, both a parent molecule (e.g., gene) and a molecule containing the insertion relative to the parent is contemplated and either or both alleles may be probed. Where reference is made to a deletion, both a parent molecule (e.g., gene) and a molecule containing the deletion relative to the parent is contemplated and either or both alleles may be probed.

In one embodiment, a capture probe set comprises a probe that is selective for an allele of a gene, (e.g., a gene associated with a SNP listed in any one of Tables 1 to 4). In one embodiment, a capture probe set comprises a pair of probes, one of which is selective for a first allele of a gene and one of which is selective for a second allele of the gene. In some embodiments, a capture probe set comprises a pair of probes, one of which is selective for a wildtype allele of the gene and one of which is selective for a mutant (or "variant") allele of the gene. The term "wildtype" can in some embodiments refer to a major allele or an allele that is the most frequently occurring allele. The term "variant" can in some embodiments refer to a minor allele or an allele that is not the most frequently occurring allele. In exemplary embodiments, a capture probe set comprises a pair of probes, one of which is selective for a major allele of the gene and one of which is selective for a minor allele of the gene. In some embodiments, a capture probe set comprises more than two probes, each of which is selective for a different allele of the gene. In exemplary embodiments, a capture probe set comprises one or more probes selective for one or more alleles of one or more genes.

In some embodiments, one or more capture probes are used to identify the base at a detection position. In these embodiments, each different probe comprises a different base at an "interrogation position," which will differentially hybridize to a base at the detection position of the target sequence. By using different probes, each with a different base at the interrogation position, the identification of the base at the detection position is elucidated.

In one embodiment, all nucleotides outside of the interrogation position in two or more probes are the same as compared between the probes; that is, in some embodiments it is preferable to use probes that have equal all components other than the interrogation position (e.g., both the length of the probes as well as the non-interrogation bases) to allow good discrimination. In some embodiments, it may be desirable to alter other components, in order to maximize discrimination at the detection position. For example, all nucleotides outside of the interrogation position in two probes may be the same except for one or two nucleic acids added to the end of only one probe.

B. Oligonucleotides

The invention provides compositions comprising oligonucleotides for practicing the detection and prediction methods of the invention. The oligonucleotides typically are from 10 to 60 nucleotides in length. In some embodiments, the oligonucleotide is about 45-60 nucleotides in length. Each oligonucleotide is complementary to a target sequence of interest. In some embodiments, the oligonucleotide is complementary to a target sequence of interest that comprises a SNP selected from the group consisting of the SNPs listed in Table 1. In some embodiments, the oligonucleotide is complementary to a target sequence of interest that comprises a SNP located in a gene selected from the group consisting of DOCK2, MAPK9, F13A1, CD36, and PTPRR. In some embodiments, the oligonucleotide is complementary to a target sequence of interest that comprises a SNP selected from the group consisting of rs11744216, rs13206518, rs3211834, rs1863993, rs4147385, and rs1567748.

C. Diagnostic Kits

The invention also provides kits for carrying out the detection and prediction methods of the invention. The kits comprise at least one or more allele-specific oligonucleotide for the SNP described in Table 1. Diagnostic kits for SNPs generally include means of identifying the SNP, e.g., oligonucleotides suitable for amplifying the SNP and directions for detection. Primers can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50 or more nucleotides in length.

The kits may include several oligonucleotide sequences to detect at least one single nucleotide polymorphism (SNP) of the invention, e.g., a first oligonucleotide sequence and/or second and/or third and/or additional oligonucleotides that detect at least one SNP selected from the group consisting of the SNPs listed in Table 1, the SNPs listed in Table 2, the SNPs listed in Table 3, and the SPNs listed in Table 4. Optional additional components of the kit include, for example, positive and negative controls, restriction enzymes, reverse-transcriptase or polymerase, the substrate nucleoside triphosphates, means used to label (for example, an avidinenzyme conjugate and enzyme substrate and chromogen if the label is biotin), and the appropriate buffers for reverse transcription, PCR, or hybridization reactions.

In some embodiments, the kits may include one or more oligonucleotide sequences to detect at least one SNP selected from the group consisting of rs11744216, rs13206518, rs3211834, rs1863993, rs4147385, and rs1567748.

In one embodiment, the present invention provides a diagnostic kit for predicting the risk of developing antibodies against Factor VIII (FVIII) in an individual diagnosed with Hemophilia, the kit comprising at least one oligonucleotide capable of being used to detect at least one single nucleotide polymorphism (SNP) selected from the group consisting of a SNP listed in Table 1, a SNP listed in Table 2, a SNP listed in Table 3, and a SNP listed in Table 4. In a preferred embodiment, the at least one SNP is selected from those listed in Table 3. In another preferred embodiment, the at least one SNP is selected from the group consisting of rs12368829, rs11744216, rs1863993, rs4147385, rs12546235, rs4242389, rs10054825, rs17535213, rs10072056, and rs17725712. In one embodiment, the oligonucleotide capable of being used to detect at least one SNP comprises a sequence complementary to a genomic sequence flanking the SNP. In a specific embodiment, the oligonucleotide sequence that is complementary to the genomic sequence that flanks a SNP includes a nucleotide corresponding to the position of the SNP in the genome. In one embodiment, the nucleotide corresponding to the position of the SNP in the genome is the rare nucleotide (i.e., the SNP). In another embodiment, the nucleotide corresponding to the position of the SNP in the genome is the wild type nucleotide.

In another embodiment, the present invention provides a diagnostic kit for predicting the risk of developing antibodies against Factor VIII (FVIII) in an individual diagnosed with severe Hemophilia, the kit comprising at least one oligonucleotide capable of being used to detect at least one single nucleotide polymorphism (SNP) selected from the group consisting of a SNP listed in Table 2 and a SNP listed in Table 4. In a preferred embodiment, the at least one SNP is selected from those listed in Table 4. In another preferred embodiment, the at least one SNP is selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888. In one embodiment, the oligonucleotide capable of being used to detect at least one SNP comprises a sequence complementary to a genomic sequence flanking the SNP. In a specific embodiment, the oligonucleotide sequence that is complementary to the genomic sequence that flanks a SNP includes a nucleotide corresponding to the position of the SNP in the genome. In one embodiment, the nucleotide corresponding to the position of the SNP in the genome is the rare nucleotide (i.e., the SNP). In another embodiment, the nucleotide corresponding to the position of the SNP in the genome is the wild type nucleotide.

D. Oligonucleotide Arrays

The invention also provides assay compositions for use in solid phase assays; such compositions can include, for example, one or more polynucleotides of the invention immobilized on a solid support, and a labeling reagent. In each case, the assay compositions can also include additional reagents that are desirable for hybridization. In preferred embodiments, the solid phase assay is a microarray comprising a support having a plurality of discrete regions, wherein each discrete region comprises one or more nucleic acid fragments spotted thereon. In some embodiments, the one or more nucleic acid fragments spotted on the microarray support comprises a sequence that is complementary to a SNP selected from the group consisting of the SNPs listed in Table 1.

In one embodiment, the invention provides a microarray for predicting the risk of developing antibodies against Factor VIII (FVIII) in an individual diagnosed with Hemophilia, the microarray comprising a support having a plurality of discrete regions, each discrete region having a nucleic acid fragment spotted thereon, wherein at least one nucleic acid fragment spotted on the support comprises a sequence that is complementary to a genomic sequence that flanks a single nucleotide polymorphism (SNP) selected from the group consisting of a SNP listed in Table 1, a SNP listed in Table 2, a SNP listed in Table 3, and a SNP listed in Table 4. In a preferred embodiment, the at least one SNP is selected from those listed in Table 3. In another preferred embodiment, the at least one SNP is selected from the group consisting of rs12368829, rs11744216, rs1863993, rs4147385, rs12546235, rs4242389, rs10054825, rs17535213, rs10072056, and rs17725712. In one embodiment, the oligonucleotide capable of being used to detect at least one SNP comprises a sequence complementary to a genomic sequence flanking the SNP. In a specific embodiment, the oligonucleotide sequence that is complementary to the genomic sequence that flanks a SNP includes a nucleotide corresponding to the position of the SNP in the genome. In one embodiment, the nucleotide corresponding to the position of the SNP in the genome is the rare nucleotide (i.e., the SNP). In another embodiment, the nucleotide corresponding to the position of the SNP in the genome is the wild type nucleotide.

In certain embodiments, the microarray comprises at least 2 nucleic acid fragments comprising a sequence that is complementary to a genomic sequence that flanks a single nucleotide polymorphism (SNP) listed in Tables 1 to 4, or at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, more, or all of the SNPs listed in Tables 1 to 4. In a preferred embodiment, the SNPs are selected from those listed in Tables 1 and 3. In another preferred embodiment, the SNPs are selected from those listed in Table 3.

In one embodiment, the invention provides a microarray for predicting the risk of developing antibodies against Factor VIII (FVIII) in an individual diagnosed with Hemophilia, the microarray comprising a support having a plurality of discrete regions, each discrete region having a nucleic acid fragment spotted thereon, wherein at least one nucleic acid fragment spotted on the support comprises a sequence that is complementary to a genomic sequence that flanks a single nucleotide polymorphism (SNP) selected from the group consisting of a SNP listed in Table 2 and a SNP listed in Table 4. In a preferred embodiment, the at least one SNP is selected from those listed in Table 4. In another preferred embodiment, the at least one SNP is selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888. In one embodiment, the oligonucleotide capable of being used to detect at least one SNP comprises a sequence complementary to a genomic sequence flanking the SNP. In a specific embodiment, the oligonucleotide sequence that is complementary to the genomic sequence that flanks a SNP includes a nucleotide corresponding to the position of the SNP in the genome. In one embodiment, the nucleotide corresponding to the position of the SNP in the genome is the rare nucleotide (i.e., the SNP). In another embodiment, the nucleotide corresponding to the position of the SNP in the genome is the wild type nucleotide.

In certain embodiments, the microarray comprises at least 2 nucleic acid fragments comprising a sequence that is complementary to a genomic sequence that flanks a single nucleotide polymorphism (SNP) listed in Tables 2 and 4, or at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, more, or all of the SNPs listed in Tables 1 to 4. In a preferred embodiment, the SNPs are selected from those listed in Table 3.

V. Specific Embodiments

In one embodiment, the present invention provides a method for predicting the risk of developing antibodies against Factor VIII (FVIII) in an individual diagnosed with Hemophilia, the method comprising the steps of: (a) detecting the presence of at least one single nucleotide polymorphism (SNP) selected from the group consisting of a SNP listed in Table 1, a SNP listed in Table 2, a SNP listed in Table 3, and a SNP listed in Table 4, in a biological sample from the individual; and (b) predicting the risk of the individual of developing antibodies to FVIII.

In one embodiment, the present invention provides a method for predicting the risk of developing antibodies against Factor VIII (FVIII) in an individual diagnosed with Hemophilia, the method comprising the steps of: (a) detecting the presence of at least one single nucleotide polymorphism (SNP) selected from the group consisting of a SNP listed in Table 1, a SNP listed in Table 2, a SNP listed in Table 3, and a SNP listed in Table 4, in a biological sample from the individual; and (b) predicting the risk of the individual of developing antibodies to FVIII, wherein the detection of a SNP associated with an odds ratio of less than 1 is predictive of a decreased risk of developing antibodies against FVIII and the detection of a SNP associated with an odds ratio of more than 1.0 is predictive of an increased risk of developing antibodies against FVIII.

In one embodiment of the methods provided above, the individual has not received therapy comprising administration of FVIII.

In one embodiment of the methods provided above, the individual has received therapy comprising administration of FVIII.

In one embodiment of the methods provided above, the individual has been diagnosed with mild Hemophilia.

In one embodiment of the methods provided above, the individual has been diagnosed with moderate Hemophilia.

In one embodiment of the methods provided above, the individual has been diagnosed with severe Hemophilia.

In one embodiment of the methods provided above, the at least one single nucleotide polymorphism (SNP) is a SNP listed in Table 2 or a SNP listed in Table 4.

In one embodiment of the methods provided above, the step of detecting the presence of at least one SNP comprises amplifying a nucleic acid present in the biological sample.

In one embodiment of the methods provided above, the step of detecting the presence of at least one SNP comprises a technique selected from the group consisting of mass spectroscopy, RT-PCR, microarray hybridization, pyrosequencing, thermal cycle sequencing, capillary array sequencing, and solid phase sequencing.

In one embodiment of the methods provided above, the step of detecting the presence of at least one SNP comprises a methods selected from the group consisting of a hybridization-based method, an enzymatic-based method, a PCR-based method, a sequencing method, a ssDNA conformational method, and a DNA melting temperature assay.

In one embodiment of the methods provided above, the step of detecting the presence of at least one SNP comprises microarray hybridization.

In one embodiment of the methods provided above, the SNP is selected from the group consisting of rs12368829, rs11744216, rs1863993, rs4147385, rs12546235, rs4242389, rs10054825, rs17535213, rs10072056, and rs17725712.

In one embodiment of the methods provided above, at least one detected SNP is rs12368829.

In one embodiment of the methods provided above, at least one detected SNP is rs11744216.

In one embodiment of the methods provided above, at least one detected SNP is rs1863993.

In one embodiment of the methods provided above, at least one detected SNP is rs4147385.

In one embodiment of the methods provided above, at least one detected SNP is rs12546235.

In one embodiment of the methods provided above, at least one detected SNP is rs4242389.

In one embodiment of the methods provided above, at least one detected SNP is rs10054825.

In one embodiment of the methods provided above, at least one detected SNP is rs17535213.

In one embodiment of the methods provided above, at least one detected SNP is rs10072056.

In one embodiment of the methods provided above, at least one detected SNP is rs17725712.

In one embodiment of the methods provided above, the SNP is selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888.

In one embodiment of the methods provided above, at least one detected SNP is rs12368829.

In one embodiment of the methods provided above, at least one detected SNP is rs4147385.

In one embodiment of the methods provided above, at least one detected SNP is rs11744216.

In one embodiment of the methods provided above, at least one detected SNP is rs1863993.

In one embodiment of the methods provided above, at least one detected SNP is rs17535213.

In one embodiment of the methods provided above, at least one detected SNP is rs10072056.

In one embodiment of the methods provided above, at least one detected SNP is rs10054825.

In one embodiment of the methods provided above, at least one detected SNP is rs12546235.

In one embodiment of the methods provided above, at least one detected SNP is rs4242389.

In one embodiment of the methods provided above, at least one detected SNP is rs2071336.

In one embodiment of the methods provided above, at least one detected SNP is rs414634.

In one embodiment of the methods provided above, at least one detected SNP is rs17725712.

In one embodiment of the methods provided above, at least one detected SNP is rs11773821.

In one embodiment of the methods provided above, at least one detected SNP is rs8005905.

In one embodiment of the methods provided above, at least one detected SNP is rs9482888.

In one embodiment of the methods provided above, the method further comprises assigning a treatment to the individual based on the predicted risk of developing antibodies against Factor VIII.

In one embodiment of the methods provided above, the treatment comprises administration of Factor VIII.

In one embodiment of the methods provided above, the treatment comprises administration of a non-Factor VIII hemostatic agent.

In one embodiment of the methods provided above, the treatment comprises administration of Factor VIII and a non-Factor VIII hemostatic agent.

In one embodiment of the methods provided above, the treatment comprising administration of Factor VIII is assigned to an individual with a predicted decreased risk of developing antibodies against Factor VIII.

In one embodiment of the methods provided above, the treatment comprising Factor VIII bypass therapy is assigned to an individual with a predicted increased risk of developing antibodies against Factor VIII.

In one embodiment of the methods provided above, assigning treatment comprises adjusting a dosage and/or frequency of Factor VIII administration based on the predicted risk of developing antibodies against Factor VIII.

In one embodiment of the methods provided above, adjusting a dosage of Factor VIII comprises increasing the dosage and/or frequency of Factor VIII administered to an individual with a predicted decreased risk of developing antibodies against Factor VIII.

In one embodiment of the methods provided above, adjusting a dosage of Factor VIII comprises decreasing the dosage and/or frequency of Factor VIII administered to an individual with a predicted increased risk of developing antibodies against Factor VIII.

In one embodiment of the methods provided above, assigning treatment comprises adjusting a dosage and/or frequency of a non-Factor VIII hemostatic agent administration based on the predicted risk of developing antibodies against Factor VIII.

In one embodiment of the methods provided above, adjusting a dosage of a non-Factor VIII hemostatic agent comprises decreasing the dosage and/or frequency of a non-Factor VIII hemostatic agent administered to an individual with a predicted decreased risk of developing antibodies against Factor VIII.

In one embodiment of the methods provided above, adjusting a dosage of a non-Factor VIII hemostatic agent comprises increasing the dosage and/or frequency of a non-Factor VIII hemostatic agent administered to an individual with a predicted increased risk of developing antibodies against Factor VIII.

In one embodiment, the present invention provides an oligonucleotide from 10 to 60 nucleotides in length that contacts at least one single nucleotide polymorphism (SNP) selected from the group consisting of the SNPs listed in Table 1.

In one embodiment, the present invention provides a diagnostic kit for predicting the risk of developing antibodies against Factor VIII (FVIII) in an individual diagnosed with Hemophilia, the kit comprising at least one oligonucleotide capable of being used to detect at least one single nucleotide polymorphism (SNP) selected from the group consisting of a SNP listed in Table 1, a SNP listed in Table 2, a SNP listed in Table 3, and a SNP listed in Table 4.

In one embodiment of the diagnostic kits described above, the SNP is selected from the group consisting of rs12368829, rs11744216, rs1863993, rs4147385, rs12546235, rs4242389, rs10054825, rs17535213, rs10072056, and rs17725712.

In one embodiment of the diagnostic kits described above, the kit comprises an oligonucleotide capable of being used to detect SNP rs12368829.

In one embodiment of the diagnostic kits described above, the kit comprises an oligonucleotide capable of being used to detect SNP rs11744216.

In one embodiment of the diagnostic kits described above, the kit comprises an oligonucleotide capable of being used to detect SNP rs1863993.

In one embodiment of the diagnostic kits described above, the kit comprises an oligonucleotide capable of being used to detect SNP rs4147385.

In one embodiment of the diagnostic kits described above, the kit comprises an oligonucleotide capable of being used to detect SNP rs12546235.

In one embodiment of the diagnostic kits described above, the kit comprises an oligonucleotide capable of being used to detect SNP rs4242389.

In one embodiment of the diagnostic kits described above, the kit comprises an oligonucleotide capable of being used to detect SNP rs10054825.

In one embodiment of the diagnostic kits described above, the kit comprises an oligonucleotide capable of being used to detect SNP rs17535213.

In one embodiment of the diagnostic kits described above, the kit comprises an oligonucleotide capable of being used to detect SNP rs10072056.

In one embodiment of the diagnostic kits described above, the kit comprises an oligonucleotide capable of being used to detect SNP rs17725712.

In one embodiment, the present invention provides a diagnostic kit for predicting the risk of developing antibodies against Factor VIII (FVIII) in an individual diagnosed with severe Hemophilia, the kit comprising at least one oligonucleotide capable of being used to detect at least one single nucleotide polymorphism (SNP) selected from the group consisting of a SNP listed in Table 2 and a SNP listed in Table 4.

In one embodiment of the diagnostic kits described above, the SNP is selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888.

In one embodiment of the diagnostic kits described above, the kit comprises an oligonucleotide capable of being used to detect SNP rs12368829.

In one embodiment of the diagnostic kits described above, the kit comprises an oligonucleotide capable of being used to detect SNP rs4147385.

In one embodiment of the diagnostic kits described above, the kit comprises an oligonucleotide capable of being used to detect SNP rs11744216.

In one embodiment of the diagnostic kits described above, the kit comprises an oligonucleotide capable of being used to detect SNP rs1863993.

In one embodiment of the diagnostic kits described above, the kit comprises an oligonucleotide capable of being used to detect SNP rs17535213.

In one embodiment of the diagnostic kits described above, the kit comprises an oligonucleotide capable of being used to detect SNP rs10072056.

In one embodiment of the diagnostic kits described above, the kit comprises an oligonucleotide capable of being used to detect SNP rs10054825.

In one embodiment of the diagnostic kits described above, the kit comprises an oligonucleotide capable of being used to detect SNP rs12546235.

In one embodiment of the diagnostic kits described above, the kit comprises an oligonucleotide capable of being used to detect SNP rs4242389.

In one embodiment of the diagnostic kits described above, the kit comprises an oligonucleotide capable of being used to detect SNP rs2071336.

In one embodiment of the diagnostic kits described above, the kit comprises an oligonucleotide capable of being used to detect SNP rs414634.

In one embodiment of the diagnostic kits described above, the kit comprises an oligonucleotide capable of being used to detect SNP rs17725712.

In one embodiment of the diagnostic kits described above, the kit comprises an oligonucleotide capable of being used to detect SNP rs11773821.

In one embodiment of the diagnostic kits described above, the kit comprises an oligonucleotide capable of being used to detect SNP rs8005905.

In one embodiment of the diagnostic kits described above, the kit comprises an oligonucleotide capable of being used to detect SNP rs9482888.

In one embodiment of the diagnostic kits described above, the oligonucleotide flanks the position of the SNP in the genome.

In one embodiment of the diagnostic kits described above, the oligonucleotide overlaps the position of the SNP in the genome.

In one embodiment, the present invention provides a microarray for predicting the risk of developing antibodies against Factor VIII (FVIII) in an individual diagnosed with Hemophilia, the microarray comprising a support having a plurality of discrete regions, each discrete region having a nucleic acid fragment spotted thereon, wherein at least one nucleic acid fragment spotted on the support comprises a sequence that is complementary to a genomic sequence that flanks a single nucleotide polymorphism (SNP) selected from the group consisting of a SNP listed in Table 1, a SNP listed in Table 2, a SNP listed in Table 3, and a SNP listed in Table 4.

In one embodiment of the microarrays described above, the SNP is selected from the group consisting of rs12368829, rs11744216, rs1863993, rs4147385, rs12546235, rs4242389, rs10054825, rs17535213, rs10072056, and rs17725712.

In one embodiment, the present invention provides a microarray for predicting the risk of developing antibodies against Factor VIII (FVIII) in an individual diagnosed with severe Hemophilia, the microarray comprising a support having a plurality of discrete regions, each discrete region having a nucleic acid fragment spotted thereon, wherein at least one nucleic acid fragment spotted on the support comprises a sequence that is complementary to a genomic sequence that flanks a single nucleotide polymorphism (SNP) selected from the group consisting of a SNP listed in Table 2 and a SNP listed in Table 4.

In one embodiment of the microarrays described above, the SNP is selected from the group consisting of rs12368829, rs4147385, rs11744216, rs1863993, rs17535213, rs10072056, rs10054825, rs12546235, rs4242389, rs2071336, rs414634, rs17725712, rs11773821, rs8005905, and rs9482888.

In one embodiment of the microarrays described above, the sequence that is complementary to a genomic sequence that flanks a single nucleotide polymorphism (SNP) includes a nucleotide corresponding to the position of the SNP in the genome.

VI. Examples

Example 1

The following example is offered to illustrate, but not to limit, the claimed invention.

Through a collaboration among three multi-center studies: the Hemophilia Inhibitor Genetics Study (HIGS), the Malmo International Brother Study (MIBS), and the Hemophilia Growth and Development Study (HGDS), a combined cohort was formed to conduct an association study to test the hypothesis that antibody development to FVIII is mediated by immune response and immune modifier genes. The HIGS study population (N=295) was composed of brother pairs concordant for a history of inhibitors, or discordant (one with an inhibitor, the other without); and a group of singletons with inhibitors. Participants from Europe and North America accounted for 43% and 57% of the HIGS population, respectively. The MIBS study population (N=120) was composed of brother pairs with hemophilia with or without inhibitors, recruited primarily from centers in Europe. The HGDS (N=265) is a population-based longitudinal investigation conducted in 14 US hemophilia treatment centers. Together, these studies make up the HIGS Combined Cohort and included clinical and laboratory data for 680 people with hemophilia A.

Using the Illumina iSelect® platform, 14,626 single nucleotide polymorphisms (SNPs) from 1,081 genes were typed. These genes included immune response and immune modifier genes, including cytokines and their receptors, chemokines and their receptors, pathway gene involved in inflammatory and immune responses, and human leukocyte antigen (HLA) gene complex genes. The SNPs were selected using an algorithm to maximize information content and minimize the number of SNPs/gene. All regulatory and nonsynonymous (codon-changing) SNPs within a gene were chosen, as well as haplotype tagging SNPs, using stringent criteria to avoid SNPs that are non-independent.

The statistical analysis was completed among the total group (N=680). Models were adjusted for population substructure, severity of hemophilia, type of factor VIII gene mutation (high vs. low risk), year of birth, and geographic region (Europe/North America). Meta-analyses were used to obtain single odds ratios (OR) and p-values for the three cohorts.

Eighty-five percent of the HIGS Combined Cohort had severe (<0.01 IU/mL) hemophilia; 10% had moderate (0.01-0.05 IU/mL) hemophilia; and 4.4% had mild (>0.05-0.4 IU/mL) hemophilia. The cohort was predominately of European descent, 81.0%, with 6.2% of African descent, 8.8% Hispanic, and the remaining 4% of other races and ethnicities. Forty-nine percent of the cohort had, or had a history of, an inhibitor ≥1 BU.

A total of 13,952 of the 14,626 (95.4%) SNPs were successfully genotyped. One hundred fourteen were associated with inhibitor status at the p<0.01 level (Table 1). Strong SNP associations for the total group were observed in the DOCK2 (rs11744216, OR 0.28, p=0.00004; and rs1863993, OR 3.9, p=0.0002), MAPK9 (rs4147385, OR 2.0, p=0.0003), F13A1 (rs13206518, OR 0.32, p=0.00007), CD36 (rs3211834, OR 0.56, p=0.0002), and PTPRR (rs1567748, OR 0.51, p=0.0003) genes (Table 1). For four markers located within the MAPK9 (rs4147385), DOCK2 (rs11744216 and rs1863993), and CD36 (rs3211834) genes, the associations were similar, or stronger, for the subgroup with severe hemophilia (Table 2). For the subgroup with severe hemophilia, a strong association with inhibitor development was found for the SNP rs4147385, a C>T variant in an intronic region of the MAPK9 gene (OR 2.3, p=0.00003); for the SNP rs11744216, a C>G variant in an intronic region of the DOCK2 gene (OR 0.30, p=0.00008); for the SNP rs1863993, a C>T variant in an intronic region of the DOCK2 gene (OR 4.4, p=0.0009); and for the SNP rs3211834, a A>C variant in an intronic region of the CD36 gene (OR 0.59, p=0.0008).

Example 2

In order to further validate the findings in Example 1, additional samples were collected and analyzed for the presence of SNPs associated with the formation of Factor VIII autoantibody inhibitors in patients with mild, moderate, and severe Hemophilia. As above, a combined cohort was formed from three multi-center studies: the Hemophilia Inhibitor Genetics Study (HIGS), the Malmö International Brother Study (MIBS), and the Hemophilia Growth and Development Study (HGDS), to conduct an association study to test the hypothesis that antibody development to FVIII is mediated by immune response and immune modifier genes. In total, samples from 774 patients diagnosed with Hemophilia, 674 of which were diagnosed with severe Hemophilia, were used for the meta-analysis.

Using the Illumina iSelect® platform, 14,626 single nucleotide polymorphisms (SNPs) from 1,081 genes were typed. These genes included immune response and immune modifier genes, including cytokines and their receptors, chemokines and their receptors, pathway gene involved in inflammatory and immune responses, and human leukocyte antigen (HLA) gene complex genes. The SNPs were selected using an algorithm to maximize information content and minimize the number of SNPs/gene. All regulatory and nonsynonymous (codon-changing) SNPs within a gene were chosen, as well as haplotype tagging SNPs, using stringent criteria to avoid SNPs that are non-independent.

Genotype data were obtained for the entire, combined cohort on the Illumina iSelect panel composed of 14,626 polymorphic markers. Testing for missingness (>20% missing), low minor allele frequency (<0.01) and a departure from Hardy Weinberg equilibrium (p<0.001), left 13,394 markers for analysis. The analysis was carried out separately for each of the three study cohorts; HGDS, MIBS and HIGS. Using the markers that passed QC, principal components were constructed to account for population admixture. Because of the different distributions of related individuals in each cohort, different models were used to analyze the data. The HGDS individuals were analyzed with logistic regression, MBS with GEE and HIGS with alternating logistic regression. Covariates included severity of hemophilia, year of birth, the first three principal components to account for admixture, and mutation risk in the case of MIBS and HIGS and an indicator of presence of factor VIII gene inversion for HGDS. The primary hypothesis test was carried out on the predictor for each SNP which was modeled as additive or specifically the number of minor alleles in each individual. Additionally the models were rerun on only the individuals with severe hemophilia. Once each estimate and standard error was obtained for each cohort model on each SNP, they were combined in a meta analytic technique summing the estimates weighted by the standard errors. A new standard error was also calculated which allowed Z statistic to be constructed and tested for the total combined cohort.

The statistical analysis was completed among the total group (N=774), as well as among patients diagnosed with severe Hemophilia (N=674). Models were adjusted for population substructure, severity of hemophilia, type of factor VIII gene mutation (high vs. low risk), year of birth, and geographic region (Europe/North America). Meta-analyses were used to obtain single odds ratios (OR) and p-values for the three cohorts.

A total of 13,394 of the 14,626 (91.6%) SNPs were successfully genotyped. Two hundred and sixteen were associated with inhibitor status at the p<0.01 level (Table 3). Strong SNP associations for the total group were observed in the CCDC41 (rs12368829, OR 0.27, p=5.08E-07); DOCK2 (rs11744216, OR 0.31, p=3.56E-06; and rs1863993, OR 3.89, p=8.36E-05); MAPK9 (rs4147385, OR 2.14, p=9.22E-06); TNFRSF1OC (rs12546235, OR 0.43, p=1.11E-05); and rs4242389, OR 0.50, p=0.000113642); IQGAP2 (rs10054825, OR 0.37, p=2.21E-05); PUS7L (rs17535213, OR 0.57, p=4.02E-05); PDGFRB (rs10072056, OR 0.61, p=5.84E-05); and CSF1R (rs17725712, OR 2.51, p=0.000165351) genes.

Strong SNP associations for the severe Hemophilia group were observed in the CCDC41 (rs12368829, OR 0.25, p=1.81E-07); MAPK9 (rs4147385, OR 2.44, p=1.08E-06); DOCK2 (rs11744216, OR 0.32, p=5.86E-06; and rs1863993, OR 4.33, p=0.000159); PUS7L (rs17535213, OR 0.54, p=1.04E-05); PDGFRB (rs10072056, OR 0.57, p=1.05E-05); IQGAP2 (rs10054825, OR 0.37, p=1.10E-05); TNFRSF10C (rs12546235, OR 0.44, p=1.64E-05; and rs4242389, OR 0.50, p=0.000128788); TNFRSF17 (rs2071336, OR 0.27, p=0.000106); BLM (rs414634, OR 1.72, p=0.000124); CSF1R (rs17725712, OR 3.00, p=0.000124); PTPRN2 (rs11773821, OR 0.51, p=0.000130); HSP90AA1 (rs8005905, OR 0.48; p=0.000132); and PTPRK (rs9482888, OR 10.75, p=0.000182) genes.

Example 3

The risk of developing antibodies against Factor VIII (FVIII) in an individual diagnosed with Hemophilia A may be determined by detecting one or more SNPs disclosed herein. To do this, a capture probe set comprising oligonucleotides capable of distinguishing the nucleotide present at the SNP position may be attached to a solid support to create an oligonucleotide array. For example, probes capable of detecting the set of SNPs listed in Table 5 are used to create a microarray. Nucleic acid (i.e., genomic DNA, cDNA, mRNA, etc.) is isolated and/or amplified from a biological sample taken from the individual and subsequently hybridized to the array using hybridization techniques well known in the art. The identity of the nucleotides present at the 24 SNP genomic positions shown in Table 5 can then be determined using detection/analysis techniques also well known in the art. Alternatively, the presence or absence of the SNP of interest can be determined using the same well known techniques.

The results of the SNP detection described above, can then be used to predict a risk for the development of Factor VIII inhibitor antibodies in the individual. For example, the detection of rs12368829 in the sample is predictive of a significantly decreased risk of developing Factor VIII inhibitors. Similarly, the detection of both rs4147385 and rs927335 is predictive of a significantly increased risk of developing Factor VIII inhibitors.

Likewise, detection of one or more SNPs listed in Table 5 may be achieved by performing one or more RT-qPCR reactions. In this case, individual RT-qPCR reactions or multiplex RT-qPCR reactions may be performed to identify the nucleotides present at the genomic locations of the SNPs listed in Table 5, or to detect the presence or absence of the SNPs listed in Table 5, using techniques well known in the art. The data provided by these assays may then be used to provide a risk for the development of Factor VIII inhibitor antibodies in the individual.

Any probe set may be used, comprising capture probes capable of detecting between 1 and all of the SNPs listed in Tables 1 to 4. The probe sets may further comprise internal controls, additional probes useful for providing further predictive power, and/or unrelated probe sets.

TABLE 5

| SNP | Gene | Meta Odds | Meta P |
|---|---|---|---|
| rs12368829 | CCDC41 | 0.27311013 | 5.08E-07 |
| rs11744216 | DOCK2 | 0.30667899 | 3.56E-06 |

TABLE 5-continued

| SNP | Gene | Meta Odds | Meta P |
|---|---|---|---|
| rs4147385 | MAPK9 | 2.13745578 | 9.22E-06 |
| rs12546235 | TNFRSF10C | 0.43388002 | 1.11E-05 |
| rs10054825 | IQGAP2 | 0.3743547 | 2.21E-05 |
| rs17535213 | PUS7L | 0.57027044 | 4.02E-05 |
| rs10072056 | PDGFRB | 0.60837768 | 5.84E-05 |
| rs1863993 | DOCK2 | 3.88981038 | 8.36E-05 |
| rs4242389 | TNFRSF10C | 0.49632251 | 0.00011364 |
| rs17725712 | CSF1R | 2.50759989 | 0.00016535 |
| rs11773821 | PTPRN2 | 0.54041127 | 0.00033105 |
| rs414634 | BLM | 1.62246205 | 0.00033946 |
| rs1882019 | HSP90B1 | 0.53629298 | 0.00034044 |
| rs13206518 | F13A1 | 0.39427174 | 0.00035099 |
| rs927335 | CD44 | 1.69891458 | 0.00036195 |
| rs6482644 | PTPRE | 0.57798945 | 0.00040403 |
| rs4077341 | TNFRSF10C | 0.63448794 | 0.00042665 |
| rs1884564 | LOC728018 | 0.55434198 | 0.00051894 |
| rs3826392 | MAP2K4 | 0.6309839 | 0.00053597 |
| rs390406 | CLC | 0.56597223 | 0.00053686 |
| rs440238 | PTPRD | 0.62008121 | 0.00057369 |
| rs9482888 | PTPRK | 6.50375409 | 0.00058077 |
| rs2596606 | NFATC1 | 1.75806233 | 0.00058124 |
| rs17652304 | IQGAP2 | 3.55426184 | 0.00062941 |

Example 4

The results obtained in the previous example may then be used to direct or modify a course of therapy in the individual. For example, the detection of SNP rs12368829, which is predictive of a decreased likelihood of the development of Factor VIII inhibitor in response to Factor VIII therapy, may lead a physician to assign a course of treatment comprising administration of FVIII to the individual. Conversely, the detection of SNPs rs4147385 and rs927335, which is predictive of an increased risk of developing Factor VIII inhibitor antibodies in response to Factor VIII therapy, may lead a physician to assign a course of treatment comprising administration of a non-FVIII hemostatic agent (i.e., FVIII bypass therapy). Alternatively, after the detection of both rs4147385 and rs927335, a physician may assign a course of treatment comprising administration of both Factor VIII and a non-FVIII hemostatic agent. In this manner, combination therapy may more effective than administration of either Factor VIII or a non-FVIII hemostatic agent alone. For example, the development of anti-FVIII inhibitory antibodies results in the reduced efficacy of FVIII administration, at which point the non-FVIII hemostatic agent may supplement this deficiency.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

TABLE 1

| SNP | Chrom | BP | Region | Gene | HGDS Odds | HGDS P |
|---|---|---|---|---|---|---|
| rs11744216 | 5 | 169018841 | intron | DOCK2 | 0.4264463 | 0.170966 |
| rs13206518 | 6 | 6098001 | intron | F13A1 | 0.759322 | 0.616534 |
| rs2227827 | 5 | 76054800 | intron | F2R | 1.2382572 | 0.711259 |
| rs3211834 | 7 | 80118053 | intron | CD36 | 0.6593762 | 0.138659 |
| rs1863993 | 5 | 169142758 | intron | DOCK2 | 5.0476821 | 0.011274 |
| rs910682 | 6 | 112282428 | intron | FYN | 2.1062593 | 0.012895 |
| rs4147385 | 5 | 179610123 | intron | MAPK9 | 2.9087957 | 0.000155 |
| rs1567748 | 12 | 69360997 | intron | PTPRR | 1.0194855 | 0.95761 |
| rs3211821 | 7 | 80116499 | intron | CD36 | 0.6553039 | 0.126315 |
| rs6482644 | 10 | 129715311 | intron | PTPRE | 0.6295681 | 0.08468 |
| rs414634 | 15 | 89157257 | intron | BLM | 1.9152708 | 0.012981 |
| rs10072056 | 5 | 149485499 | intron | PDGFRB | 1.0238421 | 0.931546 |
| rs17652304 | 5 | 75912949 | intron | IQGAP2 | 4.5248878 | 0.005062 |
| rs2584019 | 12 | 69318052 | locus-region | PTPRR | 1.1113653 | 0.767548 |
| rs2879097 | 17 | 34143085 | locus-region | PCGF2 | 0.3989738 | 0.01103 |
| rs17725712 | 5 | 149471001 | intron | CSF1R | 2.2707005 | 0.092905 |
| rs12667537 | 7 | 157343101 | intron | PTPRN2 | 0.5285206 | 0.026763 |
| rs2302821 | 9 | 131541702 | mrna-utr | PTGES | 0.413199 | 0.079245 |
| rs4104 | 7 | 157639794 | intron | PTPRN2 | 0.7155353 | 0.197892 |
| rs6837303 | 4 | 111189034 | locus-region | ELOVL6 | 0.5807509 | 0.058419 |
| rs3736395 | 5 | 75924224 | intron | IQGAP2 | 2.0624196 | 0.014235 |
| rs12546235 | 8 | 23018464 | intron | TNFRSF10C | 0.7274756 | 0.422086 |
| rs4698806 | 4 | 111190938 | mrna-utr | ELOVL6 | 0.5664635 | 0.050564 |
| rs11952962 | 5 | 75931035 | intron | IQGAP2 | 2.0142888 | 0.017929 |
| rs3797390 | 5 | 75942821 | intron | IQGAP2 | 2.3878022 | 0.002205 |
| rs13042473 | 20 | 40843315 | intron | PTPRT | 0.5586063 | 0.107265 |
| rs13096099 | 3 | 61819146 | intron | PTPRG | 0.4982842 | 0.234687 |
| rs7290696 | 22 | 30671684 | intron | YWHAH | 1.2490102 | 0.459588 |
| rs949664 | 12 | 69368222 | intron | PTPRR | 1.0767496 | 0.809522 |
| rs4462251 | 10 | 129749982 | intron | PTPRE | 0.7208544 | 0.185484 |
| rs4752894 | 11 | 48077512 | intron | PTPRJ | 0.5295218 | 0.020616 |
| rs10261447 | 7 | 157643166 | intron | PTPRN2 | 0.7552154 | 0.278122 |
| rs7246376 | 19 | 8109328 | coding-non-synonymous | FBN3 | 1.4043985 | 0.260212 |
| rs4752896 | 11 | 48086525 | intron | PTPRJ | 3.8641862 | 0.003824 |
| rs390406 | 19 | 44920811 | locus-region | CLC | 0.6675452 | 0.239964 |
| rs2596606 | 18 | 75263804 | intron | NFATC1 | 1.8412808 | 0.05504 |
| rs440238 | 9 | 9006071 | intron | PTPRD | 0.3654781 | 0.001385 |
| rs1892803 | 3 | 37572487 | intron | ITGA9 | 1.9891348 | 0.067518 |

TABLE 1-continued

| | | | | | | |
|---|---|---|---|---|---|---|
| rs4077341 | 8 | 23018293 | intron | TNFRSF10C | 0.6342569 | 0.090988 |
| rs9826296 | 3 | 39279822 | locus-region | CX3CR1 | 0.3438183 | 0.018361 |
| rs7348444 | 20 | 40263638 | intron | PTPRT | 0.6379987 | 0.214628 |
| rs4752904 | 11 | 48122843 | coding-non-synonymous | PTPRJ | 0.5229615 | 0.015662 |
| rs2305340 | 12 | 7157242 | — | — | 0.425719 | 0.037702 |
| rs805274 | 6 | 31773173 | intron | BAT5 | 0.5365861 | 0.046424 |
| rs1411479 | 1 | 179273553 | intron | MR1 | 1.4273583 | 0.16464 |
| rs2076620 | 1 | 29488905 | intron | PTPRU | 1.5037749 | 0.156645 |
| rs4724231 | 7 | 43608739 | intron | STK17A | 0.7894051 | 0.512999 |
| rs7715375 | 5 | 146106438 | intron | PPP2R2B | 1.1146267 | 0.739882 |
| rs7289754 | 22 | 20926259 | — | — | 2.2927241 | 0.00152 |
| rs12310405 | 12 | 69330069 | intron | PTPRR | 1.0252831 | 0.929397 |
| rs3845422 | 1 | 179279594 | intron | MR1 | 0.5959129 | 0.098555 |
| rs17671456 | 8 | 22441022 | intron | PPP3CC | 1.5913304 | 0.206536 |
| rs1885831 | 20 | 40836321 | intron | PTPRT | 0.6323805 | 0.213699 |
| rs4472605 | 9 | 34556190 | intron | CNTFR | 2.3112244 | 0.015115 |
| rs5743740 | 23 | 12801881 | intron | TLR7 | 1.7103053 | 0.03429 |
| rs2070123 | 1 | 78888493 | coding-non-synonymous | IFI44 | 0.8374258 | 0.666134 |
| rs2179694 | 6 | 128405416 | intron | PTPRK | 2.6815501 | 0.004271 |
| rs6782288 | 3 | 61805637 | intron | PTPRG | 0.2706226 | 0.084428 |
| rs1877563 | 3 | 39279468 | locus-region | CX3CR1 | 0.4255593 | 0.062242 |
| rs1781795 | 6 | 6186280 | intron | F13A1 | 1.846775 | 0.054544 |
| rs9862163 | 3 | 37557606 | intron | ITGA9 | 1.8809113 | 0.073469 |
| rs1882019 | 12 | 102861797 | intron | HSP90B1 | 0.5921978 | 0.25287 |
| rs704853 | 1 | 165735488 | intron | CD247 | 2.4731734 | 0.006262 |
| rs2278324 | 5 | 38917360 | intron | OSMR | 2.4191263 | 0.008917 |
| rs10854166 | 19 | 18513844 | intron | FKBP8 | 1.0554308 | 0.82636 |
| rs7692976 | 4 | 111131016 | intron | EGF | 0.8410174 | 0.490258 |
| rs1046780 | 11 | 77604417 | mrna-utr | GAB2 | 0.634111 | 0.164847 |
| rs7124275 | 11 | 48118881 | intron | PTPRJ | 0.7740908 | 0.310137 |
| rs1007212 | 15 | 97101441 | intron | IGF1R | 1.6260816 | 0.052845 |
| rs4498385 | 6 | 128491712 | intron | PTPRK | 2.134554 | 0.03148 |
| rs3788151 | 21 | 45161993 | intron | ITGB2 | 0.6014832 | 0.293327 |
| rs11740298 | 5 | 149472648 | locus-region | PDGFRB | 1.1785056 | 0.58352 |
| rs3815003 | 15 | 89113827 | intron | BLM | 0.7320953 | 0.32305 |
| rs6482647 | 10 | 129716363 | intron | PTPRE | 0.8763896 | 0.590518 |
| rs2296449 | 1 | 117380273 | intron | IGSF2 | 0.2786922 | 0.231422 |
| rs5746154 | 3 | 12680048 | intron | RAF1 | 0.7424757 | 0.425298 |
| rs2020902 | 1 | 15706947 | intron | CASP9 | 1.5643264 | 0.205653 |
| rs927010 | 6 | 112254016 | intron | FYN | 0.9174485 | 0.759767 |
| rs5743220 | 11 | 43299463 | intron | API5 | 0.8074122 | 0.59914 |
| rs499205 | 11 | 125639829 | intron | SRPR | 0.3215836 | 0.001716 |
| rs2302267 | 23 | 12795499 | intron | TLR7 | 1.9061049 | 0.014414 |
| rs6214 | 12 | 101317699 | mrna-utr | IGF1 | 1.5377377 | 0.088519 |
| rs1105238 | 1 | 159948285 | intron | FCRLA | 1.5723055 | 0.087345 |
| rs12881815 | 14 | 63674348 | coding-non-synonymous | SYNE2 | 4.7576862 | 0.005158 |
| rs10054825 | 5 | 75837339 | intron | IQGAP2 | 0.4214185 | 0.06373 |
| rs10836342 | 11 | 35198213 | intron | CD44 | 1.4258451 | 0.198951 |
| rs3819496 | 8 | 143920893 | intron | GML | 0.7566059 | 0.292013 |
| rs12831813 | 12 | 69338568 | intron | PTPRR | 1.2079285 | 0.529818 |
| rs2157605 | 6 | 30562055 | — | — | 0.6308068 | 0.158206 |
| rs9487735 | 6 | 112272269 | intron | FYN | 1.7518657 | 0.172178 |
| rs9817149 | 3 | 191740949 | intron | IL1RAP | 2.3935609 | 0.044972 |
| rs731305 | 7 | 157375601 | intron | PTPRN2 | 1.3532686 | 0.218857 |
| rs304839 | 3 | 30706286 | intron | TGFBR2 | 1.7559848 | 0.05877 |
| rs10406354 | 19 | 59022044 | — | — | 0.8293457 | 0.602779 |
| rs17763453 | 17 | 3664884 | intron | C17orf85 | 1.9012346 | 0.019355 |
| rs2569190 | 5 | 139993100 | intron | CD14 | 1.5335318 | 0.093723 |
| rs6476985 | 9 | 5507559 | intron | PDCD1LG2 | 1.7555137 | 0.101125 |
| rs31519 | 5 | 135314336 | intron | LECT2 | 1.793477 | 0.019369 |
| rs1267843 | 6 | 6191983 | intron | F13A1 | 0.7214938 | 0.204877 |
| rs766502 | 12 | 9799696 | intron | CD69 | 0.4224928 | 0.03055 |
| rs8064821 | 17 | 73868986 | — | — | 1.6573297 | 0.157191 |
| rs4646077 | 1 | 15699723 | intron | CASP9 | 1.4654677 | 0.204825 |
| rs7851161 | 9 | 35234061 | intron | UNC13B | 1.3813911 | 0.201171 |
| rs1983165 | 3 | 62059196 | intron | PTPRG | 0.8117157 | 0.496419 |
| rs10074391 | 5 | 149486896 | intron | PDGFRB | 1.3843383 | 0.4834 |
| rs7170919 | 15 | 89115963 | intron | BLM | 0.7391559 | 0.316431 |
| rs4251520 | 12 | 42461605 | intron | IRAK4 | 1.1681216 | 0.665273 |
| rs1465073 | 12 | 51979670 | locus-region | PFDN5 | 0.6281323 | 0.0735 |
| rs613613 | 9 | 9004274 | intron | PTPRD | 0.2400912 | 0.000257 |
| rs2298877 | 14 | 101617977 | intron | HSP90AA1 | 0.7034122 | 0.323878 |
| rs17815972 | 3 | 10223974 | intron | IRAK2 | 0.6933789 | 0.131179 |
| rs12810163 | 12 | 9872429 | intron | KLRF1 | 1.5092501 | 0.105882 |

TABLE 1-continued

| | | | | | | |
|---|---|---|---|---|---|---|
| rs2267908 | 20 | 1857920 | intron | SIRPA | 1.6835746 | 0.046786 |
| rs7099752 | 10 | 129641321 | intron | PTPRE | 0.8058936 | 0.539731 |

| SNP | HIGS Odds | HIGS P | MIBS Odds | MIBS P | Meta Odds | Meta P |
|---|---|---|---|---|---|---|
| rs11744216 | 0.22571238 | 0.000282 | 0.3741365 | 0.301173 | 0.2792436 | 4.09E−05 |
| rs13206518 | 0.38117928 | 0.028779 | 0.1181848 | 3.97E−05 | 0.32286804 | 6.93E−05 |
| rs2227827 | 2.82664983 | 0.325222 | 5.7021018 | 3.60E−05 | 3.29946791 | 0.000226 |
| rs3211834 | 0.5107696 | 0.003251 | 0.5661763 | 0.114955 | 0.5633609 | 0.000238 |
| rs1863993 | 1.86996236 | 0.560579 | 3.9882943 | 0.006879 | 3.94139298 | 0.000247 |
| rs910682 | 2.14747116 | 0.01239 | 1.5283489 | 0.310709 | 1.98915377 | 0.000261 |
| rs4147385 | 2.38891621 | 0.009361 | 0.6891928 | 0.34438 | 1.96583851 | 0.000311 |
| rs1567748 | 0.45565476 | 0.00219 | 0.2252939 | 0.002164 | 0.50890627 | 0.000327 |
| rs3211821 | 0.52249896 | 0.004779 | 0.6143155 | 0.168962 | 0.57915491 | 0.000447 |
| rs6482644 | 0.80414784 | 0.331749 | 0.2230707 | 2.88E−05 | 0.58402944 | 0.000508 |
| rs414634 | 2.12705658 | 0.003435 | 0.9393436 | 0.851875 | 1.70382924 | 0.000785 |
| rs10072056 | 0.54459905 | 0.006629 | 0.4262574 | 0.006412 | 0.62104044 | 0.001428 |
| rs17652304 | 1.58179017 | 0.532079 | 3.7192948 | 0.073342 | 3.26828251 | 0.001504 |
| rs2584019 | 0.52472723 | 0.010479 | 0.1747444 | 0.000521 | 0.55367097 | 0.001599 |
| rs2879097 | 0.5883462 | 0.018123 | 0.8975647 | 0.765856 | 0.59218611 | 0.001635 |
| rs17725712 | 1.89133513 | 0.146051 | 2.3052404 | 0.024417 | 2.15670137 | 0.001637 |
| rs12667537 | 0.68616125 | 0.098587 | 0.5572059 | 0.10502 | 0.60851609 | 0.001786 |
| rs2302821 | 0.50602243 | 0.027969 | 0.4440663 | 0.202565 | 0.47427361 | 0.001918 |
| rs4104 | 0.61191833 | 0.023089 | 0.5689053 | 0.099584 | 0.63498198 | 0.002123 |
| rs6837303 | 0.66023623 | 0.071935 | 0.5408342 | 0.102554 | 0.61144675 | 0.002241 |
| rs3736395 | 1.54151151 | 0.165489 | 1.6901581 | 0.177493 | 1.76976249 | 0.002276 |
| rs12546235 | 0.4320172 | 0.004881 | 0.2265523 | 0.175241 | 0.4990938 | 0.00229 |
| rs4698806 | 0.6800816 | 0.092123 | 0.4841033 | 0.076412 | 0.6080967 | 0.002331 |
| rs11952962 | 1.53252391 | 0.160159 | 1.72391 | 0.150491 | 1.75194031 | 0.002334 |
| rs3797390 | 1.17341603 | 0.499644 | 1.680531 | 0.076666 | 1.59756682 | 0.002391 |
| rs13042473 | 0.61933994 | 0.084364 | 0.5181073 | 0.054693 | 0.57273836 | 0.00244 |
| rs13096099 | 0.29631921 | 0.006238 | 0.4908602 | 0.565263 | 0.36386724 | 0.002461 |
| rs7290696 | 2.31479609 | 0.008075 | 1.7904536 | 0.075126 | 1.71913266 | 0.002555 |
| rs949664 | 0.47128413 | 0.003215 | 0.4132124 | 0.023529 | 0.59591265 | 0.002641 |
| rs4462251 | 0.55152593 | 0.006524 | 0.8004433 | 0.44484 | 0.65622124 | 0.002769 |
| rs4752894 | 0.71389667 | 0.138587 | 0.5921131 | 0.159352 | 0.62569985 | 0.002927 |
| rs10261447 | 0.60957915 | 0.021807 | 0.5689053 | 0.099584 | 0.6451481 | 0.002956 |
| rs7246376 | 2.02440479 | 0.024548 | 2.4037715 | 0.063497 | 1.78756484 | 0.002991 |
| rs4752896 | 1.66803937 | 0.267218 | 1.7183641 | 0.283547 | 2.24773698 | 0.003155 |
| rs390406 | 0.36355189 | 0.000972 | 1.1098003 | 0.818363 | 0.55485629 | 0.003241 |
| rs2596606 | 2.16608728 | 0.022255 | 1.3148158 | 0.395289 | 1.73195975 | 0.003253 |
| rs440238 | 0.78060758 | 0.249509 | 0.6858094 | 0.289683 | 0.62828413 | 0.003296 |
| rs1892803 | 1.61477947 | 0.197508 | 2.047579 | 0.051301 | 1.87206666 | 0.003382 |
| rs4077341 | 0.68927979 | 0.081574 | 0.5588144 | 0.09436 | 0.64621499 | 0.003529 |
| rs9826296 | 0.66017337 | 0.151245 | 0.3971541 | 0.113562 | 0.52284161 | 0.003691 |
| rs7348444 | 0.52939193 | 0.023356 | 0.4970193 | 0.190505 | 0.55604255 | 0.003698 |
| rs4752904 | 0.76091128 | 0.226668 | 0.5529907 | 0.124866 | 0.6347428 | 0.003793 |
| rs2305340 | 0.63129779 | 0.078361 | 0.611059 | 0.231062 | 0.57482385 | 0.004047 |
| rs805274 | 0.65212624 | 0.086562 | 0.6270542 | 0.250577 | 0.60927983 | 0.004506 |
| rs1411479 | 1.78509969 | 0.018214 | 1.3503939 | 0.371962 | 1.54973639 | 0.004739 |
| rs2076620 | 2.4197051 | 0.017011 | 1.5093295 | 0.2763 | 1.72576938 | 0.004784 |
| rs4724231 | 0.33763134 | 0.000434 | 1.5707582 | 0.455405 | 0.54856423 | 0.004812 |
| rs7715375 | 0.33725774 | 0.000385 | 0.5863538 | 0.260186 | 0.57386348 | 0.004888 |
| rs7289754 | 0.97944148 | 0.925697 | 1.914168 | 0.028269 | 1.51042662 | 0.005001 |
| rs12310405 | 0.48112775 | 0.002654 | 0.5978915 | 0.122106 | 0.64180759 | 0.005105 |
| rs3845422 | 0.57030552 | 0.019916 | 0.8460937 | 0.658978 | 0.62448923 | 0.005195 |
| rs17671456 | 1.74929637 | 0.135263 | 2.3760572 | 0.03417 | 1.84786063 | 0.005214 |
| rs1885831 | 0.63343863 | 0.092772 | 0.5213094 | 0.059969 | 0.59943237 | 0.005315 |
| rs4472605 | 1.4480849 | 0.1795 | 1.6525984 | 0.290559 | 1.71977212 | 0.005454 |
| rs5743740 | 1.78487827 | 0.293217 | 1.5375034 | 0.141189 | 1.64973302 | 0.005618 |
| rs2070123 | 0.43008835 | 0.003914 | 0.6554991 | 0.55009 | 0.54320594 | 0.005738 |
| rs2179694 | 0.92879429 | 0.790802 | 3.368561 | 0.003379 | 1.69672289 | 0.00581 |
| rs6782288 | 0.39759991 | 0.037481 | 0.4908602 | 0.565263 | 0.37100891 | 0.005937 |
| rs1877563 | 0.55684704 | 0.050965 | 0.6579718 | 0.46717 | 0.53488592 | 0.00596 |
| rs1781795 | 1.30128893 | 0.435285 | 3.7963966 | 0.013791 | 1.79286631 | 0.006042 |
| rs9862163 | 1.34817589 | 0.353439 | 2.1946518 | 0.033418 | 1.72813239 | 0.006094 |
| rs1882019 | 0.63615624 | 0.125724 | 0.4658273 | 0.039454 | 0.57016001 | 0.006136 |
| rs704853 | 1.33683346 | 0.478197 | 1.7018946 | 0.331614 | 1.89108031 | 0.006153 |
| rs2278324 | 2.09461214 | 0.033909 | 0.6946357 | 0.467913 | 1.8096482 | 0.006165 |
| rs10854166 | 1.6604675 | 0.021344 | 1.7877334 | 0.033866 | 1.46340143 | 0.00628 |
| rs7692976 | 0.6199714 | 0.036045 | 0.4853325 | 0.041857 | 0.66237867 | 0.006377 |
| rs1046780 | 0.66019694 | 0.070308 | 0.4180109 | 0.096451 | 0.62021487 | 0.006407 |
| rs7124275 | 0.65968842 | 0.065168 | 0.4946616 | 0.047331 | 0.66309631 | 0.006437 |
| rs1007212 | 1.23849185 | 0.328324 | 2.5238917 | 0.022182 | 1.51376079 | 0.006451 |
| rs4498385 | 0.9359476 | 0.842582 | 2.6856314 | 0.0044 | 1.7145818 | 0.006549 |
| rs3788151 | 0.45971894 | 0.032168 | 0.4692903 | 0.191761 | 0.49784173 | 0.006566 |
| rs11740298 | 0.51108839 | 0.004835 | 0.4781692 | 0.036943 | 0.64372536 | 0.006595 |
| rs3815003 | 0.55397606 | 0.015021 | 0.7295119 | 0.357161 | 0.63788244 | 0.006611 |
| rs6482647 | 0.72923281 | 0.146873 | 0.366263 | 0.00172 | 0.67581779 | 0.006639 |
| rs2296449 | 0.4881357 | 0.126849 | 0.2422667 | 0.037285 | 0.37611586 | 0.006711 |

TABLE 1-continued

| | | | | | | |
|---|---|---|---|---|---|---|
| rs5746154 | 0.49711568 | 0.019558 | 0.5347065 | 0.193474 | 0.57034852 | 0.00682 |
| rs2020902 | 1.16603425 | 0.61948 | 3.7147925 | 0.001012 | 1.71795081 | 0.007013 |
| rs927010 | 0.52107784 | 0.006163 | 0.6631102 | 0.213678 | 0.65567615 | 0.007139 |
| rs5743220 | 2.67055752 | 0.043275 | 2.5838069 | 0.003556 | 1.82790198 | 0.007171 |
| rs499205 | 0.86725251 | 0.574219 | 0.6589784 | 0.142653 | 0.63787515 | 0.007211 |
| rs2302267 | 1.12015933 | 0.773011 | 1.6738235 | 0.125114 | 1.63232737 | 0.007507 |
| rs6214 | 1.66998021 | 0.038224 | 1.2172621 | 0.587461 | 1.52347214 | 0.007528 |
| rs1105238 | 1.34681946 | 0.232658 | 2.3356971 | 0.044995 | 1.55829502 | 0.007586 |
| rs12881815 | 4.97171931 | 0.127892 | 0.1594134 | 0.227197 | 3.48147191 | 0.007641 |
| rs10054825 | 0.60641377 | 0.119365 | 0.4329791 | 0.193943 | 0.52374625 | 0.00772 |
| rs10836342 | 1.40690529 | 0.14235 | 2.3160284 | 0.033397 | 1.53591151 | 0.007793 |
| rs3819496 | 0.57036831 | 0.014751 | 0.7897393 | 0.37771 | 0.68159392 | 0.007819 |
| rs12831813 | 0.51499115 | 0.004238 | 0.377223 | 0.030721 | 0.64167123 | 0.00783 |
| rs2157605 | 0.57644926 | 0.050925 | 0.6112004 | 0.284326 | 0.60077721 | 0.007938 |
| rs9487735 | 3.44089991 | 0.044818 | 1.8293887 | 0.163324 | 2.03268322 | 0.007957 |
| rs9817149 | 2.51750425 | 0.226386 | 2.8928281 | 0.211151 | 2.49550151 | 0.007992 |
| rs731305 | 2.12394507 | 0.001996 | 0.8473802 | 0.633993 | 1.49787227 | 0.00801 |
| rs304839 | 1.19553817 | 0.53873 | 2.0670691 | 0.028862 | 1.59400528 | 0.008054 |
| rs10406354 | 0.43685707 | 0.002456 | 0.9280367 | 0.866827 | 0.60235771 | 0.008131 |
| rs17763453 | 1.89566945 | 0.043789 | 0.9999378 | 0.99985 | 1.586918 | 0.008228 |
| rs2569190 | 1.85676739 | 0.008373 | 0.9048112 | 0.753265 | 1.48229265 | 0.008591 |
| rs6476985 | 1.99572072 | 0.052198 | 1.4211996 | 0.440595 | 1.75826409 | 0.008892 |
| rs31519 | 1.34118139 | 0.168684 | 1.2511892 | 0.47218 | 1.45400608 | 0.008925 |
| rs1267843 | 0.75851277 | 0.191668 | 0.4847643 | 0.027298 | 0.68344853 | 0.008954 |
| rs766502 | 0.71581985 | 0.215636 | 0.5896612 | 0.18019 | 0.60332621 | 0.009015 |
| rs8064821 | 1.5272999 | 0.22594 | 1.8307243 | 0.062525 | 1.67441451 | 0.009026 |
| rs4646077 | 1.31585407 | 0.293626 | 2.4601659 | 0.013612 | 1.56944648 | 0.009194 |
| rs7851161 | 1.63160741 | 0.028346 | 1.3056665 | 0.481747 | 1.48323184 | 0.009247 |
| rs1983165 | 0.59752742 | 0.04053 | 0.5354805 | 0.091546 | 0.64175505 | 0.009281 |
| rs10074391 | 1.81929094 | 0.157439 | 2.4042461 | 0.024418 | 1.88111528 | 0.009311 |
| rs7170919 | 0.58755828 | 0.030705 | 0.6621434 | 0.272516 | 0.64631894 | 0.009471 |
| rs4251520 | 0.43807445 | 0.002496 | 0.5157325 | 0.204856 | 0.60090009 | 0.009474 |
| rs1465073 | 0.78960669 | 0.285671 | 0.562159 | 0.070661 | 0.68081974 | 0.009555 |
| rs613613 | 0.9578572 | 0.851436 | 0.4848659 | 0.074112 | 0.63129647 | 0.009574 |
| rs2298877 | 0.56492416 | 0.027495 | 0.7020929 | 0.315076 | 0.63080907 | 0.00968 |
| rs17815972 | 0.646525 | 0.059999 | 0.721396 | 0.362499 | 0.67719779 | 0.009696 |
| rs12810163 | 2.28681538 | 0.00231 | 0.9033077 | 0.705934 | 1.4770605 | 0.009733 |
| rs2267908 | 1.27903706 | 0.312618 | 1.5601867 | 0.127776 | 1.48002659 | 0.009809 |
| rs7099752 | 0.67763312 | 0.152196 | 0.4246379 | 0.014247 | 0.6251713 | 0.009934 |

TABLE 2

| SNP | Chrom | BP | Region | Gene | HGDS Odds | HGDS P | HIGS Odds |
|---|---|---|---|---|---|---|---|
| rs4147385 | 5 | 179610123 | intron | MAPK9 | 3.06812 | 0.00017 | 2.38891621 |
| rs11744216 | 5 | 169018841 | intron | DOCK2 | 0.4561879 | 0.208945 | 0.22571238 |
| rs3211834 | 7 | 80118053 | intron | CD36 | 0.6527446 | 0.148737 | 0.5107696 |
| rs1863993 | 5 | 169142758 | intron | DOCK2 | 5.8579407 | 0.007855 | 1.86996236 |

| SNP | HIGS P | MIBS Odds | MIBS P | Meta Odds | Meta P |
|---|---|---|---|---|---|
| rs4147385 | 0.009361 | 0.9774443 | 0.964997 | 2.34125982 | 2.64E-05 |
| rs11744216 | 0.000282 | 0.5203063 | 0.446126 | 0.29801285 | 8.24E-05 |
| rs3211834 | 0.003251 | 0.7359888 | 0.413646 | 0.58620393 | 0.000818 |
| rs1863993 | 0.560579 | 4.7130981 | 0.033933 | 4.42496425 | 0.000876 |

TABLE 3

| SNP | Chrom | BP | Region | Gene | HGDS Odds | HGDS P | HIGS Odds |
|---|---|---|---|---|---|---|---|
| rs12368829 | 12 | 93326073 | intron | CCDC41 | 0.37742656 | 0.3719435 | 0.23749353 |
| rs11744216 | 5 | 169018841 | intron | DOCK2 | 0.42381549 | 0.16683371 | 0.27989213 |
| rs4147385 | 5 | 179610123 | intron | MAPK9 | 2.90585493 | 0.00015755 | 2.46419229 |
| rs12546235 | 8 | 23018464 | intron | TNFRSF10C | 0.74208 | 0.4523308 | 0.37576137 |
| rs10054825 | 5 | 75837339 | intron | IQGAP2 | 0.42794347 | 0.06709021 | 0.324665 |
| rs17535213 | 12 | 42414658 | intron | PUS7L | 1.24887348 | 0.53836493 | 0.49318189 |
| rs10072056 | 5 | 149485499 | intron | PDGFRB | 1.02326444 | 0.93339826 | 0.58186139 |
| rs1863993 | 5 | 169142758 | intron | DOCK2 | 5.4206873 | 0.00889405 | 1.79012818 |
| rs4242389 | 8 | 23028266 | intron | TNFRSF10C | 1.15216553 | 0.72881368 | 0.39817123 |
| rs17725712 | 5 | 149471001 | intron | CSF1R | 2.22229411 | 0.10166478 | 2.97352599 |
| rs11773821 | 7 | 157648848 | intron | PTPRN2 | 0.73075367 | 0.30225159 | 0.45675984 |
| rs414634 | 15 | 89157257 | intron | BLM | 1.9210693 | 0.01250141 | 1.76721841 |
| rs1882019 | 12 | 102861797 | intron | HSP90B1 | 0.6021514 | 0.26821719 | 0.54596795 |
| rs13206518 | 6 | 6098001 | intron | F13A1 | 0.7602344 | 0.61761633 | 0.47126387 |
| rs927335 | 11 | 35207094 | intron | CD44 | 1.49735827 | 0.13592394 | 1.62199792 |

TABLE 3-continued

| rs ID | chr | position | type | gene | val1 | val2 | val3 |
|---|---|---|---|---|---|---|---|
| rs6482644 | 10 | 129715311 | intron | PTPRE | 0.63879315 | 0.09490834 | 0.76981675 |
| rs4077341 | 8 | 23018293 | intron | TNFRSF10C | 0.65107201 | 0.11146361 | 0.63450801 |
| rs1884564 | 20 | 1820658 | intron | LOC728018 | 0.8398416 | 0.63023802 | 0.45784275 |
| rs3826392 | 17 | 11863629 | locus-region | MAP2K4 | 0.50984063 | 0.0470141 | 0.64374497 |
| rs390406 | 19 | 44920811 | locus-region | CLC | 0.67199333 | 0.24554649 | 0.44814554 |
| rs440238 | 9 | 9006071 | intron | PTPRD | 0.3742515 | 0.00171654 | 0.70059683 |
| rs9482888 | 6 | 128855804 | intron | PTPRK | 6.37861557 | 0.00413766 | 0.26952546 |
| rs2596606 | 18 | 75263804 | intron | NFATC1 | 1.8666183 | 0.0500392 | 2.02654187 |
| rs17652304 | 5 | 75912949 | intron | IQGAP2 | 4.57533583 | 0.00457208 | 1.64105085 |
| rs3815003 | 15 | 89113827 | intron | BLM | 0.70729829 | 0.27605212 | 0.58889226 |
| rs2278324 | 5 | 38917360 | intron | OSMR | 2.37666019 | 0.01048799 | 1.89816183 |
| rs805274 | 6 | 31773173 | intron | BAT5 | 0.54648165 | 0.05304876 | 0.62947384 |
| rs8005905 | 14 | 101638120 | coding-nonsynonymous | HSP90AA1 | 0.29750544 | 0.03237554 | 0.45357526 |
| rs2879097 | 17 | 34143085 | locus-region | PCGF2 | 0.40531332 | 0.01271578 | 0.64069429 |
| rs9313487 | 5 | 169394879 | intron | DOCK2 | 0.65304879 | 0.54187485 | 0.43957631 |
| rs2227827 | 5 | 76054800 | intron | F2R | 1.27420544 | 0.67563328 | 2.20757565 |
| rs246392 | 5 | 149477865 | intron | PDGFRB | 1.44908755 | 0.19529188 | 0.56867017 |
| rs6476985 | 9 | 5507559 | intron | PDCD1LG2 | 1.81397217 | 0.08389258 | 2.17561674 |
| rs7072398 | 10 | 6119852 | intron | IL2RA | 0.98642587 | 0.95566283 | 0.57726445 |
| rs1041067 | 1 | 158723751 | intron | SLAMF6 | 2.22338393 | 0.00897881 | 0.43080195 |
| rs12667537 | 7 | 157343101 | intron | PTPRN2 | 0.54309148 | 0.03456222 | 0.70517477 |
| rs208250 | 20 | 40849159 | intron | PTPRT | 1.26889064 | 0.34596945 | 1.57736681 |
| rs6214 | 12 | 101317699 | mrna-utr | IGF1 | 1.51571578 | 0.10017662 | 1.61292084 |
| rs10074391 | 5 | 149486896 | intron | PDGFRB | 1.3729007 | 0.49407495 | 2.59859713 |
| rs161042 | 5 | 146166067 | intron | PPP2R2B | 1.37885608 | 0.35142576 | 0.38138725 |
| rs2071336 | 16 | 11969175 | coding-synonymous | TNFRSF17 | 1.84576362 | 0.23985979 | 0.10982398 |
| rs6837303 | 4 | 111189034 | locus-region | ELOVL6 | 0.58664046 | 0.06337587 | 0.69472635 |
| rs3845422 | 1 | 179279594 | intron | MR1 | 0.60462117 | 0.10857967 | 0.56363662 |
| rs1638006 | 7 | 157177926 | intron | PTPRN2 | 0.7297433 | 0.30670775 | 0.62866877 |
| rs161021 | 5 | 146189300 | intron | PPP2R2B | 1.46158082 | 0.27343607 | 0.36047838 |
| rs1003854 | 21 | 44534535 | intron | AIRE | 0.63701493 | 0.15602551 | 0.61640983 |
| rs1378796 | 3 | 158614482 | coding-nonsynonymous | VEPH1 | 0.82036206 | 0.59575804 | 0.52764493 |
| rs12051769 | 17 | 11918677 | intron | MAP2K4 | 0.53301285 | 0.06298351 | 0.64982994 |
| rs3795326 | 1 | 158732980 | intron | SLAMF6 | 1.9796942 | 0.02997707 | 0.31717254 |
| rs7170919 | 15 | 89115963 | intron | BLM | 0.71523388 | 0.27054948 | 0.61102113 |
| rs7130876 | 11 | 48007571 | intron | PTPRJ | 1.36521018 | 0.29227446 | 0.52537558 |
| rs244090 | 20 | 42667504 | intron | PKIG | 1.82658167 | 0.05072084 | 1.86114844 |
| rs424051 | 9 | 9004740 | intron | PTPRD | 0.357172 | 0.00154964 | 0.73786157 |
| rs7246376 | 19 | 8109328 | coding-nonsynonymous | FBN3 | 1.41417418 | 0.2510527 | 1.68780469 |
| rs12959952 | 18 | 46494835 | intron | MAPK4 | 0.75832189 | 0.28250053 | 0.68642326 |
| rs11952962 | 5 | 75931035 | intron | IQGAP2 | 1.96820647 | 0.02211585 | 1.41785272 |
| rs246394 | 5 | 149478344 | intron | PDGFRB | 1.15547435 | 0.61541144 | 0.63067265 |
| rs12325842 | 17 | 11935497 | intron | MAP2K4 | 0.54254452 | 0.08441604 | 0.64627154 |
| rs17763453 | 17 | 3664884 | intron | C17orf85 | 1.92846791 | 0.0172052 | 1.89696314 |
| rs4472605 | 9 | 34556190 | intron | CNTFR | 2.29595354 | 0.01632828 | 1.45596316 |
| rs926479 | 20 | 40786436 | intron | PTPRT | 1.25796536 | 0.71984049 | 2.59667403 |
| rs2071081 | 12 | 6805892 | locus-region | LEPREL2 | 1.16018832 | 0.62051063 | 1.72458275 |
| rs7690305 | 4 | 15575064 | — | — | 0.6947075 | 0.28024405 | 0.57017516 |
| rs244076 | 20 | 42686329 | coding-synonymous | ADA | 1.79952848 | 0.05747238 | 1.8756407 |
| rs6621980 | 23 | 104690227 | intron | IL1RAPL2 | 1.20558533 | 0.30138287 | 1.3068943 |
| rs6742576 | 2 | 239852569 | intron | HDAC4 | 2.04564913 | 0.04916586 | 1.55889951 |
| rs866484 | 1 | 157253101 | coding-nonsynonymous | IFI16 | 1.34340774 | 0.32362484 | 1.56924172 |
| rs3797390 | 5 | 75942821 | intron | IQGAP2 | 2.35975324 | 0.00250135 | 1.20099738 |
| rs1264456 | 6 | 30570063 | — | — | 0.60087622 | 0.05481569 | 0.6298167 |
| rs6065467 | 20 | 40432747 | intron | PTPRT | 0.66417197 | 0.30045815 | 0.56971475 |
| rs3736395 | 5 | 75924224 | intron | IQGAP2 | 2.01317446 | 0.01786271 | 1.38697287 |
| rs9892152 | 17 | 59755697 | intron | PECAM1 | 1.28015545 | 0.30060169 | 1.79832413 |
| rs4955104 | 3 | 30696707 | intron | TGFBR2 | 1.73311846 | 0.09135101 | 1.70995826 |
| rs1007212 | 15 | 97101441 | intron | IGF1R | 1.58554575 | 0.06881669 | 1.27530638 |
| rs2296449 | 1 | 117380273 | intron | IGSF2 | 0.28435755 | 0.2386029 | 0.47588685 |
| rs832517 | 12 | 93164318 | intron | PLXNC1 | 0.73260276 | 0.2419302 | 0.68112858 |
| rs5743220 | 11 | 43299325 | intron | API5 | 0.82693415 | 0.64066747 | 2.44655616 |
| rs8086815 | 18 | 8163669 | intron | PTPRM | 1.13288097 | 0.73780601 | 1.6337126 |
| rs3733678 | 5 | 149491985 | intron | PDGFRB | 1.56157271 | 0.31028198 | 2.06780589 |
| rs246395 | 5 | 149479865 | coding-synonymous | PDGFRB | 1.43776518 | 0.19768884 | 0.6194716 |
| rs613613 | 9 | 9004274 | intron | PTPRD | 0.24492626 | 0.00030665 | 0.83677802 |
| rs10406354 | 19 | 59022044 | — | — | 0.84350808 | 0.63607216 | 0.52404025 |
| rs1105238 | 1 | 159948285 | intron | FCRLA | 1.57425902 | 0.08700505 | 1.35815008 |
| rs4724231 | 7 | 43608739 | intron | STK17A | 0.79408653 | 0.52206122 | 0.37564254 |
| rs2179694 | 6 | 128405416 | intron | PTPRK | 2.72734178 | 0.00371434 | 1.10418786 |
| rs210431 | 23 | 104831589 | intron | IL1RAPL2 | 1.15706404 | 0.41697392 | 1.25792622 |
| rs17671456 | 8 | 22441022 | intron | PPP3CC | 1.62279091 | 0.18971454 | 1.60308204 |
| rs17283264 | 3 | 46228570 | — | — | 1.71885877 | 0.13929326 | 6.6280982 |
| rs2279590 | 8 | 27512170 | intron | CLU | 0.88843705 | 0.64964423 | 1.75040285 |
| rs1050382 | 17 | 59753732 | locus-region | PECAM1 | 1.28401592 | 0.30420932 | 1.74401131 |
| rs6917187 | 6 | 128870789 | intron | PTPRK | 1.30160689 | 0.56966629 | 0.46217996 |
| rs933226 | 22 | 30673847 | intron | YWHAH | 1.12742146 | 0.73874752 | 1.98104948 |
| rs3024486 | 6 | 6090408 | mrna-utr | F13A1 | 1.88372078 | 0.23198551 | 8.87599881 |
| rs4698806 | 4 | 111190938 | mrna-utr | ELOVL6 | 0.57535324 | 0.05772595 | 0.75961836 |
| rs4756331 | 11 | 36602169 | intron | C11orf74 | 4.6856564 | 0.03167379 | 2.27441112 |

TABLE 3-continued

| | | | | | | | |
|---|---|---|---|---|---|---|---|
| rs10772120 | 12 | 9801678 | intron | CD69 | 0.65812083 | 0.15886236 | 0.65374546 |
| rs4820059 | 22 | 30676468 | intron | YWHAH | 0.89142053 | 0.67014566 | 1.72048152 |
| rs7099752 | 10 | 129641321 | intron | PTPRE | 0.81583787 | 0.56389734 | 0.6887796 |
| rs10797666 | 1 | 179285422 | intron | MR1 | 0.6992695 | 0.22630081 | 0.58684061 |
| rs831603 | 11 | 33715214 | — | — | 0.73586214 | 0.24049237 | 0.69047971 |
| rs1519602 | 2 | 196736037 | intron | STK17B | 0.57178709 | 0.03485524 | 0.73904041 |
| rs638251 | 18 | 7786393 | intron | PTPRM | 0.92267206 | 0.75903463 | 0.60830628 |
| rs7541171 | 1 | 71179181 | intron | PTGER3 | 0.77336148 | 0.38262508 | 0.55588639 |
| rs793816 | 4 | 185591486 | intron | IRF2 | 0.39268627 | 0.40453998 | 0.23730079 |
| rs805287 | 6 | 31786709 | locus-region | C6orf21 | 0.57505168 | 0.05667066 | 0.69044701 |
| rs2844463 | 6 | 31723146 | intron | BAT3 | 0.37152482 | 0.02080519 | 0.7124517 |
| rs11237451 | 11 | 77703107 | intron | GAB2 | 0.6976664 | 0.24743993 | 0.73454025 |
| rs496888 | 1 | 12155393 | intron | TNFRSF1B | 0.98980954 | 0.97027764 | 0.58209238 |
| rs2163057 | 3 | 32514492 | intron | CMTM6 | 0.67697442 | 0.14595214 | 0.70525773 |
| rs2283539 | 16 | 24036462 | intron | PRKCB1 | 1.34410531 | 0.26558516 | 1.67553526 |
| rs4253655 | 22 | 44947835 | intron | PPARA | 1.91645477 | 0.04617801 | 1.54643399 |
| rs1075846 | 5 | 149484351 | intron | PDGFRB | 0.98153804 | 0.94437916 | 0.6804459 |
| rs10836342 | 11 | 35198213 | intron | CD44 | 1.39906967 | 0.22563757 | 1.55571501 |
| rs17419586 | 13 | 23148712 | locus-region | TNFRSF19 | 1.0920234 | 0.74357188 | 1.8778521 |
| rs2076846 | 10 | 6103259 | intron | IL2RA | 1.01897585 | 0.94283005 | 0.59088718 |
| rs17110948 | 5 | 149498698 | intron | PDGFRB | 0.75555493 | 0.58881604 | 0.49768788 |
| rs7289754 | 22 | 20926259 | — | — | 2.29698009 | 0.00141594 | 1.08058008 |
| rs3736101 | 11 | 47263204 | coding-nonsynonymous | MADD | 1.97297758 | 0.05712124 | 2.67813862 |
| rs10807350 | 6 | 47336871 | intron | TNFRSF21 | 0.90243854 | 0.76800828 | 2.03966167 |
| rs2575674 | 4 | 87156570 | locus-region | MAPK10 | 1.06794408 | 0.82242424 | 0.58503629 |
| rs1436522 | 4 | 87183196 | intron | MAPK10 | 0.81807545 | 0.56253571 | 0.61156718 |
| rs2869460 | 4 | 77140838 | locus-region | CXCL9 | 0.70455921 | 0.3038615 | 0.58827213 |
| rs12881815 | 14 | 63674348 | coding-nonsynonymous | SYNE2 | 4.89460691 | 0.00447504 | 3.27810424 |
| rs2302267 | 23 | 12795499 | intron | TLR7 | 1.92239964 | 0.0134585 | 1.4130263 |
| rs4966019 | 15 | 97091849 | intron | IGF1R | 1.67417263 | 0.03214425 | 1.21425194 |
| rs6482647 | 10 | 129716363 | intron | PTPRE | 0.89887749 | 0.66494004 | 0.74977347 |
| rs4027402 | 14 | 63566502 | coding-nonsynonymous | SYNE2 | 0.39821095 | 0.03035231 | 0.76414481 |
| rs10789841 | 11 | 110974792 | — | — | 1.53893299 | 0.09589358 | 0.47137687 |
| rs1983165 | 3 | 62059196 | intron | PTPRG | 0.76500869 | 0.39230788 | 0.6522553 |
| rs6670616 | 1 | 71167471 | intron | PTGER3 | 0.74220682 | 0.31748959 | 0.58708357 |
| rs896769 | 7 | 157770740 | intron | PTPRN2 | 0.49460614 | 0.35898709 | 0.43950595 |
| rs1984399 | 20 | 40312545 | intron | PTPRT | 1.35296357 | 0.22045301 | 1.46992979 |
| rs4955272 | 3 | 32288680 | intron | CMTM8 | 0.92003691 | 0.78923423 | 0.60948044 |
| rs2869461 | 4 | 77139917 | locus-region | CXCL9 | 1.26643088 | 0.53864183 | 1.85274565 |
| rs2286414 | 7 | 157167781 | intron | PTPRN2 | 2.49603643 | 0.05177127 | 3.78156695 |
| rs878081 | 21 | 44532705 | coding-synonymous | AIRE | 0.68171151 | 0.22702226 | 0.66315301 |
| rs791587 | 10 | 6128705 | intron | IL2RA | 0.84136254 | 0.4815192 | 0.64120998 |
| rs4902264 | 14 | 63561448 | coding-nonsynonymous | SYNE2 | 0.41633694 | 0.03348373 | 1.91932441 |
| rs13172280 | 5 | 35063668 | intron | AGXT2 | 1.30656633 | 0.28540035 | 1.73502557 |
| rs2569190 | 5 | 139993100 | intron | CD14 | 1.50756038 | 0.1077863 | 1.59274474 |
| rs660769 | 5 | 131422350 | locus-region | IL3 | 1.30221156 | 0.69582292 | 0.42665893 |
| rs6016685 | 20 | 40173215 | intron | PTPRT | 0.92951872 | 0.79976593 | 0.59082396 |
| rs6060855 | 20 | 29762606 | intron | BCL2L1 | 1.04395 | 0.92304559 | 0.43117643 |
| rs4752896 | 11 | 48086525 | intron | PTPRJ | 3.72708636 | 0.00528618 | 1.57506212 |
| rs244091 | 20 | 42664524 | intron | PKIG | 1.94653493 | 0.04751127 | 1.75887237 |
| rs2070783 | 17 | 59760703 | intron | PECAM1 | 1.23734492 | 0.37520045 | 1.75467319 |
| rs169142 | 16 | 24039431 | intron | PRKCB1 | 0.67901527 | 0.10717015 | 0.71324157 |
| rs2335478 | 7 | 157569741 | intron | PTPRN2 | 1.58188687 | 0.42862493 | 0.39743275 |
| rs10514071 | 5 | 76029967 | intron | IQGAP2 | 1.65941384 | 0.07707822 | 1.2178954 |
| rs3828016 | 20 | 1865290 | intron | SIRPA | 0.52852523 | 0.02160896 | 0.70944458 |
| rs1457238 | 2 | 160693708 | intron | ITGB6 | 0.97020126 | 0.91163481 | 0.72059793 |
| rs11015985 | 10 | 129669308 | intron | PTPRE | 0.94083493 | 0.84162285 | 0.67420508 |
| rs12001295 | 9 | 5508260 | intron | PDCD1LG2 | 1.79243904 | 0.2162097 | 1.95909625 |
| rs2267908 | 20 | 1857920 | intron | SIRPA | 1.68171221 | 0.04729491 | 1.23185694 |
| rs12625871 | 20 | 40208063 | intron | PTPRT | 0.68842184 | 0.47143938 | 0.51747943 |
| rs1058240 | 10 | 8156604 | mrna-utr | GATA3 | 0.7565952 | 0.4352407 | 0.60486059 |
| rs9310940 | 3 | 30697222 | intron | TGFBR2 | 1.74983449 | 0.02369938 | 1.26424017 |
| rs12814009 | 12 | 15399298 | intron | PTPRO | 0.26356574 | 0.01629732 | 0.64133422 |
| rs7559522 | 2 | 45903540 | intron | PRKCE | 1.01249362 | 0.95884972 | 0.65154256 |
| rs1797647 | 12 | 12143345 | mrna-utr | BCL2L14 | 0.67892026 | 0.1815313 | 0.74897192 |
| rs304839 | 3 | 30706286 | intron | TGFBR2 | 1.70927667 | 0.0746808 | 1.27375763 |
| rs10972149 | 9 | 34551160 | intron | CNTFR | 1.88131724 | 0.06984944 | 1.40551155 |
| rs2069933 | 2 | 127902158 | intron | PROC | 1.5322374 | 0.08604038 | 1.41197006 |
| rs12969613 | 18 | 65710412 | intron | CD226 | 0.91036251 | 0.7111396 | 0.73759216 |
| rs2275603 | 1 | 159948404 | coding-nonsynonymous | FCRLA | 1.4835256 | 0.13666372 | 1.33588972 |
| rs1044141 | 7 | 43630805 | coding-nonsynonymous | STK17A | 1.37913032 | 0.28521545 | 1.54280229 |
| rs1007822 | 18 | 65706201 | intron | CD226 | 0.91036251 | 0.7111396 | 0.73861498 |
| rs7692976 | 4 | 111131016 | intron | EGF | 0.83961089 | 0.48533216 | 0.72312756 |
| rs4485556 | 2 | 219865662 | intron | PTPRN | 1.09221296 | 0.78285734 | 2.06334949 |
| rs2231375 | 1 | 144408051 | intron | CD160 | 0.74115317 | 0.2635782 | 0.69538709 |
| rs2242660 | 6 | 31705732 | intron | BAT2 | 0.76945122 | 0.35472586 | 0.63732275 |
| rs7732671 | 5 | 149192436 | coding-nonsynonymous | PPARGC1B | 2.89131579 | 0.00898077 | 1.55843339 |
| rs17834679 | 19 | 56961899 | intron | FPRL1 | 0.59646363 | 0.07510676 | 0.67581905 |
| rs2838733 | 21 | 45148159 | intron | ITGB2 | 1.41619634 | 0.20650687 | 1.4139189 |
| rs13173943 | 5 | 35037762 | intron | AGXT2 | 1.41575487 | 0.17774415 | 1.76018633 |

TABLE 3-continued

| SNP | Chr | Position | Region | Gene | | | |
|---|---|---|---|---|---|---|---|
| rs4462251 | 10 | 129749982 | intron | PTPRE | 0.71790728 | 0.18078977 | 0.6649517 |
| rs2305340 | 12 | 7157242 | — | — | 0.42720319 | 0.03847928 | 0.73801084 |
| rs12451415 | 17 | 11947505 | intron | MAP2K4 | 0.38601795 | 0.01940391 | 0.74534892 |
| rs2595204 | 2 | 46047369 | intron | PRKCE | 1.04828765 | 0.8648604 | 1.57921594 |
| rs6021183 | 20 | 49455556 | intron | NFATC2 | 1.27572604 | 0.48092282 | 2.90323676 |
| rs17113227 | 11 | 111125701 | intron | PPP2R1B | 1.31079147 | 0.28991073 | 4.48E−73 |
| rs11833550 | 12 | 9899947 | intron | CLEC2B | 1.43123546 | 0.28432538 | 1.47738548 |
| rs310247 | 1 | 65079997 | intron | JAK1 | 1.49052622 | 0.12938444 | 1.44027852 |
| rs17875513 | 15 | 79379439 | coding-nonsynonymous | IL16 | 2.09E−10 | 0.99976301 | 0.10166663 |
| rs910682 | 6 | 112282428 | intron | FYN | 2.12093972 | 0.0119868 | Inf |
| rs4245886 | 3 | 32279107 | intron | CMTM8 | 0.7970233 | 0.41988177 | 0.73876461 |
| rs12185980 | 3 | 107031592 | intron | CBLB | 3.323853 | 0.00050792 | 1.56530554 |
| rs2255364 | 12 | 10423163 | intron | KLRK1 | 0.5616856 | 0.08521285 | 1.56368161 |
| rs2268890 | 2 | 162580738 | intron | DPP4 | 0.65149321 | 0.09885744 | 1.20E+25 |
| rs6058391 | 20 | 29743569 | intron | BCL2L1 | 1.11886253 | 0.80671459 | 0.44238887 |
| rs7647903 | 3 | 3108791 | intron | IL5RA | 1.87725168 | 0.02334544 | 1.23815585 |
| rs5996577 | 22 | 22251427 | intron | IGLL1 | 1.92827739 | 0.037121 | 1.72345433 |
| rs6580942 | 12 | 51948891 | coding-nonsynonymous | ESPL1 | 1.18080511 | 0.54440371 | 1.46959364 |
| rs241430 | 6 | 32910798 | intron | TAP2 | 0.53117149 | 0.02212076 | 1.69161859 |
| rs706121 | 9 | 33250632 | intron | BAG1 | 0.86147211 | 0.63269212 | 2.22530992 |
| rs2295616 | 1 | 158976781 | intron | SLAMF7 | 0.82924496 | 0.49284778 | 0.58465681 |
| rs6829390 | 4 | 47893743 | intron | TEC | 1.7333281 | 0.14893786 | 3.03190369 |
| rs9817149 | 3 | 191740949 | intron | IL1RAP | 2.32356443 | 0.05341758 | 1.86248097 |
| rs599563 | 1 | 117014117 | — | — | 0.52790505 | 0.12915023 | 0.20622181 |
| rs2238337 | 15 | 89156736 | intron | BLM | 1.54569338 | 0.08136811 | 1.50742576 |
| rs3816724 | 11 | 47268621 | intron | MADD | 1.81113639 | 0.10869127 | 2.65901484 |
| rs970283 | 20 | 40713729 | intron | PTPRT | 1.46306145 | 0.4018486 | 0.54068963 |
| rs3733236 | 4 | 77143022 | mrna-utr | CXCL9 | 1.15699539 | 0.71638395 | 1.83954612 |
| rs10854166 | 19 | 18513844 | intron | FKBP8 | 1.03811743 | 0.87944921 | 1.47150955 |
| rs6850557 | 4 | 111130464 | intron | EGF | 1.19374349 | 0.51028325 | 0.61087182 |
| rs4572808 | 3 | 32292718 | intron | CMTM8 | 1.1777916 | 0.53590471 | 1.32095634 |
| rs875258 | 11 | 111035817 | intron | SNF1LK2 | 1.21639487 | 0.45485149 | Inf |
| rs1131510 | 10 | 35339091 | mrna-utr | CUL2 | 1.04488097 | 0.93034401 | 0.32944623 |
| rs10497208 | 2 | 160695167 | intron | ITGB6 | 0.97020126 | 0.91163481 | 0.73334585 |
| rs10104302 | 8 | 57030794 | intron | LYN | 1.23920621 | 0.4864228 | 1.44246121 |
| rs728373 | 20 | 40278187 | intron | PTPRT | 1.35050667 | 0.2291808 | 1.37699658 |
| rs10977434 | 9 | 8991075 | intron | PTPRD | 1.26538151 | 0.35953996 | 1.59504212 |
| rs12039194 | 1 | 162803852 | intron | PBX1 | 0.91594261 | 0.82318503 | 0.52789908 |
| rs2853884 | 22 | 30678313 | intron | YWHAH | 1.0223608 | 0.93977544 | 1.49159144 |
| rs5743740 | 23 | 12801881 | intron | TLR7 | 1.71683397 | 0.03335376 | 1.53079545 |
| rs7359387 | 16 | 68291166 | mrna-utr | NFAT5 | 0.72860948 | 0.42312929 | 0.5709194 |

| SNP | HIGS P | MIBS Odds | MIBS P | Meta Odds | Meta P |
|---|---|---|---|---|---|
| rs12368829 | 1.55E−07 | 1.887207952 | 0.56468936 | 0.27311013 | 5.08E−07 |
| rs11744216 | 1.44E−05 | 0.370067427 | 0.28008697 | 0.30667899 | 3.56E−06 |
| rs4147385 | 0.00046696 | 0.847419164 | 0.67342809 | 2.13745578 | 9.22E−06 |
| rs12546235 | 9.63E−06 | 0.258959962 | 0.19881566 | 0.43388002 | 1.11E−05 |
| rs10054825 | 0.0001897 | 0.514031922 | 0.25064205 | 0.3743547 | 2.21E−05 |
| rs17535213 | 4.45E−06 | 0.588339124 | 0.31166083 | 0.57027044 | 4.02E−05 |
| rs10072056 | 0.00074227 | 0.414680192 | 0.0012715 | 0.60837768 | 5.84E−05 |
| rs1863993 | 0.44319157 | 4.427219418 | 0.00214385 | 3.88981038 | 8.36E−05 |
| rs4242389 | 8.81E−06 | 0.538507051 | 0.52261252 | 0.49632251 | 0.00011364 |
| rs17725712 | 0.01195522 | 2.373592311 | 0.01979588 | 2.50759989 | 0.00016535 |
| rs11773821 | 0.0008452 | 0.518178068 | 0.13897121 | 0.54041127 | 0.00033105 |
| rs414634 | 0.00177128 | 0.981460036 | 0.95270754 | 1.62246205 | 0.00033946 |
| rs1882019 | 0.00575273 | 0.47389969 | 0.04123021 | 0.53629298 | 0.00034044 |
| rs13206518 | 0.02930569 | 0.117803784 | 0.00019143 | 0.39427174 | 0.00035099 |
| rs927335 | 0.01410875 | 2.78864964 | 0.01285391 | 1.69891458 | 0.00036195 |
| rs6482644 | 0.24768847 | 0.247282655 | 6.13E−05 | 0.57798945 | 0.00040403 |
| rs4077341 | 0.00519201 | 0.608350511 | 0.14814984 | 0.63448794 | 0.00042665 |
| rs1884564 | 0.00016232 | 0.787331851 | 0.64569651 | 0.55434198 | 0.00051894 |
| rs3826392 | 0.0084676 | 0.693166599 | 0.2022867 | 0.6309839 | 0.00053597 |
| rs390406 | 0.00011495 | 1.176428114 | 0.70671054 | 0.56597223 | 0.00053686 |
| rs440238 | 0.04195541 | 0.703829319 | 0.29007635 | 0.62008121 | 0.00057369 |
| rs9482888 | NA | 6.819490938 | 0.05718065 | 6.50375409 | 0.00058077 |
| rs2596606 | 0.00317447 | 1.288186948 | 0.42621042 | 1.75806233 | 0.00058124 |
| rs17652304 | 0.49335132 | 4.891979443 | 0.0296099 | 3.55426184 | 0.00062941 |
| rs3815003 | 0.00175443 | 0.705967504 | 0.29860931 | 0.62769907 | 0.00064177 |
| rs2278324 | 0.00282462 | 0.665950988 | 0.42252987 | 1.78495491 | 0.00068524 |
| rs805274 | 0.01306354 | 0.609404792 | 0.18569727 | 0.60696173 | 0.0006948 |
| rs8005905 | 0.0003978 | 1.414706274 | 0.44027301 | 0.52877353 | 0.00072601 |
| rs2879097 | 0.00665552 | 0.885200263 | 0.72785514 | 0.63044699 | 0.00079205 |
| rs9313487 | 0.0034416 | 0.23366225 | 0.08429415 | 0.43740777 | 0.0008986 |
| rs2227827 | 0.26149332 | 5.68943527 | 0.00020765 | 2.92049655 | 0.00092929 |
| rs246392 | 0.00056846 | 0.459335521 | 0.00673323 | 0.6561279 | 0.0009419 |
| rs6476985 | 0.00536715 | 1.445669754 | 0.41300509 | 1.89994931 | 0.00102191 |
| rs7072398 | 0.00039605 | 0.688487285 | 0.2008706 | 0.6750759 | 0.00102242 |
| rs1041067 | NA | 2.060320517 | 0.04779645 | 2.15467293 | 0.00106064 |
| rs12667537 | 0.02875229 | 0.597491768 | 0.14322394 | 0.65395062 | 0.00107733 |

TABLE 3-continued

| | | | | | |
|---|---|---|---|---|---|
| rs208250 | 0.00614501 | | 1.840718802 | 0.07640046 | 1.52317417 | 0.00109109 |
| rs6214 | 0.0038546 | | 1.188058954 | 0.61245743 | 1.51987444 | 0.00109655 |
| rs10074391 | 0.01865724 | | 2.594822575 | 0.01436067 | 2.18771054 | 0.00112369 |
| rs161042 | 2.05E−05 | | 0.652465532 | 0.233342 | 0.58028375 | 0.00114124 |
| rs2071336 | 5.19E−07 | | 0.428886818 | 0.29502796 | 0.36521665 | 0.00117968 |
| rs6837303 | 0.03179239 | | 0.572171902 | 0.09253608 | 0.6489751 | 0.00122167 |
| rs3845422 | 0.00278781 | | 0.888862119 | 0.7473235 | 0.61787249 | 0.00126245 |
| rs1638006 | 0.00560578 | | 0.606535032 | 0.17368201 | 0.64416528 | 0.00128998 |
| rs161021 | 7.72E−06 | | 0.708220637 | 0.35425816 | 0.57994142 | 0.00131834 |
| rs1003854 | 0.00808487 | | 0.658007833 | 0.25304841 | 0.62708448 | 0.00132688 |
| rs1378796 | 0.00049546 | | 0.883688589 | 0.74236331 | 0.6161596 | 0.00132949 |
| rs12051769 | 0.00843671 | | 0.794312841 | 0.45113646 | 0.65464663 | 0.00141068 |
| rs3795326 | NA | | 2.279926623 | 0.01881296 | 2.10832635 | 0.00145114 |
| rs7170919 | 0.00547374 | | 0.654104992 | 0.24394214 | 0.63862525 | 0.00149694 |
| rs7130876 | 0.00026877 | | 0.369125944 | 0.02598111 | 0.63472671 | 0.00155036 |
| rs244090 | 0.00918138 | | 1.243594423 | 0.53464137 | 1.69120653 | 0.00156555 |
| rs424051 | 0.08378924 | | 0.718400103 | 0.35041277 | 0.64014939 | 0.00164957 |
| rs7246376 | 0.01577555 | | 2.427149459 | 0.0560574 | 1.67623062 | 0.00170637 |
| rs12959952 | 0.05307649 | | 0.446458552 | 0.00878972 | 0.64752915 | 0.00171155 |
| rs11952962 | 0.14102305 | | 2.023094389 | 0.0652907 | 1.68301113 | 0.00177679 |
| rs246394 | 0.00452891 | | 0.449778283 | 0.00878434 | 0.67006344 | 0.00180216 |
| rs12325842 | 0.01057338 | | 0.770807589 | 0.41269576 | 0.65064375 | 0.00190847 |
| rs17763453 | 0.01033902 | | 1.010710537 | 0.97540609 | 1.65815902 | 0.00193618 |
| rs4472605 | 0.05529258 | | 1.745523547 | 0.23595804 | 1.6397061 | 0.00203956 |
| rs926479 | 0.07353594 | | 7.99520442 | 0.00126005 | 2.90414967 | 0.00204443 |
| rs2071081 | 0.01771513 | | 1.911456413 | 0.0218428 | 1.60296551 | 0.00207988 |
| rs7690305 | 0.00290621 | | 0.824326571 | 0.64212974 | 0.62430077 | 0.00208977 |
| rs244076 | 0.01007464 | | 1.204884408 | 0.59491143 | 1.6732152 | 0.00221531 |
| rs6621980 | 0.04939986 | | 1.775653247 | 0.01210697 | 1.35035351 | 0.00223866 |
| rs6742576 | 0.06345516 | | 1.768951867 | 0.12128795 | 1.7093299 | 0.00227372 |
| rs866484 | 0.06374432 | | 2.22598424 | 0.01233101 | 1.64048747 | 0.00231235 |
| rs3797390 | 0.35032961 | | 1.689002991 | 0.07241573 | 1.53728435 | 0.00232497 |
| rs1264456 | 0.00245695 | | 1.465610843 | 0.3087658 | 0.6842054 | 0.00235738 |
| rs6065467 | 0.00162751 | | 1.332110088 | 0.60420493 | 0.6243462 | 0.00254874 |
| rs3736395 | 0.17646102 | | 1.931419031 | 0.09472133 | 1.66559675 | 0.0025506 |
| rs9892152 | 0.00076293 | | 1.035878616 | 0.89700987 | 1.45816281 | 0.00256015 |
| rs4955104 | 0.01159083 | | 1.267402965 | 0.47637974 | 1.60475149 | 0.00258158 |
| rs1007212 | 0.16726864 | | 2.270349904 | 0.01221697 | 1.4869906 | 0.00269972 |
| rs2296449 | 0.05303457 | | 0.252264495 | 0.03143414 | 0.39039884 | 0.00278836 |
| rs832517 | 0.01733639 | | 0.641773703 | 0.15867567 | 0.68581238 | 0.00283581 |
| rs5743220 | 0.00754993 | | 2.215631346 | 0.01089829 | 1.81228752 | 0.00284212 |
| rs8086815 | 0.04966726 | | 5.059080213 | 0.00088215 | 1.76520819 | 0.00293494 |
| rs3733678 | 0.02996296 | | 2.076872691 | 0.06617482 | 1.92823675 | 0.00300019 |
| rs246395 | 0.00236794 | | 0.46651283 | 0.00816981 | 0.69198318 | 0.00301278 |
| rs613613 | 0.33851924 | | 0.489338494 | 0.06231333 | 0.63373233 | 0.00303403 |
| rs10406354 | 0.00121281 | | 0.862175398 | 0.72870567 | 0.6194692 | 0.00304803 |
| rs1105238 | 0.10163662 | | 2.428288153 | 0.02817001 | 1.52456935 | 0.00317617 |
| rs4724231 | 0.00020324 | | 1.552093052 | 0.46472493 | 0.55470559 | 0.00329302 |
| rs2179694 | 0.64770879 | | 2.925008861 | 0.00555316 | 1.6268167 | 0.0033713 |
| rs210431 | 0.06991452 | | 1.942062547 | 0.0046256 | 1.31935745 | 0.00342114 |
| rs17671456 | 0.06629775 | | 2.201374994 | 0.04659244 | 1.72457302 | 0.00342623 |
| rs17283264 | 0.00148629 | | 1.526652324 | 0.53071016 | 2.2848273 | 0.00352712 |
| rs2279590 | 0.00106384 | | 1.676816197 | 0.11287341 | 1.46446386 | 0.00357173 |
| rs1050382 | 0.00167956 | | 1.062141736 | 0.83590345 | 1.45390139 | 0.00357423 |
| rs6917187 | 9.24E−05 | | 2.057353645 | 0.23760335 | 0.60379164 | 0.00375548 |
| rs933226 | 0.01337494 | | 2.189801618 | 0.04098616 | 1.73409156 | 0.00381266 |
| rs3024486 | 0.01728117 | | 2.856438354 | 0.06567196 | 2.80749677 | 0.00387647 |
| rs4698806 | 0.11030964 | | 0.527501004 | 0.06278053 | 0.67517857 | 0.00390396 |
| rs4756331 | 0.17190288 | | 2.903606511 | 0.11955976 | 3.01226743 | 0.00395009 |
| rs10772120 | 0.01168965 | | 0.821815393 | 0.59634724 | 0.6752583 | 0.00397005 |
| rs4820059 | 0.00287257 | | 1.914602607 | 0.04428658 | 1.48141208 | 0.00404405 |
| rs7099752 | 0.05956565 | | 0.404212531 | 0.00954005 | 0.64097952 | 0.00405109 |
| rs10797666 | 0.00330048 | | 0.991516881 | 0.98022829 | 0.667058 | 0.00408808 |
| rs831603 | 0.03075735 | | 0.584849703 | 0.11700827 | 0.6846441 | 0.00416496 |
| rs1519602 | 0.08236304 | | 0.674616309 | 0.24306781 | 0.68252708 | 0.00424479 |
| rs638251 | 0.00136003 | | 0.86397335 | 0.61888292 | 0.70643279 | 0.00426573 |
| rs7541717 | 0.00269427 | | 0.907922766 | 0.81093925 | 0.64956179 | 0.00430369 |
| rs793816 | 0.00578488 | 18864431544 | | NA | 0.25951327 | 0.00431797 |
| rs805287 | 0.0476095 | | 0.712027543 | 0.34602151 | 0.66328443 | 0.0043842 |
| rs2844463 | 0.08520158 | | 0.507172313 | 0.16989179 | 0.61948187 | 0.00443233 |
| rs11237451 | 0.06356768 | | 0.38639699 | 0.01979918 | 0.67561604 | 0.00449866 |
| rs496888 | 0.00079136 | | 0.869651538 | 0.64305507 | 0.69866146 | 0.00451876 |
| rs2163057 | 0.03329755 | | 0.730665214 | 0.22869821 | 0.70474573 | 0.00454599 |
| rs2283539 | 0.01026196 | | 1.33256674 | 0.35974288 | 1.49931704 | 0.00454803 |
| rs4253655 | 0.0722436 | | 1.587743147 | 0.29093345 | 1.65541438 | 0.00459501 |
| rs1075846 | 0.01175816 | | 0.598391802 | 0.05711767 | 0.71375152 | 0.00461622 |
| rs10836342 | 0.06567563 | | 2.103285337 | 0.04913566 | 1.58639988 | 0.00478853 |
| rs17419586 | 0.00291577 | | 1.546743596 | 0.22555031 | 1.52993899 | 0.00486913 |
| rs2076846 | 0.00126669 | | 0.764492866 | 0.4048416 | 0.69945436 | 0.00498422 |
| rs17110948 | 0.01809374 | | 0.43135505 | 0.10282208 | 0.52503672 | 0.00502749 |

TABLE 3-continued

| | | | | | |
|---|---|---|---|---|---|
| rs7289754 | 0.67991022 | 1.714354514 | 0.06533309 | 1.46058131 | 0.00505693 |
| rs3736101 | 0.01446908 | 1.178560299 | 0.71300002 | 1.90168302 | 0.0050709 |
| rs10807350 | 0.02125369 | 4.20106486 | 0.00152376 | 1.78016031 | 0.00510485 |
| rs2575674 | 0.00106201 | 0.792678685 | 0.4959151 | 0.69155684 | 0.00515029 |
| rs1436522 | 0.00435674 | 0.830657396 | 0.6115842 | 0.67275763 | 0.00532612 |
| rs2869460 | 0.0026252 | 1.091040447 | 0.80696993 | 0.67117457 | 0.00542323 |
| rs12881815 | 0.07772938 | 0.180040381 | 0.20551442 | 3.11823429 | 0.00551016 |
| rs2302267 | 0.30851561 | 1.426821775 | 0.25585508 | 1.61823347 | 0.00555203 |
| rs4966019 | 0.26208827 | 2.218014617 | 0.03331489 | 1.43993702 | 0.0055734 |
| rs6482647 | 0.06781404 | 0.385514916 | 0.003037 | 0.71192776 | 0.0056319 |
| rs4027402 | NA | 0.417903186 | 0.08455622 | 0.4062491 | 0.00564909 |
| rs10789841 | NA | 1.857069082 | 0.02350067 | 1.68198515 | 0.00566318 |
| rs1983165 | 0.03014415 | 0.549314197 | 0.10127566 | 0.65739732 | 0.00570624 |
| rs6670616 | 0.00682232 | 0.838342811 | 0.65037355 | 0.65817696 | 0.00571641 |
| rs896769 | 0.00736724 | 0.753842335 | 0.64705164 | 0.48971626 | 0.00577494 |
| rs1984399 | 0.0342318 | 1.525981289 | 0.1905506 | 1.44393491 | 0.00587133 |
| rs4955272 | 0.00517256 | 0.718705374 | 0.30795068 | 0.6819244 | 0.00590934 |
| rs2869461 | 0.01548032 | 1.861727809 | 0.14918366 | 1.68896622 | 0.00591907 |
| rs2286414 | 0.05552253 | 2.007269628 | 0.50111889 | 2.72399091 | 0.00597573 |
| rs878081 | 0.0286662 | 0.695807839 | 0.25365564 | 0.6735551 | 0.0060638 |
| rs791587 | 0.01422135 | 0.688406679 | 0.18017542 | 0.70198049 | 0.00615988 |
| rs4902264 | NA | 0.417903186 | 0.08455622 | 0.41696109 | 0.00618391 |
| rs13172280 | 0.0036724 | 1.039486719 | 0.90369822 | 1.45208431 | 0.00635965 |
| rs2569190 | 0.00646771 | 0.880141582 | 0.69107942 | 1.42512534 | 0.00638771 |
| rs660597 | 0.00578686 | 0.138854042 | 0.06951693 | 0.4765705 | 0.00640015 |
| rs6016685 | 0.00271653 | 0.791056985 | 0.56022757 | 0.68182883 | 0.00640311 |
| rs6060855 | 0.00181195 | 0.66791201 | 0.40088926 | 0.56756344 | 0.0064531 |
| rs4752896 | 0.16126432 | 1.391028202 | 0.48894885 | 1.88703405 | 0.00645468 |
| rs244091 | 0.0259514 | 1.101451332 | 0.78546353 | 1.61261944 | 0.00660832 |
| rs2070783 | 0.00171067 | 1.016006939 | 0.95267953 | 1.40916934 | 0.00673216 |
| rs169142 | 0.0696807 | 0.698087802 | 0.22388372 | 0.69977491 | 0.00674726 |
| rs2335478 | 0.00244836 | 0.374723896 | 0.13478287 | 0.50898606 | 0.00676621 |
| rs10514071 | 0.39124357 | 2.669520125 | 0.00978668 | 1.55132811 | 0.00677526 |
| rs3828016 | 0.04488799 | 0.931914458 | 0.80457051 | 0.70395066 | 0.00680458 |
| rs1457238 | 0.03083353 | 0.448765762 | 0.01536078 | 0.71699591 | 0.00686438 |
| rs11015985 | 0.03157349 | 0.443734676 | 0.02237032 | 0.67800361 | 0.00687617 |
| rs12001295 | 0.05272256 | 2.21810303 | 0.1478398 | 1.96037745 | 0.00693366 |
| rs2267908 | 0.20262375 | 1.672388773 | 0.07377876 | 1.40092131 | 0.00700235 |
| rs12625871 | 0.01079712 | 0.56080892 | 0.48307066 | 0.54867028 | 0.00702961 |
| rs1058240 | 0.0255244 | 0.501587784 | 0.13892818 | 0.62184082 | 0.00705888 |
| rs9310940 | 0.21046792 | 1.534801231 | 0.19126356 | 1.44173233 | 0.00708699 |
| rs12814009 | 0.04018572 | 0.85737766 | 0.74635877 | 0.60684251 | 0.00714929 |
| rs7559522 | 0.00878969 | 0.653199774 | 0.09010336 | 0.72623812 | 0.00723028 |
| rs1797647 | 0.09192002 | 0.531576091 | 0.06534918 | 0.69479558 | 0.00723465 |
| rs304839 | 0.27377029 | 1.933369668 | 0.04096021 | 1.519783 | 0.00727028 |
| rs10972149 | 0.09827821 | 1.982303974 | 0.16022376 | 1.56393114 | 0.00727045 |
| rs2069933 | 0.07395592 | 1.400276986 | 0.28599342 | 1.4453417 | 0.00729683 |
| rs12969613 | 0.05884827 | 0.498166411 | 0.01389573 | 0.7198681 | 0.00733444 |
| rs2275603 | 0.12468672 | 2.276509243 | 0.04563816 | 1.47070868 | 0.00737309 |
| rs11044141 | 0.05186795 | 1.73278306 | 0.11349463 | 1.53200877 | 0.00737979 |
| rs1007822 | 0.05919215 | 0.498166411 | 0.01389573 | 0.72051256 | 0.00738553 |
| rs7692976 | 0.05480184 | 0.494195549 | 0.03069494 | 0.70892031 | 0.00749125 |
| rs4485556 | 0.00235261 | 1.397902115 | 0.50367932 | 1.61122769 | 0.00753766 |
| rs2231375 | 0.04220739 | 0.668067207 | 0.1778523 | 0.7008452 | 0.00761801 |
| rs2242660 | 0.0150168 | 0.756806298 | 0.38886309 | 0.68903243 | 0.00770852 |
| rs7732671 | 0.11260985 | 1.154819688 | 0.78346793 | 1.75337264 | 0.00774675 |
| rs17834679 | 0.02521038 | 0.916733777 | 0.76653341 | 0.70125031 | 0.00782735 |
| rs2838733 | 0.07614029 | 1.653502779 | 0.11273347 | 1.45987018 | 0.00786573 |
| rs13173943 | 0.00484349 | 0.945514666 | 0.86077528 | 1.45770814 | 0.00791673 |
| rs4462251 | 0.01518388 | 0.889299251 | 0.66882685 | 0.71937813 | 0.00791696 |
| rs2305340 | 0.12689838 | 0.581977508 | 0.16118037 | 0.64965334 | 0.0079501 |
| rs12451415 | 0.12088012 | 0.678411195 | 0.25039759 | 0.66611984 | 0.00796339 |
| rs2595204 | 0.00863162 | 1.533849353 | 0.18832877 | 1.42736818 | 0.00801759 |
| rs6021183 | 0.0045594 | 1.665236661 | 0.2895987 | 1.81521342 | 0.00802275 |
| rs17113227 | NA | 2.030897722 | 0.00673784 | 1.62365628 | 0.00802282 |
| rs11833550 | 0.10781154 | 2.048397433 | 0.0466996 | 1.57886187 | 0.00812332 |
| rs310247 | 0.05844084 | 1.533403149 | 0.30000436 | 1.46685181 | 0.00847391 |
| rs17875513 | 0.00194626 | 4.488678953 | 0.44414345 | 0.16253264 | 0.00851961 |
| rs910682 | NA | 1.53726206 | 0.32267559 | 1.91249249 | 0.0085282 |
| rs4245886 | 0.05011435 | 0.631269558 | 0.09390401 | 0.72659446 | 0.00855999 |
| rs12185980 | 0.13376119 | 0.743468565 | 0.46740879 | 1.68164239 | 0.00856073 |
| rs2255364 | 0.06357989 | 3.675177597 | 3.23E−05 | 1.54643136 | 0.00860527 |
| rs2268890 | NA | 0.626627758 | 0.04208716 | 0.63743958 | 0.008899 |
| rs6058391 | 0.00238366 | 0.66791201 | 0.40088926 | 0.57929283 | 0.00891021 |
| rs7647903 | 0.28448998 | 2.887094074 | 0.0636608 | 1.50351852 | 0.00891595 |
| rs5996577 | 0.02398456 | 0.590279616 | 0.35982347 | 1.60794968 | 0.00894574 |
| rs6580942 | 0.05457562 | 1.982043892 | 0.04062873 | 1.4624003 | 0.00903024 |
| rs241430 | NA | 0.674243811 | 0.16566189 | 0.596453 | 0.00913438 |
| rs706121 | 0.00133522 | 1.614843189 | 0.16429715 | 1.55574268 | 0.00914737 |
| rs2295616 | 0.01231339 | 0.714667913 | 0.29309131 | 0.67793693 | 0.00915385 |

TABLE 3-continued

| | | | | | | |
|---|---|---|---|---|---|---|
| rs6829390 | 0.00857334 | 0.850565336 | 0.8404433 | 2.00404703 | 0.00917152 |
| rs9817149 | 0.15450723 | 2.698708717 | 0.266516 | 2.13900059 | 0.00917463 |
| rs599563 | NA | 0.346839408 | 0.02656012 | 0.43929499 | 0.00918559 |
| rs2238337 | 0.01187583 | 0.812838175 | 0.53897147 | 1.39071444 | 0.00918659 |
| rs3816724 | 0.01510082 | 1.178560299 | 0.71300002 | 1.83253888 | 0.00921881 |
| rs970283 | 0.00445051 | 0.165726534 | 0.03992744 | 0.60917368 | 0.0092717 |
| rs3733236 | 0.06042245 | 2.795477626 | 0.02145048 | 1.77125565 | 0.00929059 |
| rs10854166 | 0.03416572 | 1.756625912 | 0.03368719 | 1.3955462 | 0.00940624 |
| rs6850557 | 0.00404606 | 0.591937798 | 0.08957996 | 0.71197963 | 0.00948749 |
| rs4572808 | 0.0529861 | 1.667940453 | 0.06254176 | 1.34643121 | 0.00956242 |
| rs875258 | NA | 2.171635923 | 0.00343425 | 1.62007531 | 0.00963046 |
| rs1131510 | NA | 0.283691506 | 0.00092772 | 0.45633087 | 0.00968206 |
| rs10497208 | 0.04098183 | 0.451737257 | 0.01743008 | 0.7270181 | 0.00969018 |
| rs10104302 | 0.04726518 | 1.968171333 | 0.07587968 | 1.45910911 | 0.00980005 |
| rs728373 | 0.06462528 | 1.569525638 | 0.16079534 | 1.39945812 | 0.00980031 |
| rs10977434 | 0.01323086 | 1.235721111 | 0.49790003 | 1.42266906 | 0.00987629 |
| rs12039194 | 0.01062906 | 0.49832587 | 0.20360196 | 0.60172257 | 0.0098777 |
| rs2853884 | 0.02966885 | 1.927931615 | 0.04179488 | 1.43572943 | 0.00989768 |
| rs5743740 | 0.22898274 | 1.336018859 | 0.28954961 | 1.52907649 | 0.00994335 |
| rs7359387 | 0.01047756 | 0.840613031 | 0.72747093 | 0.6307871 | 0.00995871 |

TABLE 4

| SNP | Chrom | BP | Region | Gene | HGDS Odds | HGDS P | HIGS Odds |
|---|---|---|---|---|---|---|---|
| rs12368829 | 12 | 93326073 | intron | CCDC41 | 0.40594217 | 0.41620935 | 0.23749353 |
| rs4147385 | 5 | 179610123 | intron | MAPK9 | 3.04945702 | 0.00017896 | 2.46419229 |
| rs11744216 | 5 | 169018841 | intron | DOCK2 | 0.44998628 | 0.20079861 | 0.27989213 |
| rs17535213 | 12 | 42414658 | intron | PUS7L | 1.18874097 | 0.65886311 | 0.49318189 |
| rs10072056 | 5 | 149485499 | intron | PDGFRB | 0.9326251 | 0.81037828 | 0.58186139 |
| rs10054825 | 5 | 75837339 | intron | IQGAP2 | 0.43711187 | 0.0778727 | 0.324665 |
| rs12546235 | 8 | 23018464 | intron | TNFRSF10C | 0.72515962 | 0.4427109 | 0.37576137 |
| rs2071336 | 16 | 11969175 | coding-synonymous | TNFRSF17 | 1.33642895 | 0.61691603 | 0.10982398 |
| rs414634 | 15 | 89157257 | intron | BLM | 2.2016114 | 0.00536501 | 1.76721841 |
| rs17725712 | 5 | 149471001 | intron | CSF1R | 2.69330968 | 0.06546239 | 2.97352599 |
| rs4242389 | 8 | 23028266 | intron | TNFRSF10C | 1.13500187 | 0.77037148 | 0.39817123 |
| rs11773821 | 7 | 157648848 | intron | PTPRN2 | 0.65518824 | 0.19868332 | 0.45675984 |
| rs8005905 | 14 | 101638120 | coding-nonsynonymous | HSP90AA1 | 0.34859364 | 0.06727143 | 0.45357526 |
| rs1863993 | 5 | 169142758 | intron | DOCK2 | 6.33994362 | 0.00606025 | 1.79012818 |
| rs9482888 | 6 | 128855804 | intron | PTPRK | 12.5742158 | 0.00292392 | 0.26952546 |
| rs6476985 | 9 | 5507559 | intron | PDCD1LG2 | 2.00357117 | 0.06524366 | 2.17561674 |
| rs440238 | 9 | 9006071 | intron | PTPRD | 0.26504479 | 0.00016935 | 0.70059683 |
| rs2278324 | 5 | 38917360 | intron | OSMR | 2.63537533 | 0.00743666 | 1.89816183 |
| rs3826392 | 17 | 11863629 | locus-region | MAP2K4 | 0.51063591 | 0.05983922 | 0.64374497 |
| rs12051769 | 17 | 11918677 | intron | MAP2K4 | 0.46994899 | 0.03942236 | 0.64982994 |
| rs1378796 | 3 | 158614482 | coding-nonsynonymous | VEPH1 | 0.75236304 | 0.47587027 | 0.52764493 |
| rs6065417 | 20 | 40432747 | intron | PTPRT | 0.50610715 | 0.12933303 | 0.56971475 |
| rs3845422 | 1 | 179279594 | intron | MR1 | 0.58149946 | 0.10161841 | 0.56363662 |
| rs208250 | 20 | 40849159 | intron | PTPRT | 1.27519572 | 0.3576712 | 1.57736681 |
| rs1884564 | 20 | 1820658 | intron | LOC728018 | 0.78345665 | 0.52653486 | 0.45784275 |
| rs424051 | 9 | 9004740 | intron | PTPRD | 0.25267033 | 0.00014826 | 0.73786157 |
| rs2596606 | 18 | 75263804 | intron | NFATC1 | 2.41198802 | 0.00952767 | 2.02654187 |
| rs9892152 | 17 | 59755697 | intron | PECAM1 | 1.21176807 | 0.43963293 | 1.79832413 |
| rs12325842 | 17 | 11935497 | intron | MAP2K4 | 0.46723502 | 0.0493405 | 0.64627154 |
| rs3815003 | 15 | 89113827 | intron | BLM | 0.64453883 | 0.20681329 | 0.58889226 |
| rs390406 | 19 | 44920811 | locus-region | CLC | 0.70248295 | 0.30742213 | 0.44814554 |
| rs244090 | 20 | 42667504 | intron | PKIG | 1.71556712 | 0.09647363 | 1.86114844 |
| rs1882019 | 12 | 102861797 | intron | HSP90B1 | 0.65623976 | 0.36715836 | 0.54596795 |
| rs2869460 | 4 | 77140838 | locus-region | CXCL9 | 0.5058031 | 0.08717965 | 0.58827213 |
| rs2879057 | 17 | 34143085 | locus-region | PCGF2 | 0.42515295 | 0.02198811 | 0.64069429 |
| rs244076 | 20 | 42686329 | coding-synonymous | ADA | 1.69508583 | 0.10765184 | 1.8756407 |
| rs638251 | 18 | 7786393 | intron | PTPRM | 0.86837964 | 0.60834621 | 0.60830628 |
| rs11952962 | 5 | 75931035 | intron | IQGAP2 | 2.19383552 | 0.01353614 | 1.41785272 |
| rs10074391 | 5 | 149486896 | intron | PDGFRB | 1.49513964 | 0.40643508 | 2.59859713 |
| rs7170919 | 15 | 89115963 | intron | BLM | 0.60343656 | 0.13274345 | 0.61102113 |
| rs11780679 | 8 | 79821131 | intron | IL7 | 0.28969938 | 0.09898674 | 0.53730499 |
| rs4077341 | 8 | 23018293 | intron | TNFRSF10C | 0.76205039 | 0.33129864 | 0.63450801 |
| rs12001295 | 9 | 5508260 | intron | PDCD1LG2 | 2.23381373 | 0.12694632 | 1.95909625 |
| rs1003854 | 21 | 44534535 | intron | AIRE | 0.67130473 | 0.23146056 | 0.61640983 |
| rs246392 | 5 | 149477865 | intron | PDGFRB | 1.38464673 | 0.28154335 | 0.56867017 |
| rs7690305 | 4 | 15575064 | — | — | 0.67630525 | 0.27238321 | 0.57017516 |
| rs17652304 | 5 | 75912949 | intron | IQGAP2 | 6.53946184 | 0.0017172 | 1.64105085 |
| rs9313487 | 5 | 169394879 | intron | DOCK2 | 0.64895553 | 0.54042356 | 0.43957631 |
| rs1457238 | 2 | 160693708 | intron | ITGB6 | 1.09178513 | 0.75352212 | 0.72059793 |
| rs12692566 | 2 | 160384673 | coding-nonsynonymous | LY75 | 1.77178098 | 0.0875946 | 2.19460251 |
| rs3797390 | 5 | 75942821 | intron | IQGAP2 | 2.57357265 | 0.00174144 | 1.20099738 |
| rs2070783 | 17 | 59760703 | intron | PECAM1 | 1.16581079 | 0.54097307 | 1.75467319 |

TABLE 4-continued

| | | | | | | | |
|---|---|---|---|---|---|---|---|
| rs1264456 | 6 | 30570063 | — | — | 0.6311328 | 0.09292498 | 0.6298167 |
| rs1075846 | 5 | 149484351 | intron | PDGFRB | 0.84122055 | 0.54316742 | 0.6804459 |
| rs6093584 | 20 | 40237760 | intron | PTPRT | 0.51129422 | 0.0273209 | 0.75714002 |
| rs13173943 | 5 | 35037762 | intron | AGXT2 | 1.53186639 | 0.11764271 | 1.76018633 |
| rs10797666 | 1 | 179285422 | intron | MR1 | 0.67279722 | 0.2032679 | 0.58684061 |
| rs4724231 | 7 | 43608739 | intron | STK17A | 0.88797357 | 0.74583064 | 0.37564254 |
| rs613613 | 9 | 9004274 | intron | PTPRD | 0.1428006 | 2.54E−05 | 0.83677802 |
| rs6742576 | 2 | 239852569 | intron | HDAC4 | 2.18359035 | 0.0518853 | 1.55889951 |
| rs927335 | 11 | 35207094 | intron | CD44 | 1.47588642 | 0.17083319 | 1.62199792 |
| rs1638006 | 7 | 157177926 | intron | PTPRN2 | 0.73782139 | 0.34403344 | 0.62866877 |
| rs12959952 | 18 | 46494835 | intron | MAPK4 | 0.7036857 | 0.19973021 | 0.68642326 |
| rs10497208 | 2 | 160695167 | intron | ITGB6 | 1.09178513 | 0.75352212 | 0.73334585 |
| rs496888 | 1 | 12155393 | intron | TNFRSF1B | 0.98849714 | 0.96835223 | 0.58209238 |
| rs246394 | 5 | 149478344 | intron | PDGFRB | 1.07800003 | 0.8049839 | 0.63067265 |
| rs3736395 | 5 | 75924224 | intron | IQGAP2 | 2.26291757 | 0.01047821 | 1.38697287 |
| rs1573706 | 20 | 40354563 | intron | PTPRT | 1.49949889 | 0.19631716 | 1.6069948 |
| rs17763453 | 17 | 3664884 | intron | C17orf85 | 1.84921458 | 0.0363718 | 1.89696314 |
| rs1050382 | 17 | 59753732 | locus-region | PECAM1 | 1.20359468 | 0.46433271 | 1.74401131 |
| rs161042 | 5 | 146166067 | intron | PPP2R2B | 1.3106124 | 0.45765546 | 0.38138725 |
| rs1105238 | 1 | 159948285 | intron | FCRLA | 1.75481239 | 0.04261883 | 1.35815008 |
| rs11032349 | 11 | 33686248 | mrna-utr | CD59 | 0.42542725 | 0.07218081 | 0.55987429 |
| rs7641625 | 3 | 37642638 | intron | ITGA9 | 1.47989139 | 0.19643664 | 1.63849578 |
| rs3733678 | 5 | 149491985 | intron | PDGFRB | 1.75835283 | 0.22087157 | 2.06780589 |
| rs13172280 | 5 | 35063668 | intron | AGXT2 | 1.38945614 | 0.21352732 | 1.73502557 |
| rs7246376 | 19 | 8109328 | coding-nonsynonymous | FBN3 | 1.47283872 | 0.22675894 | 1.68780469 |
| rs704697 | 11 | 33681356 | mrna-utr | CD59 | 0.81783308 | 0.4595754 | 0.64014021 |
| rs2283539 | 16 | 24036462 | intron | PRKCB1 | 1.42703837 | 0.20435086 | 1.67553526 |
| rs926479 | 20 | 40786436 | intron | PTPRT | 0.85658553 | 0.82748284 | 2.59667403 |
| rs12969613 | 18 | 65710412 | intron | CD226 | 0.79877362 | 0.40429658 | 0.73759216 |
| rs1007822 | 18 | 65706201 | intron | CD226 | 0.79877362 | 0.40429658 | 0.73861498 |
| rs161021 | 5 | 146189300 | intron | PPP2R2B | 1.40187743 | 0.35609199 | 0.36047838 |
| rs832517 | 12 | 93164318 | intron | PLXNC1 | 0.69066171 | 0.1907413 | 0.68112858 |
| rs4955104 | 3 | 30696707 | intron | TGFBR2 | 1.79111758 | 0.0867806 | 1.70995826 |
| rs6214 | 12 | 101317699 | mrna-utr | IGF1 | 1.71901496 | 0.04522154 | 1.61292084 |
| rs910682 | 6 | 112282428 | intron | FYN | 2.5624024 | 0.00382559 | Inf |
| rs7072398 | 10 | 6119852 | intron | IL2RA | 1.04244072 | 0.87305095 | 0.57726445 |
| rs3828016 | 20 | 1865290 | intron | SIRPA | 0.50163574 | 0.01962402 | 0.70944458 |
| rs13206518 | 6 | 6098001 | intron | F13A1 | 0.80015969 | 0.688464 | 0.47126387 |
| rs976881 | 1 | 12156341 | intron | TNFRSF1B | 1.41934278 | 0.21707063 | 1.75339747 |
| rs17201075 | 5 | 41221364 | intron | C6 | 1.09771229 | 0.86532931 | 3.71934504 |
| rs1436522 | 4 | 87183196 | intron | MAPK10 | 0.89211758 | 0.75710477 | 0.61156718 |
| rs7130876 | 11 | 48007571 | intron | PTPRJ | 1.54556632 | 0.15881083 | 0.52537558 |
| rs6021183 | 20 | 49455556 | intron | NFATC2 | 1.44353751 | 0.29803193 | 2.90323676 |
| rs6837303 | 4 | 111189034 | locus-region | ELOVL6 | 0.64314341 | 0.1435302 | 0.69472635 |
| rs4798598 | 18 | 7805873 | intron | PTPRM | 0.65847522 | 0.12886739 | 0.69046153 |
| rs7732671 | 5 | 149192436 | coding-nonsynonymous | PPARGC1B | 3.20354454 | 0.00589543 | 1.55843339 |
| rs805274 | 6 | 31773173 | intron | BAT5 | 0.55014299 | 0.06535639 | 0.62947384 |
| rs6769530 | 3 | 158512216 | intron | VEPH1 | 1.03295124 | 0.92248422 | 0.54286612 |
| rs1519602 | 2 | 196736037 | intron | STK17B | 0.55320744 | 0.03324443 | 0.73904041 |
| rs7559522 | 2 | 45903540 | intron | PRKCE | 1.04566366 | 0.85817157 | 0.65154256 |
| rs2575674 | 4 | 87156570 | locus-region | MAPK10 | 1.10853608 | 0.74215687 | 0.58503629 |
| rs244091 | 20 | 42664524 | intron | PKIG | 1.80520247 | 0.09789911 | 1.75887237 |
| rs11265416 | 1 | 158738437 | intron | SLAMF6 | 2.35933243 | 0.37113726 | 0.21061583 |
| rs7987079 | 13 | 23106829 | intron | TNFRSF19 | 1.40983092 | 0.34867691 | 2.88724265 |
| rs1797647 | 12 | 12143345 | mrna-utr | BCL2L14 | 0.71062358 | 0.26179611 | 0.74897192 |
| rs12034383 | 1 | 205870218 | intron | CR1 | 1.23123613 | 0.39538637 | 1.48956715 |
| rs169142 | 16 | 24039431 | intron | PRKCB1 | 0.64831743 | 0.08571383 | 0.71324157 |
| rs2296449 | 1 | 117380273 | intron | IGSF2 | 0.29276129 | 0.25225893 | 0.47588685 |
| rs793816 | 4 | 185591486 | intron | IRF2 | 0.40984979 | 0.42558509 | 0.23730079 |
| rs246395 | 5 | 149479865 | coding-synonymous | PDGFRB | 1.38582698 | 0.27133701 | 0.6194716 |
| rs246390 | 5 | 149476514 | intron | PDGFRB | 0.7247334 | 0.2684215 | 0.72046124 |
| rs4955272 | 3 | 32288680 | intron | CMTM8 | 0.96089791 | 0.9051644 | 0.60948044 |
| rs6060855 | 20 | 29762606 | intron | BCL2L1 | 0.895837 | 0.81688231 | 0.43117643 |
| rs9831803 | 3 | 191844191 | intron | IL1RAP | 1.34971585 | 0.38907767 | 1.59107034 |
| rs12506181 | 4 | 15576875 | — | — | 0.74922786 | 0.35551237 | 0.6513769 |
| rs4245886 | 3 | 32279107 | intron | CMTM8 | 0.75313095 | 0.34382198 | 0.73876461 |
| rs244656 | 5 | 133477726 | locus-region | TCF7 | 1.06335655 | 0.86197643 | 0.48971131 |
| rs9817149 | 3 | 191740949 | intron | IL1RAP | 2.85058652 | 0.02464441 | 1.86248097 |
| rs4472605 | 9 | 34556190 | intron | CNTFR | 1.79149362 | 0.12460998 | 1.45596316 |
| rs2595204 | 2 | 46047369 | intron | PRKCE | 1.09030672 | 0.76799091 | 1.57921594 |
| rs17317153 | 20 | 40380498 | intron | PTPRT | 1.32934137 | 0.42616821 | 2.63656846 |
| rs4572808 | 3 | 32292718 | intron | CMTM8 | 1.31637632 | 0.32982957 | 1.32095634 |
| rs2287768 | 5 | 147471725 | intron | SPINK5 | 0.84607856 | 0.59736723 | 0.63187513 |
| rs2227562 | 10 | 75342967 | intron | PLAU | 0.94723133 | 0.87839576 | 0.60790359 |
| rs4094864 | 18 | 65696478 | intron | CD226 | 0.88291236 | 0.63844854 | 0.71121514 |
| rs831603 | 11 | 33715214 | — | — | 0.74543407 | 0.29031682 | 0.69047971 |
| rs6850557 | 4 | 111130464 | intron | EGF | 1.28335256 | 0.38183122 | 0.61087182 |
| rs6863088 | 5 | 179612366 | intron | MAPK9 | 0.664833 | 0.14196536 | 0.48692773 |
| rs10041067 | 1 | 158723751 | intron | SLAMF6 | 2.2184953 | 0.01398437 | 0.43080195 |
| rs17141840 | 6 | 6118369 | intron | F13A1 | 2.07470652 | 0.08885017 | 1.95408011 |

TABLE 4-continued

| | | | | | | | |
|---|---|---|---|---|---|---|---|
| rs10406354 | 19 | 59022044 | — | — | 0.89952742 | 0.77565299 | 0.52404025 |
| rs6065460 | 20 | 40363108 | intron | PTPRT | 0.42123728 | 0.0634589 | 0.65721731 |
| rs12667537 | 7 | 157343101 | intron | PTPRN2 | 0.59305484 | 0.08714542 | 0.70517477 |
| rs17811425 | 20 | 40856507 | intron | PTPRT | 1.33148163 | 0.28994099 | 1.54496509 |
| rs2302267 | 23 | 12795499 | intron | TLR7 | 1.81654223 | 0.03143813 | 1.4130263 |
| rs4820059 | 22 | 30676468 | intron | YWHAH | 0.81528639 | 0.47453164 | 1.72048152 |
| rs6621980 | 23 | 104690227 | intron | IL1RAPL2 | 1.28882708 | 0.18109236 | 1.3068943 |
| rs1007212 | 15 | 97101441 | intron | IGF1R | 1.55869313 | 0.09640159 | 1.27530638 |
| rs866484 | 1 | 157253101 | coding-nonsynonymous | IFI16 | 1.22252083 | 0.52829257 | 1.56924172 |
| rs3181096 | 2 | 204278337 | locus-region | CD28 | 1.36261441 | 0.27972083 | 1.37728226 |
| rs2302759 | 16 | 49385102 | intron | CYLD | 0.33689733 | 0.01461099 | 0.71273483 |
| rs2275603 | 1 | 159948404 | coding-nonsynonymous | FCRLA | 1.64949637 | 0.07041442 | 1.33588972 |
| rs5996577 | 22 | 22251427 | intron | IGLL1 | 2.1220002 | 0.02489912 | 1.72345433 |
| rs2076846 | 10 | 6103259 | intron | IL2RA | 1.13945745 | 0.63633591 | 0.59088718 |
| rs4639174 | 5 | 179602877 | intron | MAPK9 | 1.42452019 | 0.30825037 | 2.34009523 |
| rs17834679 | 19 | 56961899 | intron | FPRL1 | 0.64573737 | 0.1415216 | 0.67581905 |
| rs3024486 | 6 | 6090408 | mrna-utr | F13A1 | 1.9586438 | 0.27132607 | 8.87599881 |
| rs2279590 | 8 | 27512170 | intron | CLU | 0.92228597 | 0.76719657 | 1.75040285 |
| rs9867325 | 3 | 138101599 | intron | NCK1 | 1.62323973 | 0.10735731 | 1.51983072 |
| rs2010452 | 3 | 37741319 | intron | ITGA9 | 1.46806911 | 0.17169416 | 1.54025474 |
| rs12451415 | 17 | 11947505 | intron | MAP2K4 | 0.30015344 | 0.00896293 | 0.74534992 |
| rs4253655 | 22 | 44947835 | intron | PPARA | 2.32421494 | 0.01612296 | 1.54643399 |
| rs6058391 | 20 | 29743569 | intron | BCL2L1 | 0.96518672 | 0.94244112 | 0.44238887 |
| rs7692976 | 4 | 111131016 | intron | EGF | 0.85015165 | 0.54038359 | 0.72312756 |
| rs6482644 | 10 | 129715311 | intron | PTPRE | 0.72051209 | 0.23151259 | 0.76981675 |
| rs9426315 | 1 | 29497962 | intron | PTPRU | 2.25036285 | 0.00453832 | 1.3875101 |
| rs2286414 | 7 | 157167781 | intron | PTPRN2 | 3.20084147 | 0.02222804 | 3.78156695 |
| rs6544865 | 2 | 46044534 | intron | PRKCE | 1.27313525 | 0.40339922 | 1.76038942 |
| rs1984399 | 20 | 40312545 | intron | PTPRT | 1.38508533 | 0.20837745 | 1.46992979 |
| rs1838065 | 10 | 54199263 | intron | MBL2 | 1.34748907 | 0.24834257 | 1.46857224 |
| rs11214108 | 11 | 111548824 | locus-region | TEX12 | 1.56594405 | 0.23747814 | 2.23726449 |
| rs717176 | 4 | 15604412 | intron | PROM1 | 0.73755539 | 0.24483727 | 0.68663689 |
| rs1797646 | 12 | 12143028 | intron | BCL2L14 | 0.76049374 | 0.36369491 | 0.76117236 |
| rs2238337 | 15 | 89156736 | intron | BLM | 1.7414468 | 0.03857242 | 1.50742576 |
| rs763361 | 18 | 65682622 | coding-nonsynonymous | CD226 | 1.07002722 | 0.79641874 | 1.45817642 |
| rs4027402 | 14 | 63566502 | coding-nonsynonymous | SYNE2 | 0.29027382 | 0.01182678 | 0.76414481 |
| rs970283 | 20 | 40713729 | intron | PTPRT | 1.39292381 | 0.49302644 | 0.54068963 |
| rs4953292 | 2 | 46045487 | intron | PRKCE | 0.61471861 | 0.06917241 | 0.71271184 |
| rs7541717 | 1 | 71179181 | intron | PTGER3 | 0.82329266 | 0.52082934 | 0.55588639 |
| rs1523474 | 3 | 188942191 | intron | BCL6 | 0.54023628 | 0.03951804 | 0.80092435 |
| rs4902264 | 14 | 63561448 | coding-nonsynonymous | SYNE2 | 0.31358432 | 0.01315874 | 1.91932441 |
| rs210431 | 23 | 104831589 | intron | IL1RAPL2 | 1.23663717 | 0.26019742 | 1.25792622 |
| rs6780432 | 3 | 106985186 | intron | CBLB | 0.49699735 | 0.09690156 | 0.64739941 |
| rs1058240 | 10 | 8156604 | mrna-utr | GATA3 | 0.81437984 | 0.57424039 | 0.60486059 |
| rs2305340 | 12 | 7157242 | — | — | 0.45089796 | 0.05819758 | 0.73801084 |
| rs6751287 | 2 | 46134145 | intron | PRKCE | 1.10034772 | 0.70820629 | 0.55127786 |
| rs12881815 | 14 | 63674348 | coding-nonsynonymous | SYNE2 | 4.93816542 | 0.00874223 | 3.27810424 |
| rs9991904 | 4 | 111142028 | intron | EGF | 1.17849809 | 0.5691142 | 0.60057077 |
| rs509749 | 1 | 159060184 | coding-nonsynonymous | LY9 | 1.66696778 | 0.05648367 | 1.38107099 |
| rs1044141 | 7 | 43630805 | coding-nonsynonymous | STK17A | 1.35120379 | 0.34792227 | 1.54280229 |
| rs878081 | 21 | 44532705 | coding-synonymous | AIRE | 0.70507698 | 0.2927785 | 0.66315301 |
| rs2227827 | 5 | 76054800 | intron | F2R | 1.51074004 | 0.49237438 | 2.20757565 |
| rs11574113 | 12 | 46525167 | intron | VDR | 0.07642322 | 0.01288301 | 2.46E-161 |
| rs17110948 | 5 | 149498698 | intron | PDGFRB | 0.76392252 | 0.61226492 | 0.49768788 |
| rs1865462 | 7 | 157330723 | intron | PTPRN2 | 3.69492819 | 0.00687723 | 1.76884429 |
| rs1552323 | 20 | 3398811 | locus-region | ATRN | 1.34848656 | 0.39325823 | 1.84726427 |
| rs872081 | 6 | 356064 | mrna-utr | IRF4 | 0.59007603 | 0.05289113 | 0.68154856 |
| rs11852361 | 15 | 89127103 | coding-nonsynonymous | BLM | 0.37852792 | 0.15612895 | 0.55754201 |
| rs2288522 | 19 | 60400287 | intron | PTPRH | 1.67691064 | 0.16037886 | 1.65957717 |
| rs10854166 | 19 | 18513844 | intron | FKBP8 | 1.06807784 | 0.8007258 | 1.47150955 |
| rs17419586 | 13 | 23148712 | locus-region | TNFRSF19 | 0.97848495 | 0.93879471 | 1.8778521 |
| rs8078439 | 17 | 11983357 | intron | MAP2K4 | 1.8771038 | 0.02841666 | 1.51384634 |
| rs2569190 | 5 | 139993100 | intron | CD14 | 1.39020846 | 0.216763 | 1.59274474 |
| rs17748322 | 5 | 75911385 | intron | IQGAP2 | 2.2993276 | 0.00733668 | 1.14298838 |
| rs17228097 | 3 | 37502408 | intron | ITGA9 | 1.58216805 | 0.19915925 | 1.37147549 |
| rs10104302 | 8 | 57030794 | intron | LYN | 1.36776903 | 0.32678276 | 1.44246121 |
| rs17283264 | 3 | 46228570 | — | — | 1.85735919 | 0.10142812 | 6.6280982 |
| rs1062069 | 5 | 149412806 | locus-region | CSF1R | 1.23466277 | 0.57989157 | 1.92846985 |
| rs1724120 | 2 | 96173058 | mrna-utr | DUSP2 | 0.78255986 | 0.32792438 | 0.72325427 |
| rs7647903 | 3 | 3108791 | intron | IL5RA | 2.13450415 | 0.01128258 | 1.23815585 |
| rs11237451 | 11 | 77703107 | intron | GAB2 | 0.65565062 | 0.20267608 | 0.73454025 |
| rs10165797 | 2 | 113544921 | intron | IL1F10 | 1.49689483 | 0.11969393 | 1.39321058 |
| rs1206486 | 7 | 121339630 | intron | PTPRZ1 | 1.34572269 | 0.26382119 | 1.49333138 |
| rs706121 | 9 | 33250632 | intron | BAG1 | 0.90288507 | 0.75541553 | 2.22530992 |
| rs13042473 | 20 | 40843315 | intron | PTPRT | 0.59954867 | 0.16519214 | 0.7743799 |
| rs3024498 | 1 | 205008152 | mrna-utr | IL10 | 0.75456541 | 0.37841053 | 0.71982913 |
| rs7289754 | 22 | 20926259 | — | — | 1.98404501 | 0.01102149 | 1.08058008 |
| rs11168267 | 12 | 46537809 | intron | VDR | 0.29285052 | 0.05042848 | 0.01236529 |

TABLE 4-continued

| | | | | | | | |
|---|---|---|---|---|---|---|---|
| rs1918309 | 12 | 93220659 | intron | | PLXNC1 | 1.03323499 | 0.91214827 | 1.51539468 |
| rs17671456 | 8 | 22441022 | intron | | PPP3CC | 1.61060959 | 0.21643286 | 1.60308204 |

| SNP | HIGS P | MIBS Odds | MIBS P | Meta Odds | Meta P |
|---|---|---|---|---|---|
| rs12368829 | 1.55E−07 | 0.970246771 | 0.98476165 | 0.25439022 | 1.81E−07 |
| rs4147385 | 0.00046696 | 1.162263286 | 0.77330466 | 2.43554195 | 1.08E−06 |
| rs11744216 | 1.44E−05 | 0.467690712 | 0.3787925 | 0.31650564 | 5.86E−06 |
| rs17535213 | 4.45E−06 | 0.348814754 | 0.07743061 | 0.54098429 | 1.04E−05 |
| rs10072056 | 0.00074227 | 0.311502349 | 0.00011672 | 0.57029367 | 1.05E−05 |
| rs10054825 | 0.0001897 | 0.419079017 | 0.10365859 | 0.36525145 | 1.10E−05 |
| rs12546235 | 9.63E−06 | 0.57082165 | 0.51527316 | 0.43960107 | 1.64E−05 |
| rs2071336 | 5.19E−07 | 0.24524377 | 0.24041836 | 0.27143985 | 0.00010608 |
| rs414634 | 0.00177128 | 1.017530583 | 0.962581 | 1.72218627 | 0.00012352 |
| rs17725712 | 0.01195522 | 3.389006725 | 0.02382404 | 2.99952628 | 0.00012428 |
| rs4242389 | 8.81E−06 | 0.829766359 | 0.80181693 | 0.4994584 | 0.00012879 |
| rs11773821 | 0.0008452 | 0.468699994 | 0.10133446 | 0.50872671 | 0.00012997 |
| rs8005905 | 0.0003978 | 0.801770808 | 0.6502241 | 0.48106483 | 0.00013186 |
| rs1863993 | 0.44319157 | 5.580935156 | 0.00469048 | 4.32777987 | 0.00015861 |
| rs9482888 | NA | 8.839576621 | 0.0222156 | 10.7547944 | 0.00018212 |
| rs6476985 | 0.00536715 | 2.134496929 | 0.14605717 | 2.11637663 | 0.00027521 |
| rs440238 | 0.04195541 | 0.689246147 | 0.33766473 | 0.59283279 | 0.00032172 |
| rs2278324 | 0.00282462 | 0.758631103 | 0.61958397 | 1.87163184 | 0.00034725 |
| rs3826392 | 0.0084676 | 0.569023823 | 0.11903429 | 0.60997937 | 0.00040366 |
| rs12051769 | 0.00843671 | 0.602562032 | 0.18071893 | 0.61396868 | 0.00044857 |
| rs1378796 | 0.00049546 | 0.777886845 | 0.5515047 | 0.58667166 | 0.00058411 |
| rs6065467 | 0.00162751 | 0.844491824 | 0.77908431 | 0.57700459 | 0.00058673 |
| rs3845422 | 0.00278781 | 0.765244738 | 0.52768076 | 0.59103311 | 0.00066496 |
| rs208250 | 0.00614501 | 2.310452806 | 0.03015281 | 1.5640073 | 0.00072107 |
| rs1884564 | 0.00016232 | 1.228896815 | 0.73117837 | 0.55576556 | 0.00076519 |
| rs424051 | 0.08378924 | 0.672961838 | 0.30855376 | 0.61133786 | 0.00078465 |
| rs2596606 | 0.00317447 | 0.789526971 | 0.58332157 | 1.80948675 | 0.00087248 |
| rs9892152 | 0.00076293 | 1.389910702 | 0.35012917 | 1.55068941 | 0.00091287 |
| rs12325842 | 0.01057338 | 0.655448359 | 0.2862399 | 0.61855994 | 0.00094923 |
| rs3815003 | 0.00175443 | 0.837715833 | 0.65555139 | 0.6254446 | 0.0009581 |
| rs390406 | 0.00011495 | 1.409500379 | 0.45543429 | 0.57751687 | 0.00096039 |
| rs244090 | 0.00918138 | 1.655049937 | 0.25153827 | 1.78317553 | 0.00102069 |
| rs1882019 | 0.00575273 | 0.413630679 | 0.09587792 | 0.5432514 | 0.00102399 |
| rs2869460 | 0.0026252 | 0.915575879 | 0.81620158 | 0.6164075 | 0.00111423 |
| rs2879097 | 0.00665552 | 0.974927042 | 0.95356449 | 0.63128529 | 0.00119921 |
| rs244076 | 0.01007464 | 1.655049937 | 0.25153827 | 1.78255866 | 0.0012403 |
| rs638251 | 0.00136003 | 0.665759136 | 0.27986195 | 0.66313286 | 0.00124552 |
| rs11952962 | 0.14102305 | 2.654850747 | 0.04039954 | 1.76802039 | 0.0012525 |
| rs10074391 | 0.01865724 | 4.556804728 | 0.01222177 | 2.44009991 | 0.00126698 |
| rs7170919 | 0.00547374 | 0.734226073 | 0.4768709 | 0.62260685 | 0.00131742 |
| rs11780679 | 0.02719962 | 0.325285615 | 0.05263728 | 0.46297251 | 0.00132003 |
| rs4077341 | 0.00519201 | 0.507287168 | 0.13900396 | 0.64934295 | 0.00132538 |
| rs12001295 | 0.05272256 | 3.889310136 | 0.02232057 | 2.30783236 | 0.00132646 |
| rs1003854 | 0.00808487 | 0.567523116 | 0.16242701 | 0.62006744 | 0.00133582 |
| rs246392 | 0.00056846 | 0.462869036 | 0.02356977 | 0.6541726 | 0.00137337 |
| rs7690305 | 0.00290621 | 0.712582883 | 0.53237079 | 0.60144396 | 0.0014244 |
| rs17652304 | 0.49335132 | 4.730242662 | 0.15371941 | 3.86360763 | 0.00146254 |
| rs9313487 | 0.0034416 | 0.208542205 | 0.17217507 | 0.44575207 | 0.00150463 |
| rs1457238 | 0.03083353 | 0.229441733 | 2.44E−05 | 0.67624734 | 0.00168974 |
| rs12692566 | 0.00193067 | 0.81400343 | 0.69542463 | 1.80458897 | 0.00175191 |
| rs3797390 | 0.35032961 | 2.263995603 | 0.03447804 | 1.60293238 | 0.00182055 |
| rs2070783 | 0.00171067 | 1.439750782 | 0.2761811 | 1.51376522 | 0.00193313 |
| rs1264456 | 0.00245695 | 1.371604918 | 0.46320706 | 0.67448283 | 0.00199097 |
| rs1075846 | 0.01175816 | 0.502892078 | 0.0409032 | 0.67989373 | 0.00201972 |
| rs6093584 | 0.1173883 | 0.475557176 | 0.03914729 | 0.64778754 | 0.00209511 |
| rs13173943 | 0.00484349 | 1.135520315 | 0.74066077 | 1.58085124 | 0.00210867 |
| rs10797666 | 0.00330048 | 0.881837867 | 0.75079711 | 0.63897389 | 0.00211897 |
| rs4724231 | 0.00020324 | 1.144452734 | 0.87410985 | 0.52878863 | 0.00213939 |
| rs613613 | 0.33851924 | 0.43635212 | 0.04151254 | 0.61461746 | 0.00219926 |
| rs6742576 | 0.06345516 | 1.95184538 | 0.09706741 | 1.75133997 | 0.00220974 |
| rs927335 | 0.01410875 | 1.631801224 | 0.21485661 | 1.5813765 | 0.00222182 |
| rs1638006 | 0.00560578 | 0.672815037 | 0.33341949 | 0.65310735 | 0.00228823 |
| rs12959952 | 0.05307649 | 0.496605859 | 0.0291322 | 0.64845801 | 0.00231721 |
| rs10497208 | 0.04098183 | 0.229441733 | 2.44E−05 | 0.68428905 | 0.00232585 |
| rs496888 | 0.00079136 | 0.72936899 | 0.45979949 | 0.66556634 | 0.0023772 |
| rs246394 | 0.00452891 | 0.44036657 | 0.02617432 | 0.66714381 | 0.00243689 |
| rs3736395 | 0.17646102 | 2.065974332 | 0.11569786 | 1.71358192 | 0.00246551 |
| rs1573706 | 0.04833766 | 2.213076945 | 0.03878119 | 1.67701827 | 0.00247535 |
| rs17763453 | 0.01033902 | 1.041064199 | 0.91761157 | 1.67503165 | 0.00254263 |
| rs1050382 | 0.00167956 | 1.245746436 | 0.55031664 | 1.50011877 | 0.00265991 |
| rs161042 | 2.05E−05 | 0.916673345 | 0.82584783 | 0.59559565 | 0.00272184 |
| rs1105238 | 0.10163662 | 2.459090844 | 0.04842032 | 1.5518509 | 0.00275769 |
| rs11032349 | 0.03097707 | 0.570364102 | 0.24618281 | 0.5323338 | 0.00276883 |
| rs7641625 | 0.02261696 | 1.701486593 | 0.13973038 | 1.605386 | 0.0027894 |
| rs3733678 | 0.02996296 | 2.914679958 | 0.0752997 | 2.09141994 | 0.00281082 |

TABLE 4-continued

| | | | | | |
|---|---|---|---|---|---|
| rs13172280 | 0.0036724 | 1.135520315 | 0.74066077 | 1.53297046 | 0.00281937 |
| rs7246376 | 0.01577555 | 2.116813201 | 0.16148837 | 1.66167608 | 0.00285523 |
| rs704697 | 0.01375692 | 0.467296279 | 0.05636814 | 0.65732858 | 0.00291847 |
| rs2283539 | 0.01026196 | 1.431999362 | 0.34269455 | 1.56120614 | 0.00297676 |
| rs926479 | 0.07353594 | 9.982484611 | 0.00055812 | 2.89090119 | 0.00312637 |
| rs12969613 | 0.05884827 | 0.37050971 | 0.00440838 | 0.68401986 | 0.00312925 |
| rs1007822 | 0.05919215 | 0.37050971 | 0.00440838 | 0.68483547 | 0.00316234 |
| rs161021 | 7.72E−06 | 1.075853393 | 0.86384871 | 0.59542387 | 0.00326861 |
| rs832517 | 0.01733639 | 0.642026655 | 0.25481129 | 0.67856609 | 0.00327793 |
| rs4955104 | 0.01159083 | 1.184086117 | 0.63734029 | 1.60426941 | 0.00333424 |
| rs6214 | 0.0038546 | 0.629670784 | 0.25015386 | 1.477545 | 0.00337387 |
| rs910682 | NA | 1.614806551 | 0.38991522 | 2.2787084 | 0.00337616 |
| rs7072398 | 0.00039605 | 0.856265088 | 0.66109688 | 0.69435573 | 0.00343648 |
| rs3828016 | 0.04488799 | 0.800559925 | 0.50519681 | 0.67294756 | 0.00343895 |
| rs13206518 | 0.02930569 | 0.089255123 | 0.00339299 | 0.44557584 | 0.0034403 |
| rs976881 | 0.00253158 | 0.932227215 | 0.86130551 | 1.52797732 | 0.00346769 |
| rs17201075 | 0.00846313 | 3.329956454 | 0.03022541 | 2.45381211 | 0.00351449 |
| rs1436522 | 0.00435674 | 0.707613566 | 0.27826946 | 0.66436007 | 0.00356592 |
| rs7130876 | 0.00026877 | 0.357821168 | 0.05226772 | 0.65169287 | 0.0036519 |
| rs6021183 | 0.0045594 | 1.925732512 | 0.28176322 | 1.99075048 | 0.00365776 |
| rs6837303 | 0.03179239 | 0.626696378 | 0.1909250 | 0.67359438 | 0.00383111 |
| rs4798598 | 0.01799934 | 0.76514178 | 0.467531 | 0.69192431 | 0.00391466 |
| rs7732671 | 0.11260985 | 1.478295674 | 0.55400167 | 1.88287184 | 0.00401273 |
| rs805274 | 0.01306354 | 1.032014723 | 0.94369336 | 0.64720367 | 0.00420173 |
| rs6769530 | 0.00098157 | 0.777886845 | 0.5515047 | 0.64910947 | 0.00426287 |
| rs1519602 | 0.08236304 | 0.633695267 | 0.233687 | 0.67483508 | 0.00428548 |
| rs7559522 | 0.00878969 | 0.509902099 | 0.02321788 | 0.70158138 | 0.00433721 |
| rs2575674 | 0.00106201 | 0.755301384 | 0.40959324 | 0.683401 | 0.00434884 |
| rs244091 | 0.0259514 | 1.412033578 | 0.42259279 | 1.69990307 | 0.0044037 |
| rs11265416 | NA | 12.09770863 | 0.00276237 | 5.99409961 | 0.00441809 |
| rs7987909 | 0.00560456 | 1.819176447 | 0.23779462 | 1.9493235 | 0.00444665 |
| rs1797647 | 0.09192002 | 0.337476773 | 0.00654404 | 0.67165266 | 0.00445714 |
| rs12034383 | 0.02330856 | 2.203360165 | 0.05468089 | 1.46637086 | 0.00452342 |
| rs169142 | 0.0696807 | 0.605725581 | 0.154871 | 0.67605094 | 0.00452569 |
| rs2296449 | 0.05303457 | 0.214111262 | 0.04714885 | 0.39451609 | 0.00452998 |
| rs793816 | 0.00578488 | 18643042927 | NA | 0.26156534 | 0.00453749 |
| rs246395 | 0.00236794 | 0.458094524 | 0.02696439 | 0.69338691 | 0.00467196 |
| rs246390 | 0.07735733 | 0.569077489 | 0.04039748 | 0.6809586 | 0.00472586 |
| rs4955272 | 0.00517256 | 0.569607579 | 0.18861383 | 0.66011681 | 0.00472636 |
| rs6060855 | 0.00181195 | 0.732955751 | 0.60068371 | 0.54040786 | 0.00477793 |
| rs9831803 | 0.07946045 | 3.921246215 | 0.00655085 | 1.72989626 | 0.00480705 |
| rs12506181 | 0.02247829 | 0.57107144 | 0.13832885 | 0.65874323 | 0.00482864 |
| rs4245886 | 0.05011435 | 0.469457936 | 0.030224 | 0.69761017 | 0.00483857 |
| rs244656 | 0.00097469 | 0.669055839 | 0.45543166 | 0.61156058 | 0.00486188 |
| rs9817149 | 0.15450723 | 4.730951503 | 0.20808618 | 2.37904215 | 0.00498185 |
| rs4472605 | 0.05529258 | 2.135278739 | 0.11254484 | 1.58260036 | 0.00502758 |
| rs2595204 | 0.00863162 | 1.64977881 | 0.14002211 | 1.46701047 | 0.00511685 |
| rs17317153 | 0.00486086 | 1.800676856 | 0.27972342 | 1.88000109 | 0.00516092 |
| rs4572808 | 0.0529861 | 2.310419141 | 0.02300502 | 1.40224352 | 0.00521911 |
| rs2287768 | 0.02210027 | 0.504992842 | 0.06324674 | 0.65098707 | 0.00527658 |
| rs2227562 | 0.02243608 | 0.39689553 | 0.02268151 | 0.62441721 | 0.00528067 |
| rs4094864 | 0.03842952 | 0.409810295 | 0.01211854 | 0.69595111 | 0.0053456 |
| rs831603 | 0.03075735 | 0.551646182 | 0.12308197 | 0.6838719 | 0.00536337 |
| rs6850557 | 0.00404606 | 0.417295012 | 0.01518697 | 0.68492502 | 0.00541026 |
| rs6863088 | 0.00026652 | 2.166432987 | 0.04781715 | 0.66113266 | 0.00542248 |
| rs1041067 | NA | 1.823670971 | 0.17898745 | 2.07360552 | 0.0054606 |
| rs17141840 | 0.02115822 | 1.230686828 | 0.71387947 | 1.84994048 | 0.00546749 |
| rs10406354 | 0.00121281 | 1.088478107 | 0.87097154 | 0.62946059 | 0.00548652 |
| rs6065460 | 0.05626947 | 0.587645404 | 0.24739883 | 0.60311188 | 0.00559256 |
| rs12667537 | 0.02875229 | 0.789227493 | 0.56782914 | 0.69015028 | 0.00562835 |
| rs17811425 | 0.01789273 | 1.428769234 | 0.28635744 | 1.46627399 | 0.00567987 |
| rs2302267 | 0.30851561 | 1.748933254 | 0.12694004 | 1.66927173 | 0.00569168 |
| rs4820059 | 0.00287257 | 2.658471404 | 0.02367452 | 1.49145813 | 0.00571302 |
| rs6621980 | 0.04939986 | 1.409589457 | 0.15015776 | 1.31936028 | 0.00575959 |
| rs1007212 | 0.16726864 | 2.729934463 | 0.01579015 | 1.46480877 | 0.00588403 |
| rs866484 | 0.06374432 | 4.219859274 | 0.00436883 | 1.64336082 | 0.00591764 |
| rs3181096 | 0.1075962 | 1.84576278 | 0.03149599 | 1.47683865 | 0.00593852 |
| rs2302759 | 0.10011032 | 0.580423115 | 0.2796878 | 0.6191119 | 0.00621838 |
| rs2275603 | 0.12468672 | 2.311760859 | 0.07374143 | 1.49849868 | 0.00623442 |
| rs5996577 | 0.02398456 | 0.515875154 | 0.32068033 | 1.67156256 | 0.00624054 |
| rs2076086 | 0.00126669 | 0.648216671 | 0.298268 | 0.69490504 | 0.00626233 |
| rs4639174 | 0.00444984 | 1.174127844 | 0.78806174 | 1.78382912 | 0.00628683 |
| rs17834679 | 0.02521038 | 0.789642141 | 0.47013849 | 0.68786418 | 0.00631208 |
| rs3024486 | 0.01728117 | 3.091031331 | 0.11776871 | 3.10843837 | 0.00636386 |
| rs2279590 | 0.00106384 | 1.351465322 | 0.44422561 | 1.44792048 | 0.00651877 |
| rs9867325 | 0.04684429 | 1.450965731 | 0.34480767 | 1.53618707 | 0.00659895 |
| rs2010452 | 0.04867542 | 1.797560506 | 0.18486799 | 1.54750999 | 0.00666053 |
| rs12451415 | 0.12088012 | 0.602191129 | 0.22225372 | 0.64537547 | 0.00668182 |
| rs4253655 | 0.0722436 | 1.127438262 | 0.78892856 | 1.63851165 | 0.00672637 |
| rs6058391 | 0.00238366 | 0.732955751 | 0.60068371 | 0.55342866 | 0.00688493 |

TABLE 4-continued

| | | | | | |
|---|---|---|---|---|---|
| rs7692976 | 0.05480184 | 0.391594532 | 0.01297711 | 0.69784007 | 0.00692522 |
| rs6482644 | 0.24768847 | 0.305341161 | 0.0030658 | 0.64947734 | 0.00697574 |
| rs9426315 | 0.06850014 | 0.886855435 | 0.74404124 | 1.46103026 | 0.00701027 |
| rs2286414 | 0.05552253 | 0.574738926 | 0.65899547 | 2.85777667 | 0.00711592 |
| rs6544865 | 0.0075062 | 1.277095333 | 0.48285441 | 1.51025069 | 0.00715909 |
| rs1984399 | 0.0342318 | 1.461046463 | 0.27809817 | 1.44433829 | 0.00726788 |
| rs1838065 | 0.03270155 | 1.464967692 | 0.24263104 | 1.43409468 | 0.00737466 |
| rs11214108 | 0.01288866 | 1.417426141 | 0.58443051 | 1.85014939 | 0.00742465 |
| rs717176 | 0.0188805 | 0.787432901 | 0.50995334 | 0.7104371 | 0.00748396 |
| rs1797646 | 0.11066569 | 0.337476773 | 0.00654404 | 0.68924202 | 0.00760094 |
| rs2238337 | 0.01187583 | 0.690759416 | 0.3183848 | 1.4161782 | 0.00764643 |
| rs763361 | 0.02843145 | 2.139825301 | 0.02812813 | 1.42502266 | 0.00770211 |
| rs4027402 | NA | 0.506797492 | 0.25934214 | 0.36264054 | 0.00772918 |
| rs970283 | 0.00445051 | 0.275876819 | 0.09376977 | 0.60133443 | 0.00779681 |
| rs4953292 | 0.06181018 | 0.778632189 | 0.42203158 | 0.69784319 | 0.00782152 |
| rs7541717 | 0.00269427 | 1.038205399 | 0.93208105 | 0.66420876 | 0.00787324 |
| rs1523474 | 0.23978875 | 0.499496867 | 0.06316575 | 0.67718014 | 0.00793313 |
| rs4902264 | NA | 0.506797492 | 0.25934214 | 0.37561345 | 0.00804314 |
| rs210431 | 0.06991452 | 1.52859881 | 0.08095319 | 1.29134824 | 0.00805292 |
| rs6780432 | 0.02470974 | 0.886809564 | 0.7963535 | 0.64673151 | 0.00808053 |
| rs1058240 | 0.0255244 | 0.429676157 | 0.09398897 | 0.62224421 | 0.0080995 |
| rs2305340 | 0.12689838 | 0.492242669 | 0.10309747 | 0.64405121 | 0.00812478 |
| rs6751395 | 0.00034599 | 0.969463603 | 0.93275275 | 0.70858004 | 0.00823818 |
| rs12881815 | 0.07772938 | 0.296239826 | 0.34610186 | 3.08321144 | 0.00825819 |
| rs9991904 | 0.00245033 | 0.652163756 | 0.20495758 | 0.70286829 | 0.00826226 |
| rs509749 | 0.05996023 | 1.243435996 | 0.59863126 | 1.43368631 | 0.00828454 |
| rs1044141 | 0.05186795 | 1.966917559 | 0.09285948 | 1.55179894 | 0.00837565 |
| rs878081 | 0.0286662 | 0.675150083 | 0.29845254 | 0.67339544 | 0.00838392 |
| rs2227827 | 0.26149332 | 12.48444708 | 0.00172115 | 2.85293367 | 0.00839616 |
| rs11574113 | NA | 0.354546359 | 0.1309925 | 0.22168005 | 0.0084421 |
| rs17110948 | 0.01809374 | 0.456298626 | 0.19790608 | 0.53511478 | 0.00850426 |
| rs1865462 | 0.26604918 | 1.166206662 | 0.88114281 | 2.40061042 | 0.00851779 |
| rs1552323 | 0.02747993 | 1.980703511 | 0.16245636 | 1.68803574 | 0.00853525 |
| rs872071 | 0.01543522 | 1.240225714 | 0.53464507 | 0.71596244 | 0.00867939 |
| rs11852361 | 0.05155452 | 0.197387295 | 0.15503289 | 0.49653661 | 0.00879554 |
| rs2288522 | 0.06950403 | 1.877809135 | 0.20030419 | 1.7000779 | 0.00883537 |
| rs10854166 | 0.03416572 | 1.991587477 | 0.03098742 | 1.42534666 | 0.00884885 |
| rs17419586 | 0.00291577 | 1.623563578 | 0.23455732 | 1.50606072 | 0.00891196 |
| rs8078439 | 0.04810873 | 0.987701372 | 0.97346744 | 1.49666589 | 0.00892432 |
| rs2569190 | 0.00646771 | 0.863159962 | 0.69090086 | 1.41990798 | 0.00895345 |
| rs17748322 | 0.50840081 | 2.283820346 | 0.0477614 | 1.50698683 | 0.00897021 |
| rs17228097 | 0.1563137 | 2.712132468 | 0.02463277 | 1.57527645 | 0.00899615 |
| rs10104302 | 0.04726518 | 2.153080222 | 0.1051811 | 1.48498599 | 0.00903621 |
| rs17283264 | 0.00148629 | 0.670047968 | 0.58188286 | 2.14058282 | 0.00919713 |
| rs1062069 | 0.04672765 | 4.424252439 | 0.01904235 | 1.82622304 | 0.00948614 |
| rs1724120 | 0.06606352 | 0.512380618 | 0.06772627 | 0.70630159 | 0.00954347 |
| rs7647903 | 0.28448998 | 2.528852728 | 0.1439632 | 1.51632475 | 0.00955962 |
| rs11237451 | 0.06356768 | 0.439096926 | 0.10696314 | 0.69088709 | 0.0095633 |
| rs10165797 | 0.04788534 | 1.256490192 | 0.45071999 | 1.39187312 | 0.00958124 |
| rs1206486 | 0.03825241 | 1.837816069 | 0.22290112 | 1.47214103 | 0.00958255 |
| rs706121 | 0.00133522 | 1.557420871 | 0.29407753 | 1.59146367 | 0.00958826 |
| rs13042473 | 0.25507792 | 0.386478551 | 0.01544164 | 0.64042143 | 0.00972508 |
| rs3024498 | 0.06700756 | 0.191015467 | 0.00971569 | 0.67509588 | 0.00975546 |
| rs7289754 | 0.67991022 | 2.249557811 | 0.0196301 | 1.4390963 | 0.00976474 |
| rs11168267 | NA | 0.262332634 | 0.09134851 | 0.28068663 | 0.0098283 |
| rs1918309 | 0.01258535 | 1.527641748 | 0.18439689 | 1.40615531 | 0.00991575 |
| rs17671456 | 0.06629775 | 2.213446139 | 0.15422973 | 1.67286965 | 0.00996644 |

What is claimed is:

1. A method for assigning a treatment comprising administration of Factor VIII (FVIII) based on predicting the risk of developing antibodies against Factor VIII (FVIII) in an individual diagnosed with Hemophilia, the method comprising the steps of:
   (a) detecting the identity of the nucleotides corresponding to the genomic position consisting of SNPs rs11744216, rs13206518, rs3211834, rs1863993, rs4147385, and rs1567748 in a biological sample from the individual; and
   (b) predicting the risk of the individual of developing antibodies to FVIII, wherein the detection of the SNPs associated with an odds ratio of less than 1 is predictive of a decreased risk of developing antibodies against FVIII and the detection of the SNPs associated with an odds ratio of more than 1.0 is predictive of an increased risk of developing antibodies against FVIII;
   (c) assigning a treatment comprising administration of FVIII to an individual with a predicted decreased risk of developing antibodies against FVIII and administering said treatment to said individual; and
   (d) not assigning a treatment comprising administration of FVIII to an individual with a predicted increased risk of developing antibodies against FVIII and administering a treatment comprising FVIII bypass therapy to said individual.

2. The method of claim 1, wherein the individual is being treated by administration of FVIII.

3. The method of claim 1, wherein the individual has not received therapy comprising administration of FVIII.

4. The method of claim 1, wherein the individual has received therapy comprising administration of FVIII.

5. The method of claim 1, wherein the individual has been diagnosed with mild Hemophilia.

6. The method of claim 1, wherein the individual has been diagnosed with moderate Hemophilia.

7. The method of claim 1, wherein the individual has been diagnosed with severe Hemophilia.

8. The method of claim 1, wherein the step a) of detecting the identity comprises amplifying a nucleic acid present in the biological sample.

9. The method of claim 1, wherein the step a) of detecting the identity comprises a technique selected from the group consisting of mass spectroscopy, RT-PCR, microarray hybridization, pyrosequencing, thermal cycle sequencing, capillary array sequencing, and solid phase sequencing.

10. The method of claim 1, wherein the step a) of detecting the identity comprises a method selected from the group consisting of a hybridization-based method, an enzymatic-based method, a PCR-based method, a sequencing method, a ssDNA conformational method, and a DNA melting temperature assay.

11. The method of claim 1, wherein the step a) of detecting the identity comprises microarray hybridization.

12. The method of claim 1, wherein the FVIII bypass therapy comprises administration of a non-Factor VIII hemostatic agent.

13. The method of claim 1, wherein assigning treatment comprises adjusting a dosage and/or frequency of Factor VIII administration based on the predicted risk of developing antibodies against Factor VIII.

14. The method of claim 13, wherein adjusting a dosage of Factor VIII comprises increasing the dosage and/or frequency of Factor VIII administered to an individual with a predicted decreased risk of developing antibodies against Factor VIII.

15. The method of claim 13, wherein adjusting a dosage of Factor VIII comprises decreasing the dosage and/or frequency of Factor VIII administered to an individual with a predicted increased risk of developing antibodies against Factor VIII.

16. The method of claim 1, wherein assigning treatment comprises adjusting a dosage and/or frequency of a non-Factor VIII hemostatic agent administration based on the predicted risk of developing antibodies against Factor VIII.

17. The method of claim 13, wherein adjusting a dosage of a non-Factor VIII hemostatic agent comprises decreasing the dosage and/or frequency of a non-Factor VIII hemostatic agent administered to an individual with a predicted decreased risk of developing antibodies against Factor VIII.

18. The method of claim 13, wherein adjusting a dosage of a non-Factor VIII hemostatic agent comprises increasing the dosage and/or frequency of a non-Factor VIII hemostatic agent administered to an individual with a predicted increased risk of developing antibodies against Factor VIII.

19. The method of claim 1, wherein the presence of rs13206518 or rs11744216 is predictive of a decreased risk of developing antibodies against Factor VIII.

20. The method of claim 1, wherein the presence of rs1863993 or rs4147385 is predictive of an increased risk of developing antibodies against Factor VIII.

21. A method for assigning a treatment comprising administration of Factor FVIII (FVIII) based on predicting the risk of developing antibodies against Factor VIII (FVIII) in an individual diagnosed with Hemophilia A, wherein the individual is being treated by FVIII bypass therapy, the method comprising the steps of:
   (a) detecting the identity of the nucleotides corresponding to the genomic position consisting of SNPs rs11744216, rs13206518, rs3211834, rs1863993, rs4147385, and rs1567748, in a biological sample from the individual;
   (b) predicting the risk of the individual of developing antibodies to FVIII, wherein the detection of the SNPs associated with an odds ratio of less than 1 is predictive of a decreased risk of developing antibodies against FVIII and the detection of the SNPs associated with an odds ratio of more than 1.0 is predictive of an increased risk of developing antibodies against FVIII;
   (c) assigning a treatment comprising FVIII bypass therapy to an individual with a predicted increased risk of developing antibodies against FVIII and administering said treatment to said individual; and
   (d) not assigning a treatment comprising administration of FVIII bypass therapy to an individual with a predicted decreased risk of developing antibodies against FVIII and administering a treatment comprising administration of FVIII to said individual.

22. The method of claim 21, wherein the presence of rs13206518 or rs11744216 is predictive of a decreased risk of developing antibodies against Factor VIII.

23. The method of claim 21, wherein the presence of SNPs rs1863993 or rs4147385 is predictive of an increased risk of developing antibodies against Factor VIII.

24. A method for assigning a treatment comprising administration of Factor FVIII (FVIII) based on predicting the risk of developing antibodies against Factor VIII (FVIII) in an individual diagnosed with Hemophilia A, wherein the individual is being treated by administration of FVIII, the method comprising the steps of:
   (a) detecting the identity of the nucleotides corresponding to the genomic position consisting of SNPs rs11744216, rs13206518, rs3211834, rs1863993, rs4147385, and rs1567748, in a biological sample from the individual;

(b) predicting the risk of the individual of developing antibodies to FVIII, wherein the detection of the SNPs associated with an odds ratio of less than 1 is predictive of a decreased risk of developing antibodies against FVIII and the detection of the SNPs associated with an odds ratio of more than 1.0 is predictive of an increased risk of developing antibodies against F VIII;

(c) assigning a treatment comprising FVIII bypass therapy to an individual with a predicted increased risk of developing antibodies against FVIII and administering said treatment to said individual; and (d) not assigning a treatment comprising administration of FVIII bypass therapy to an individual with a predicted decreased risk of developing antibodies against FVIII and administering a treatment comprising administration of FVIII to the individual.

25. The method of claim 24, wherein the presence of rs13206518 or rs11744216 is predictive of a decreased risk of developing antibodies against Factor VIII.

26. The method of claim 24, wherein the presence of SNPs rs1863993 or rs4147385 is predictive of an increased risk of developing antibodies against Factor VIII.

* * * * *

SEQUENCE LISTING

<160> NUMBER OF SEQ ID NOS: 1

<210> SEQ ID NO 1
<211> LENGTH: 52
<212> TYPE: DNA
<213> ORGANISM: Homo sapiens
<220> FEATURE:
<221> NAME/KEY: purine
<222> LOCATION: (27)..(27)
<223> OTHER INFORMATION: nucleotide r can be g or a

<400> SEQUENCE: 1
ttgccactac ttgtctccaa agaaacrtaa gaatgcttta tcatacaaca gt        52